(12) United States Patent
Xu et al.

(10) Patent No.: US 11,795,230 B2
(45) Date of Patent: Oct. 24, 2023

(54) ANTI-CD27 ANTIBODIES AND USE THEREOF

(71) Applicant: DINGFU BIOTARGET CO., LTD., Jiangsu (CN)

(72) Inventors: Ting Xu, Jiangsu (CN); Yan Luan, Jiangsu (CN); Jianjian Peng, Jiangsu (CN); Kai Fu, Jiangsu (CN)

(73) Assignee: DINGFU BIOTARGET CO., LTD., Jiangsu (CN)

( * ) Notice: Subject to any disclaimer, the term of this patent is extended or adjusted under 35 U.S.C. 154(b) by 245 days.

(21) Appl. No.: 17/046,884

(22) PCT Filed: Apr. 13, 2018

(86) PCT No.: PCT/CN2018/083095
§ 371 (c)(1),
(2) Date: Oct. 12, 2020

(87) PCT Pub. No.: WO2019/196117
PCT Pub. Date: Oct. 17, 2019

(65) Prior Publication Data
US 2021/0179726 A1 Jun. 17, 2021

(51) Int. Cl.
*A61K 39/395* (2006.01)
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/565* (2013.01); *C07K 2317/92* (2013.01)

(58) Field of Classification Search
None
See application file for complete search history.

(56) References Cited

U.S. PATENT DOCUMENTS 7,977,461 B2 * 7/2011 Takayama .............. C07K 16/28
435/328
9,169,325 B2 * 10/2015 Keler ...................... A61P 13/12
9,427,464 B2 * 8/2016 Nakamura ......... C07K 16/3046

FOREIGN PATENT DOCUMENTS

CN 102918059 A 2/2013
WO 2011130434 A2 10/2011
(Continued)

OTHER PUBLICATIONS

MacCallum et al.,Antibody-antigen interactions: contact analysis and binding site topography, J. Mol. Biol. 262:732-745, 1996.*
(Continued)

*Primary Examiner* — Claire Kaufman
(74) *Attorney, Agent, or Firm* — Honigman LLP; Thomas A. Wootton, Esq.; Jonathan P. O'Brien

(57) ABSTRACT

The present disclosure provides an antibody, or an antigen binding fragment or variant thereof, which binds to CD27 and exhibits at least one of the following properties: specifically binds to CD27 with a $K_D$ of $10^{-8}$ M or less; activates and/or increases CD27 mediated NF-κB activity; stimulates CD4+ and/or CD8+ T cell proliferation; binds to human CD27 expressed on a cell surface; stimulates secretion of IFN-γ by CD4+ and/or CD8+ T cells. The present disclosure also provides a method for preparing and using said antibody.

8 Claims, 13 Drawing Sheets

Specification includes a Sequence Listing.

(56) References Cited

FOREIGN PATENT DOCUMENTS

| WO | 2012004367 A1 | 1/2012 |
| WO | 2013126810 A1 | 8/2013 |
| WO | 2013138586 A1 | 9/2013 |
| WO | 2018058022 A1 | 3/2018 |

OTHER PUBLICATIONS

Chen et al., Enhancement and destruction of antibody function by somatic mutation: unequal occurrence is controlled by V gene combinatorial associations, EMBO J. 14(12):2784-2794, 1995.*
Yan et al. Construction of a synthetic phage-displayed Nanobody library with CDR3 regions randomized by trinucleotide cassettes for diagnostic applications, J. Translational Med.12:343, http:/www.translational-medicine.com/content/12/1/343, 12 pages, 2014.*
Sela-Culang et al. Frontiers in Immunology, vol. 4, Article 302, doi: 10.3389/fimmu.2013.00302, Oct. 2013.*
Supplementary Partial European Search Report of EP 18914395.1 dated Jan. 5, 2022.
He, Li-Zhen, et al., agonist Anti-Human CD27 Monoclonal Antibody Induces T Cell Activation and Tumor Immunity in Human CD27-Transgenic Mice, The J of Immunology, 191:4174-4183, Sep. 11, 2013, The Am Assoc of Immunologists, Inc.
Wei, Si-Ming, et al., Anti-CD27 Antibody potentiates Antitumor Effect of Dendritic Cell-Based Vaccine in Prostate Cancer-Bearing Mice, Int Surg. 100:155-163, 2015.
International Search Report from PCT/CN2018/083095 dated Jan. 21, 2019.

* cited by examiner

SEQUENCE LISTING

```
<160> NUMBER OF SEQ ID NOS: 152

<210> SEQ ID NO 1
<211> LENGTH: 122
<212> TYPE: PRT
<213> ORGANISM: Artificial Sequence
<220> FEATURE:
<223> OTHER INFORMATION: 1A8 VH

<400> SEQUENCE: 1

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ser Phe Thr Ser Ser
            20                  25                  30

Trp Met His Trp Val Lys Gln Arg Pro Gly Gln Gly Leu Glu Trp Ile
        35                  40                  45

Gly Met Ile His Pro Asp Ser Gly Phe Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Arg Thr Ser Tyr Tyr Asp Thr Ser Tyr Thr Ser Met Asp Phe Trp
            100                 105                 110

Gly Gln Gly Asn Ser Val Thr Val Ser Ser
        115                 120

<210> SEQ ID NO 2
<211> LENGTH: 366
<212> TYPE: DNA
<213> ORGANISM: Artificial Sequence
<220> FEATURE:
<223> OTHER INFORMATION: 1A8 VH nucleotide

<400> SEQUENCE: 2
gaggtgcagc tgcaggagtc tgggggctgaa ttggtaaagc ctgggggcttc agtgaagttg      60 tcctgcaagg cttctggcta cagtttcacc agctcctgga tgcactgggt gaagcagagg     120
```

```
cctggacaag gccttgagtg gattggaatg attcatcctg atagtggttt tactaactac      180
aatgagaagt tcaagagcaa ggccacactg actgtagaca atcctccag cacagcctac      240 atgcgcctca gcagcctgac atctgaggac tctgcggtct attactgtgc aaggacctct      300
tactacgata ctagctacac ttctatggac ttctggggtc aaggaaactc agtcaccgtc      360
tcctca                                                                 366
```

<210> SEQ ID NO 3
<211> LENGTH: 107
<212> TYPE: PRT
<213> ORGANISM: Artificial Sequence
<220> FEATURE:
<223> OTHER INFORMATION: 1A8VL

<400> SEQUENCE: 3

```
Asp Ile Val Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Leu
                85                  90                  95

Thr Phe Gly Ala Gly Thr Lys Leu Glu Leu Lys
            100                 105
```

<210> SEQ ID NO 4
<211> LENGTH: 321
<212> TYPE: DNA
<213> ORGANISM: Artificial Sequence
<220> FEATURE:
<223> OTHER INFORMATION: 1A8VL nucleotide

<400> SEQUENCE: 4

```
gatattgtgc tgacccagtc tccagccatc ctgtctgtga gtccaggaga aagagtcagt      60
ttctcctgca gggccagtca gagcattggc acaagcatac attggtatca gcaaagaaca      120
aatggttctc caaggcttct cataaagtat gcttctgagt ctatctctgg gatcccttcc      180
aggtttagtg gcagtggatc agggacagat tttactctta gcatcaacag tgtggagtct      240
gaagatattg cagattatta ctgtcaacaa agtaatagct ggccactcac gttcggtgct      300
gggaccaagc tggagctgaa a                                                321
```

<210> SEQ ID NO 5
<211> LENGTH: 5
<212> TYPE: PRT
<213> ORGANISM: Artificial Sequence
<220> FEATURE:
<223> OTHER INFORMATION: 1A8 HCDR1

<400> SEQUENCE: 5

```
Ser Ser Trp Met His
1               5
```

<210> SEQ ID NO 6

```
<211> LENGTH: 17
<212> TYPE: PRT
<213> ORGANISM: Artificial Sequence
<220> FEATURE:
<223> OTHER INFORMATION: 1A8 HCDR2

<400> SEQUENCE: 6

Met Ile His Pro Asp Ser Gly Phe Thr Asn Tyr Asn Glu Lys Phe Lys
1               5                   10                  15
Ser

<210> SEQ ID NO 7
<211> LENGTH: 13
<212> TYPE: PRT
<213> ORGANISM: Artificial Sequence
<220> FEATURE:
<223> OTHER INFORMATION: 1A8 HCDR3

<400> SEQUENCE: 7

Thr Ser Tyr Tyr Asp Thr Ser Tyr Thr Ser Met Asp Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: 1A8 LCDR1

<400> SEQUENCE: 8

Arg Ala Ser Gln Ser Ile Gly Thr Ser Ile His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: 1A8 LCDR2

<400> SEQUENCE: 9

Tyr Ala Ser Glu Ser Ile Ser
1               5

<210> SEQ ID NO 10
<211> LENGTH: 9
<212> TYPE: PRT
<213> ORGANISM: Artificial Sequence
<220> FEATURE:
<223> OTHER INFORMATION: 1A8 LCDR3

<400> SEQUENCE: 10

Gln Gln Ser Asn Ser Trp Pro Leu Thr
1               5

<210> SEQ ID NO 11
<211> LENGTH: 120
<212> TYPE: PRT
<213> ORGANISM: Artificial Sequence
<220> FEATURE:
<223> OTHER INFORMATION: 2B8 VH

<400> SEQUENCE: 11

Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Asn Phe Asn Thr Tyr
```

```
                20                  25                  30
Thr Met Asn Trp Val Arg Gln Ala Pro Gly Lys Gly Leu Glu Trp Val
             35                  40                  45

Ala Arg Ile Arg Tyr Lys Ser Asn Asn Tyr Ala Thr Tyr Tyr Ala Asp
         50                  55                  60

Ser Val Lys Asp Arg Phe Thr Ile Ser Arg Asp Asp Ser Glu Ser Ile
 65                  70                  75                  80

Leu Tyr Leu Gln Met Asn Asn Leu Arg Thr Asp Asp Thr Ala Ile Tyr
                 85                  90                  95

Phe Cys Val Arg Glu Leu Gly Leu Trp Tyr Phe Asp Val Trp Gly Ala
             100                 105                 110

Gly Thr Thr Val Thr Val Ser Ser
             115                 120

<210> SEQ ID NO 12
<211> LENGTH: 360
<212> TYPE: DNA
<213> ORGANISM: Artificial Sequence
<220> FEATURE:
<223> OTHER INFORMATION: 2B8 VH nucleotide

<400> SEQUENCE: 12
gaggtgcagc tgcaggagtc tggtggagga ttggtgcagc ctaaagggtc attgaaactc      60
tcatgtgcag cctctggatt caacttcaat acctacacca tgaactgggt ccgccaggct     120
ccaggaaagg gtttggaatg ggttgctcgc ataagatata aaagtaataa ttatgcaaca     180
tattatgccg attcagtgaa agacagattc accatctcca gagatgattc agaaagcatc     240
ctctatctgc aaatgaacaa cttgagaact gacgacacag ccatttattt ctgtgtgagg     300
gaactgggac tgtggtactt cgatgtctgg ggcgcaggga ccacggtcac cgtctcctca     360

<210> SEQ ID NO 13
<211> LENGTH: 107
<212> TYPE: PRT
<213> ORGANISM: Artificial Sequence
<220> FEATURE:
<223> OTHER INFORMATION: 2B8VL

<400> SEQUENCE: 13

Asp Ile Val Met Thr Gln Ser Pro Ser Tyr Leu Ala Ala Ser Pro Gly
 1               5                  10                  15

Glu Thr Ile Thr Ile Asn Cys Arg Ala Ser Lys Ser Ile Ser Lys Tyr
             20                  25                  30

Leu Ala Trp Tyr Arg Glu Lys Pro Gly Lys Thr Asn Asn Leu Leu Ile
         35                  40                  45

Tyr Ser Gly Ser Thr Leu Gln Ser Gly Ile Pro Ser Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Leu
                 85                  90                  95

Thr Phe Gly Ala Gly Thr Lys Leu Glu Leu Lys
             100                 105

<210> SEQ ID NO 14
<211> LENGTH: 321
<212> TYPE: DNA
<213> ORGANISM: Artificial Sequence
<220> FEATURE:
```

<223> OTHER INFORMATION: 2B8VL nucleotide

<400> SEQUENCE: 14

```
gacattgtga tgacccagtc tccatcttat cttgctgcat ctcctggaga aaccattact    60
ataaattgca gggcaagtaa gagcattagc aaatatttag cctggtatcg agagaaacct   120
gggaaaacta ataatcttct tatctactct ggatccactt tgcaatctgg aattccatca   180
aggttcagtg gcagtggatc tggtacagat ttcactctca ccatcagtag cctggagcct   240
gaagattttg caatgtatta ctgtcaacag cataatgaat acccgctcac gttcggtgct   300
gggaccaagc tggagctgaa a                                             321
```

<210> SEQ ID NO 15
<211> LENGTH: 5
<212> TYPE: PRT
<213> ORGANISM: Artificial Sequence
<220> FEATURE:
<223> OTHER INFORMATION: 2B8 HCDR1

<400> SEQUENCE: 15

Thr Tyr Thr Met Asn
1               5

<210> SEQ ID NO 16
<211> LENGTH: 19
<212> TYPE: PRT
<213> ORGANISM: Artificial Sequence
<220> FEATURE:
<223> OTHER INFORMATION: 2B8 HCDR2

<400> SEQUENCE: 16

Arg Ile Arg Tyr Lys Ser Asn Asn Tyr Ala Thr Tyr Tyr Ala Asp Ser
1               5                   10                  15
Val Lys Asp

<210> SEQ ID NO 17
<211> LENGTH: 9
<212> TYPE: PRT
<213> ORGANISM: Artificial Sequence
<220> FEATURE:
<223> OTHER INFORMATION: 2B8 HCDR3

<400> SEQUENCE: 17

Glu Leu Gly Leu Trp Tyr Phe Asp Val
1               5

<210> SEQ ID NO 18
<211> LENGTH: 11
<212> TYPE: PRT
<213> ORGANISM: Artificial Sequence
<220> FEATURE:
<223> OTHER INFORMATION: 2B8 LCDR1

<400> SEQUENCE: 18

Arg Ala Ser Lys Ser Ile Ser Lys Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: 2B8 LCDR2

<400> SEQUENCE: 19

```
Ser Gly Ser Thr Leu Gln Ser
1               5
```

<210> SEQ ID NO 20
<211> LENGTH: 9
<212> TYPE: PRT
<213> ORGANISM: Artificial Sequence
<220> FEATURE:
<223> OTHER INFORMATION: 2B8 LCDR3

<400> SEQUENCE: 20

```
Gln Gln His Asn Glu Tyr Pro Leu Thr
1               5
```

<210> SEQ ID NO 21
<211> LENGTH: 116
<212> TYPE: PRT
<213> ORGANISM: Artificial Sequence
<220> FEATURE:
<223> OTHER INFORMATION: 2E7 VH

<400> SEQUENCE: 21

```
Glu Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Gln Trp Met
        35                  40                  45

Gly Trp Ile Asn Thr Asn Ser Gly Val Pro Thr Tyr Val Glu Asp Phe
    50                  55                  60

Lys Gly Arg Phe Ala Phe Ser Leu Glu Ser Ser Ala Asn Thr Ala Tyr
65                  70                  75                  80

Leu Gln Ile Asn Asn Leu Lys Asn Glu Asp Thr Ala Ile Tyr Phe Cys
                85                  90                  95

Thr Arg Glu Gly Asp Ala Leu Asp Tyr Trp Gly Gln Gly Thr Ser Val
            100                 105                 110

Thr Val Ser Ser
        115
```

<210> SEQ ID NO 22
<211> LENGTH: 348
<212> TYPE: DNA
<213> ORGANISM: Artificial Sequence
<220> FEATURE:
<223> OTHER INFORMATION: 2E7 VH nucleotide

<400> SEQUENCE: 22

```
gaggtgcagc tgcaggagtc tggacctgag ctgaagaagc ctggagagac agtcaagatc    60
tcctgcaagg cttctgggta taccttcaca acctatggaa tgagctgggt gaaacaggct   120
ccaggaaagg gtttacagtg gatgggctgg ataaacacca actctggagt gccaacctat   180
gttgaggact caagggacg gtttgccttc tctttggaat cctctgccaa cactgcctat   240
ttgcagatca caaccctcaa aaatgaggac acggctatat acttctgtac aagagagggg   300
gatgctctgg actactgggg tcaaggaacc tcagtcaccg tctcctca              348
```

<210> SEQ ID NO 23
<211> LENGTH: 107
<212> TYPE: PRT
<213> ORGANISM: Artificial Sequence
<220> FEATURE:

<223> OTHER INFORMATION: 2E7VL

<400> SEQUENCE: 23

Asp Ile Val Met Thr Gln Ser Thr Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Arg Arg Trp Ile Tyr
        35                  40                  45

Asp Thr Ser Arg Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Thr Pro Pro Phe
                85                  90                  95

Thr Phe Gly Ala Gly Thr Lys Leu Glu Leu Lys
            100                 105

<210> SEQ ID NO 24
<211> LENGTH: 321
<212> TYPE: DNA
<213> ORGANISM: Artificial Sequence
<220> FEATURE:
<223> OTHER INFORMATION: 2E7VL nucleotide

<400> SEQUENCE: 24
gatattgtga tgacacaatc tacagcaatc atgtctgcat ctccagggga gaaggtcacc      60
atgacctgca gtgccagctc aagtgtaagt tacatgcact ggtaccagca gaagtcaggc     120
acctccccca aagatggat ttatgacaca tccagactgg cttctggagt ccctgctcgc      180
ttcagtggca gtgggtctgg gacctcttac tctctcacaa tcagcagcat ggaggctgaa     240
gatgctgcca cttattactg ccagcagtgg agtaataccc cacccttcac gttcggtgct     300
gggaccaagt tggagctgaa a                                                321

<210> SEQ ID NO 25
<211> LENGTH: 5
<212> TYPE: PRT
<213> ORGANISM: Artificial Sequence
<220> FEATURE:
<223> OTHER INFORMATION: 2E7 HCDR1

<400> SEQUENCE: 25

Thr Tyr Gly Met Ser
1               5

<210> SEQ ID NO 26
<211> LENGTH: 17
<212> TYPE: PRT
<213> ORGANISM: Artificial Sequence
<220> FEATURE:
<223> OTHER INFORMATION: 2E7 HCDR2

<400> SEQUENCE: 26

Trp Ile Asn Thr Asn Ser Gly Val Pro Thr Tyr Val Glu Asp Phe Lys
1               5                   10                  15
Gly

<210> SEQ ID NO 27
<211> LENGTH: 7
<212> TYPE: PRT

<210> SEQ ID NO 27
<211> LENGTH: 6
<212> TYPE: PRT
<213> ORGANISM: Artificial Sequence
<220> FEATURE:
<223> OTHER INFORMATION: 2E7 HCDR3

<400> SEQUENCE: 27

Glu Gly Asp Ala Leu Asp Tyr
1               5

<210> SEQ ID NO 28
<211> LENGTH: 10
<212> TYPE: PRT
<213> ORGANISM: Artificial Sequence
<220> FEATURE:
<223> OTHER INFORMATION: 2E7 LCDR1

<400> SEQUENCE: 28

Ser Ala Ser Ser Ser Val Ser Tyr Met His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: 2E7 LCDR2

<400> SEQUENCE: 29

Asp Thr Ser Arg Leu Ala Ser
1               5

<210> SEQ ID NO 30
<211> LENGTH: 10
<212> TYPE: PRT
<213> ORGANISM: Artificial Sequence
<220> FEATURE:
<223> OTHER INFORMATION: 2E7 LCDR3

<400> SEQUENCE: 30

Gln Gln Trp Ser Asn Thr Pro Pro Phe Thr
1               5                   10

<210> SEQ ID NO 31
<211> LENGTH: 116
<212> TYPE: PRT
<213> ORGANISM: Artificial Sequence
<220> FEATURE:
<223> OTHER INFORMATION: 3E7 VH

<400> SEQUENCE: 31

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu His Trp Met
        35                  40                  45

Gly Trp Ile Asn Thr His Ser Gly Ala Pro Thr Tyr Val Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Ile Asn Glu Asp Thr Ala Thr Tyr Phe Cys
                85                  90                  95

Ala Arg Glu Gly Asp Ala Leu Asp Tyr Trp Gly Gln Gly Thr Ser Val
            100                 105                 110

Thr Val Ser Ser
        115

<210> SEQ ID NO 32
<211> LENGTH: 348
<212> TYPE: DNA
<213> ORGANISM: Artificial Sequence
<220> FEATURE:
<223> OTHER INFORMATION: 3E7 VH nucleotide

<400> SEQUENCE: 32

```
cagatccagc tggtgcagag cggaccagaa ctgaagaagc caggagagac agtcaagatc      60
tcctgcaagg cttctggata tacgttcaca acctatggaa tgagctgggt gaaacaggct     120
ccaggaaagg gtttgcactg gatgggctgg ataaacaccc actctggagc gccaacatat     180
gttgatgact caagggacg gtttgccttc tctttggaaa cctctgccag cactgccttt     240
ttgcagatca acaacctcat aaatgaggac acggctacat atttctgtgc aagagagggg     300
gatgctctgg actactgggg tcaaggaacc tcagtcaccg tctcctca                  348
```

<210> SEQ ID NO 33
<211> LENGTH: 107
<212> TYPE: PRT
<213> ORGANISM: Artificial Sequence
<220> FEATURE:
<223> OTHER INFORMATION: 3E7VL

<400> SEQUENCE: 33

Asp Ile Val Met Thr Gln Thr Thr Ala Ile Met Ser Ala Phe Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Arg Asn Pro Pro Phe
                85                  90                  95

Thr Phe Gly Ala Gly Thr Lys Leu Glu Leu Lys
            100                 105

<210> SEQ ID NO 34
<211> LENGTH: 321
<212> TYPE: DNA
<213> ORGANISM: Artificial Sequence
<220> FEATURE:
<223> OTHER INFORMATION: 3E7VL nucleotide

<400> SEQUENCE: 34

```
gacattgtga tgacccaaac tacagcaatc atgtctgcat tccagggga gaaggtcacc       60
atgacctgca gtgccagctc aagtgtaagt tacatgcact ggtaccagca gaagtcaggc     120
acctccccca aaagatggat ttatgacaca tccaaactgg cttctggagt ccctgttcgc     180
ttcagtggca gtgggtctgg gacctcttac tctctcacaa tcagcaacat ggaggctgaa     240
gatgctgcca ttattattg ccagcagtgg agtcgtaacc cacccttcac gttcggtgct     300
gggaccaagc tggagctgaa a                                              321
```

```
<210> SEQ ID NO 35
<211> LENGTH: 5
<212> TYPE: PRT
<213> ORGANISM: Artificial Sequence
<220> FEATURE:
<223> OTHER INFORMATION: 3E7 HCDR1

<400> SEQUENCE: 35

Thr Tyr Gly Met Ser
1               5

<210> SEQ ID NO 36
<211> LENGTH: 17
<212> TYPE: PRT
<213> ORGANISM: Artificial Sequence
<220> FEATURE:
<223> OTHER INFORMATION: 3E7 HCDR2

<400> SEQUENCE: 36

Trp Ile Asn Thr His Ser Gly Ala Pro Thr Tyr Val Asp Asp Phe Lys
1               5                   10                  15

Gly

<210> SEQ ID NO 37
<211> LENGTH: 7
<212> TYPE: PRT
<213> ORGANISM: Artificial Sequence
<220> FEATURE:
<223> OTHER INFORMATION: 3E7 HCDR3

<400> SEQUENCE: 37

Glu Gly Asp Ala Leu Asp Tyr
1               5

<210> SEQ ID NO 38
<211> LENGTH: 10
<212> TYPE: PRT
<213> ORGANISM: Artificial Sequence
<220> FEATURE:
<223> OTHER INFORMATION: 3E7 LCDR1

<400> SEQUENCE: 38

Ser Ala Ser Ser Ser Val Ser Tyr Met His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: 3E7 LCDR2

<400> SEQUENCE: 39

Asp Thr Ser Lys Leu Ala Ser
1               5

<210> SEQ ID NO 40
<211> LENGTH: 10
<212> TYPE: PRT
<213> ORGANISM: Artificial Sequence
<220> FEATURE:
<223> OTHER INFORMATION: 3E7 LCDR3

<400> SEQUENCE: 40

Gln Gln Trp Ser Arg Asn Pro Pro Phe Thr
1               5                   10
```

<210> SEQ ID NO 41
<211> LENGTH: 121
<212> TYPE: PRT
<213> ORGANISM: Artificial Sequence
<220> FEATURE:
<223> OTHER INFORMATION: 3B8 VH

<400> SEQUENCE: 41

```
Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
        35                  40                  45

Gly Val Ile Trp Gly Asp Gly Thr Thr Asn Tyr His Ser Ala Leu Ile
    50                  55                  60

Ser Arg Leu Ile Ile Ser Lys Asp Asn Ser Lys Ser Gln Val Phe Leu
65              70                  75                  80

Lys Leu Asn Ser Leu Gln Thr Asp Asp Thr Ala Thr Tyr Tyr Cys Ala
            85                  90                  95

Lys Glu Gly Asp Tyr Gly Asp Tyr Val Gly Trp Phe Ala Tyr Trp Gly
            100                 105                 110

Gln Gly Thr Leu Val Thr Val Ser Ala
        115                 120
```

<210> SEQ ID NO 42
<211> LENGTH: 363
<212> TYPE: DNA
<213> ORGANISM: Artificial Sequence
<220> FEATURE:
<223> OTHER INFORMATION: 3B8 VH nucleotide

<400> SEQUENCE: 42

```
caggtccagc tgcaggagtc aggacctggc ctggtggcgc cctcacagag cctgtccatc      60
acatgcactg tctcagggtt ctcattaacc aactatgctg taagctgggt tcgccagcct     120
ccaggaaagg gtctggagtg gctgggagta atatggggtg acgggaccac aaattatcat     180
tcagctctca tatccagact gattatcagc aaggataact ccaagagcca agttttctta     240
aaactgaaca gtctgcaaac tgatgacaca gccacgtact actgtgccaa agagggcgac     300
tatggtgact acgtaggctg gtttgcttac tggggccaag gactctggt cactgtctct      360 gca                                                                   363
```

<210> SEQ ID NO 43
<211> LENGTH: 111
<212> TYPE: PRT
<213> ORGANISM: Artificial Sequence
<220> FEATURE:
<223> OTHER INFORMATION: 3B8VL

<400> SEQUENCE: 43

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60
```

Arg Phe Ser Gly Ser Gly Ser Gly Thr Asp Phe Ser Leu Asn Ile His
65                  70                  75                  80

Pro Val Glu Glu Asp Asp Phe Ala Met Tyr Phe Cys Gln Gln Ser Arg
                85                  90                  95

Lys Ile Pro Tyr Thr Phe Gly Gly Gly Thr Lys Leu Glu Ile Lys
            100                 105                 110

<210> SEQ ID NO 44
<211> LENGTH: 333
<212> TYPE: DNA
<213> ORGANISM: Artificial Sequence
<220> FEATURE:
<223> OTHER INFORMATION: 3B8VL nucleotide

<400> SEQUENCE: 44
gatatcgtgc tgacccaatc tccagcttct ttggctgtgt ctctagggca gagagccacc      60
atctcctgca gagccagtga aagtgttgaa tattatggca aagtttaat gcagtggtac      120 caacagaaac aggacagcc acccaaactc ctcatctatg ctgcatccaa cgtagaatct      180
ggggtccctg ccaggtttag tggcagtggg tctgggacag acttcagcct caacatccat      240
cctgtggagg aggatgattt tgcaatgtat ttctgtcagc aaagtaggaa gattccttac      300
acgttcggag gggggaccaa gctggaaata aaa                                  333

<210> SEQ ID NO 45
<211> LENGTH: 5
<212> TYPE: PRT
<213> ORGANISM: Artificial Sequence
<220> FEATURE:
<223> OTHER INFORMATION: 3B8 HCDR1

<400> SEQUENCE: 45

Asn Tyr Ala Val Ser
1               5

<210> SEQ ID NO 46
<211> LENGTH: 14
<212> TYPE: PRT
<213> ORGANISM: Artificial Sequence
<220> FEATURE:
<223> OTHER INFORMATION: 3B8 HCDR2

<400> SEQUENCE: 46

Trp Gly Asp Gly Thr Thr Asn Tyr His Ser Ala Leu Ile Ser
1               5                   10

<210> SEQ ID NO 47
<211> LENGTH: 13
<212> TYPE: PRT
<213> ORGANISM: Artificial Sequence
<220> FEATURE:
<223> OTHER INFORMATION: 3B8 HCDR3

<400> SEQUENCE: 47

Glu Gly Asp Tyr Gly Asp Tyr Val Gly Trp Phe Ala Tyr
1               5                   10

<210> SEQ ID NO 48
<211> LENGTH: 15
<212> TYPE: PRT
<213> ORGANISM: Artificial Sequence
<220> FEATURE:
<223> OTHER INFORMATION: 3B8 LCDR1

<400> SEQUENCE: 48

Arg Ala Ser Glu Ser Val Glu Tyr Tyr Gly Thr Ser Leu Met Gln
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: 3B8 LCDR2

<400> SEQUENCE: 49

Ala Ala Ser Asn Val Glu Ser
1               5

<210> SEQ ID NO 50
<211> LENGTH: 9
<212> TYPE: PRT
<213> ORGANISM: Artificial Sequence
<220> FEATURE:
<223> OTHER INFORMATION: 3B8 LCDR3

<400> SEQUENCE: 50

Gln Gln Ser Arg Lys Ile Pro Tyr Thr
1               5

<210> SEQ ID NO 51
<211> LENGTH: 123
<212> TYPE: PRT
<213> ORGANISM: Artificial Sequence
<220> FEATURE:
<223> OTHER INFORMATION: 4G1 VH

<400> SEQUENCE: 51

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Asn Met Asn Trp Val Lys Gln Ser Lys Gly Lys Ser Leu Glu Trp Ile
        35                  40                  45

Gly Leu Ile Asn Pro Asn Tyr Ala Thr Thr Ser Tyr Asn Gln Lys Phe
    50                  55                  60

Lys Asp Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Tyr Tyr Ser Tyr Tyr Ser Tyr Gly Gly Tyr Ala Met Asp Tyr
            100                 105                 110

Trp Gly Gln Gly Thr Ser Val Thr Val Ser Ser
        115                 120

<210> SEQ ID NO 52
<211> LENGTH: 369
<212> TYPE: DNA
<213> ORGANISM: Artificial Sequence
<220> FEATURE:
<223> OTHER INFORMATION: 4G1 VH nucleotide

<400> SEQUENCE: 52
caggtccagc tgcagcagtc cggacctgag ctggtgaagc ctggcgcttc agtgaagata    60
tcatgcaagg cttctggtta ctcattcact gcctacaaca tgaactgggt gaagcagagc   120

```
aagggaaaga gccttgagtg gattggacta attaatccta actatgccac gactagttac      180
aatcagaagt tcaaggacaa ggccacattg actgtggacc aatcttccag cacagcctac      240
atgcagctca acagcctgac atctgaggac tctgcagtct attactgtgc ctactatagt      300
tactatagtt acggggggg atatgctatg gactactggg gtcaaggaac ctcagtcacc      360
gtctcctca                                                              369
```

<210> SEQ ID NO 53
<211> LENGTH: 107
<212> TYPE: PRT
<213> ORGANISM: Artificial Sequence
<220> FEATURE:
<223> OTHER INFORMATION: 4G1VL

<400> SEQUENCE: 53

```
Asp Ile Leu Leu Thr Gln Ser Pro Ala Ile Leu Ser Val Ser Pro Gly
1               5                   10                  15
Glu Arg Val Ser Phe Ser Cys Arg Ala Ser Gln Ser Ile Gly Thr Ser
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Ile Leu Ser Ile Asn Ser Val Glu Ser
65                  70                  75                  80
Glu Asp Ile Ala Asp Tyr Tyr Cys Gln Gln Ser Asn Ser Trp Pro Trp
                85                  90                  95
Thr Phe Gly Gly Gly Thr Arg Leu Glu Ile Lys
            100                 105
```

<210> SEQ ID NO 54
<211> LENGTH: 321
<212> TYPE: DNA
<213> ORGANISM: Artificial Sequence
<220> FEATURE:
<223> OTHER INFORMATION: 4G1VL nucleotide

<400> SEQUENCE: 54

```
gatatcttgc tgacccaatc tccagccatc ctgtctgtga gtccaggaga aagagtcagt      60
ttttcctgca gggccagtca gagcattggc acaagcatac actggtatca gcaagaaaca     120
aatgggtctc caaggcttct cataaagtat gcttctgagt ctatctctgg gatcccttcc     180
aggtttagtg gcagtggatc aggacagat tttattctta gcatcaacag tgtggagtct     240
gaggatattg ctgattatta ctgtcagcaa agtaatagct ggccgtggac gttcggtgga     300
ggcaccaggc tggaaatcaa a                                               321
```

<210> SEQ ID NO 55
<211> LENGTH: 5
<212> TYPE: PRT
<213> ORGANISM: Artificial Sequence
<220> FEATURE:
<223> OTHER INFORMATION: 4G1 HCDR1

<400> SEQUENCE: 55

```
Ala Tyr Asn Met Asn
1               5
```

<210> SEQ ID NO 56
<211> LENGTH: 17

```
<212> TYPE: PRT
<213> ORGANISM: Artificial Sequence
<220> FEATURE:
<223> OTHER INFORMATION: 4G1 HCDR2

<400> SEQUENCE: 56

Leu Ile Asn Pro Asn Tyr Ala Thr Thr Ser Tyr Asn Gln Lys Phe Lys
1               5                   10                  15

Asp

<210> SEQ ID NO 57
<211> LENGTH: 14
<212> TYPE: PRT
<213> ORGANISM: Artificial Sequence
<220> FEATURE:
<223> OTHER INFORMATION: 4G1 HCDR3

<400> SEQUENCE: 57

Tyr Ser Tyr Tyr Ser Tyr Gly Gly Gly Tyr Ala Met Asp Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: 4G1 LCDR1

<400> SEQUENCE: 58

Arg Ala Ser Gln Ser Ile Gly Thr Ser Ile His
1               5                   10

<210> SEQ ID NO 59
<211> LENGTH: 7
<212> TYPE: PRT
<213> ORGANISM: Artificial Sequence
<220> FEATURE:
<223> OTHER INFORMATION: 4G1 LCDR2

<400> SEQUENCE: 59

Tyr Ala Ser Glu Ser Ile Ser
1               5

<210> SEQ ID NO 60
<211> LENGTH: 9
<212> TYPE: PRT
<213> ORGANISM: Artificial Sequence
<220> FEATURE:
<223> OTHER INFORMATION: 4G1 LCDR3

<400> SEQUENCE: 60

Gln Gln Ser Asn Ser Trp Pro Trp Thr
1               5

<210> SEQ ID NO 61
<211> LENGTH: 121
<212> TYPE: PRT
<213> ORGANISM: Artificial Sequence
<220> FEATURE:
<223> OTHER INFORMATION: 4H3 VH

<400> SEQUENCE: 61

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30
```

Asn Ile Asn Trp Val Lys Gln Thr Asn Gly Lys Ser Leu Glu Trp Ile
            35                  40                  45

Gly Ile Ile Asn Pro Asn Tyr Gly Thr Thr Ser Tyr Asn Gln Lys Phe
        50                  55                  60

Lys Gly Lys Ala Thr Leu Thr Val Asp Gln Ser Ser Thr Ala Tyr
 65                  70                  75                  80

Met Gln Leu Asn Ser Leu Thr Ser Glu Asp Ser Ala Val Tyr Tyr Cys
                85                  90                  95

Ala Arg Arg Asn Gly Asp Tyr Val Gly Tyr Ala Met Asp Ser Trp Gly
                100                 105                 110

Gln Gly Thr Ser Val Thr Val Ser Ser
        115                 120

<210> SEQ ID NO 62
<211> LENGTH: 363
<212> TYPE: DNA
<213> ORGANISM: Artificial Sequence
<220> FEATURE:
<223> OTHER INFORMATION: 4H3 VH nucleotide

<400> SEQUENCE: 62
caggtgcagc tgcagcagtc tggacctgag ctggtgaagc ctggcgcttc agtgaagata      60
tcctgcaagg cttctggtta ctcattcact gcctacaaca ttaactgggt gaagcagacc     120
aatggaaaga gccttgagtg gattggaata attaatccta actatggtac tactagttac     180
aaccagaagt tcaagggcaa ggccacattg actgtagacc aatcttccag tacagcctac     240
atgcagctca acagcctgac atctgaggac tctgcagtct attactgtgc aagacggaat     300
ggtgactacg tgggatatgc tatggactcc tggggtcaag gaacctcagt caccgtctcc     360
tca                                                                   363

<210> SEQ ID NO 63
<211> LENGTH: 107
<212> TYPE: PRT
<213> ORGANISM: Artificial Sequence
<220> FEATURE:
<223> OTHER INFORMATION: 4H3VL

<400> SEQUENCE: 63

Asp Ile Val Leu Thr Gln Ser Pro Ala Ile Leu Ser Val Ser Pro Gly
 1               5                  10                  15

Glu Arg Val Ser Phe Ser Cys Arg Ala Ser Gln Ser Ile Gly Thr Ser
                20                  25                  30

Met His Trp Tyr Gln Gln Arg Lys Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Thr Asn Asn Trp Pro Trp
                85                  90                  95

Thr Phe Gly Gly Gly Thr Lys Leu Glu Phe Lys
                100                 105

<210> SEQ ID NO 64
<211> LENGTH: 321
<212> TYPE: DNA
<213> ORGANISM: Artificial Sequence
<220> FEATURE:
<223> OTHER INFORMATION: 4H3VL nucleotide

<400> SEQUENCE: 64

```
gatatcgttc tcacccagtc tccagccatc ctctctgtga gtccaggaga aagagtcagt      60
ttctcctgca gggccagtca gagcattggc acaagcatgc actggtatca gcaaagaaaa     120
aatggttctc caaggcttct cataaagtat gcttctgagt ctatctctgg gatcccttcc     180
aggtttagtg gcagtggatc agggacagat tttactctta gcatcaacag tgtggagtct     240
gaggatattg cagattatta ctgtcaacaa actaataact ggccgtggac gttcggtgga     300
ggcaccaagc tggaattcaa a                                                321
```

<210> SEQ ID NO 65
<211> LENGTH: 5
<212> TYPE: PRT
<213> ORGANISM: Artificial Sequence
<220> FEATURE:
<223> OTHER INFORMATION: 4H3 HCDR1

<400> SEQUENCE: 65

Ala Tyr Asn Ile Asn
1               5

<210> SEQ ID NO 66
<211> LENGTH: 17
<212> TYPE: PRT
<213> ORGANISM: Artificial Sequence
<220> FEATURE:
<223> OTHER INFORMATION: 4H3 HCDR2

<400> SEQUENCE: 66

Ile Ile Asn Pro Asn Tyr Gly Thr Thr Ser Tyr Asn Gln Lys Phe Lys
1               5                   10                  15
Gly

<210> SEQ ID NO 67
<211> LENGTH: 12
<212> TYPE: PRT
<213> ORGANISM: Artificial Sequence
<220> FEATURE:
<223> OTHER INFORMATION: 4H3 HCDR3

<400> SEQUENCE: 67

Arg Asn Gly Asp Tyr Val Gly Tyr Ala Met Asp Ser
1               5                   10

<210> SEQ ID NO 68
<211> LENGTH: 11
<212> TYPE: PRT
<213> ORGANISM: Artificial Sequence
<220> FEATURE:
<223> OTHER INFORMATION: 4H3 LCDR1

<400> SEQUENCE: 68

Arg Ala Ser Gln Ser Ile Gly Thr Ser Met His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: 4H3 LCDR2

<400> SEQUENCE: 69

Tyr Ala Ser Glu Ser Ile Ser
1               5

<210> SEQ ID NO 70
<211> LENGTH: 9
<212> TYPE: PRT
<213> ORGANISM: Artificial Sequence
<220> FEATURE:
<223> OTHER INFORMATION: 4H3 LCDR3

<400> SEQUENCE: 70

Gln Gln Thr Asn Asn Trp Pro Trp Thr
1               5

<210> SEQ ID NO 71
<211> LENGTH: 117
<212> TYPE: PRT
<213> ORGANISM: Artificial Sequence
<220> FEATURE:
<223> OTHER INFORMATION: 2G3 VH

<400> SEQUENCE: 71

Glu Val Lys Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Ile Arg Gln Thr Pro Glu Lys Arg Leu Glu Trp Val
        35                  40                  45

Ala Ala Ile Ser Asp Gly Gly Thr Tyr Thr Tyr Tyr Pro Asn Asn Val
    50                  55                  60

Lys Gly Arg Phe Thr Ile Ser Arg Asp Asp Ala Lys Asn Asn Leu Tyr
65                  70                  75                  80

Leu Gln Met Ser His Leu Lys Ser Glu Asp Thr Ala Met Tyr Tyr Cys
                85                  90                  95

Val Arg Asn Arg Gly Gly Pro Phe Asp Tyr Trp Gly Gln Gly Thr Thr
            100                 105                 110

Leu Thr Val Ser Ser
        115

<210> SEQ ID NO 72
<211> LENGTH: 351
<212> TYPE: DNA
<213> ORGANISM: Artificial Sequence
<220> FEATURE:
<223> OTHER INFORMATION: 2G3 VH nucleotide

<400> SEQUENCE: 72
gaggtgaagc tgcaggagtc tgggggaggc ttagtgaagc ctggagggtc cctgaaactc      60
tcctgtgcag cctctggatt cactttcagt agctttgcca tgtcttggat tcgccagact     120
ccggaaaaga ggctggagtg gtcgcgggcc attagtgatg gtggtactta cacctactat     180
ccaaacaatg taaagggccg attcaccatc tccagagacg atgccaagaa taacctgtac     240
ctgcaaatga gtcatctgaa gtctgaggac acagccatgt attactgtgt aagaaatagg     300
gggggaccct ttgactactg gggccaaggc accactctca cagtctcctc a              351

<210> SEQ ID NO 73
<211> LENGTH: 106
<212> TYPE: PRT
<213> ORGANISM: Artificial Sequence

<220> FEATURE:
<223> OTHER INFORMATION: 2G3VL

<400> SEQUENCE: 73

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Ala Gly Thr Lys Leu Glu Leu Lys
            100                 105

<210> SEQ ID NO 74
<211> LENGTH: 318
<212> TYPE: DNA
<213> ORGANISM: Artificial Sequence
<220> FEATURE:
<223> OTHER INFORMATION: 2G3VL nucleotide

<400> SEQUENCE: 74
gatatcgtgc tcactcagtc tccagcaatc atgtctgcat ctccagggga gaaggtcacc      60
atgacctgca gtgccagctc aagtgtaagt tacatgaact ggtaccagca gaagtcaggc     120
acctccccca aaagatggat ttatgacaca tccaaactgg cttctggagt ccctgttcgc     180
ttcagtggca gtgggtctgg gacctcttac tctctcacaa tcagcagcat ggaggctgaa     240
gatgctgcca cttattactg ccagcagtgg aatagtaacc cacccacgtt cggtgctggg     300
accaagctgg agctgaaa                                                    318

<210> SEQ ID NO 75
<211> LENGTH: 5
<212> TYPE: PRT
<213> ORGANISM: Artificial Sequence
<220> FEATURE:
<223> OTHER INFORMATION: 2G3 HCDR1

<400> SEQUENCE: 75

Ser Phe Ala Met Ser
1               5

<210> SEQ ID NO 76
<211> LENGTH: 17
<212> TYPE: PRT
<213> ORGANISM: Artificial Sequence
<220> FEATURE:
<223> OTHER INFORMATION: 2G3 HCDR2

<400> SEQUENCE: 76

Ala Ile Ser Asp Gly Gly Thr Tyr Thr Tyr Tyr Pro Asn Asn Val Lys
1               5                   10                  15

Gly

<210> SEQ ID NO 77
<211> LENGTH: 8

```
<212> TYPE: PRT
<213> ORGANISM: Artificial Sequence
<220> FEATURE:
<223> OTHER INFORMATION: 2G3 HCDR3

<400> SEQUENCE: 77

Asn Arg Gly Gly Pro Phe Asp Tyr
1               5

<210> SEQ ID NO 78
<211> LENGTH: 10
<212> TYPE: PRT
<213> ORGANISM: Artificial Sequence
<220> FEATURE:
<223> OTHER INFORMATION: 2G3 LCDR1

<400> SEQUENCE: 78

Ser Ala Ser Ser Ser Val Ser Tyr Met Asn
1               5                   10

<210> SEQ ID NO 79
<211> LENGTH: 7
<212> TYPE: PRT
<213> ORGANISM: Artificial Sequence
<220> FEATURE:
<223> OTHER INFORMATION: 2G3 LCDR2

<400> SEQUENCE: 79

Asp Thr Ser Lys Leu Ala Ser
1               5

<210> SEQ ID NO 80
<211> LENGTH: 9
<212> TYPE: PRT
<213> ORGANISM: Artificial Sequence
<220> FEATURE:
<223> OTHER INFORMATION: 2G3 LCDR3

<400> SEQUENCE: 80

Gln Gln Trp Asn Ser Asn Pro Pro Thr
1               5

<210> SEQ ID NO 81
<211> LENGTH: 117
<212> TYPE: PRT
<213> ORGANISM: Artificial Sequence
<220> FEATURE:
<223> OTHER INFORMATION: 2F11 VH

<400> SEQUENCE: 81

Glu Val Gln Leu Gln Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ile Ile Gly Asp Gly Asp Thr Tyr Thr Tyr Pro Asp Ser Val
    50                  55                  60

Lys Gly Arg Phe Thr Val Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110
```

<210> SEQ ID NO 82
<211> LENGTH: 351
<212> TYPE: DNA
<213> ORGANISM: Artificial Sequence
<220> FEATURE:
<223> OTHER INFORMATION: 2F11 VH nucleotide

<400> SEQUENCE: 82

```
gaggtgcagc tgcaggagtc tgggggagac ttagtgaagc ctggagggtc cctgaaactc      60
tcctgtgcag cctctggatt cactttcagt agctatgcca tgtcttgggt tcgccagact     120
ccggaaaaga ggctgagtg gtcgcaatc attggtgatg gtgatactta cacctactat      180
ccagacagtg taaagggccg attcaccgtc tccagagaca atgccaagaa caacctctac     240
ctgcaaatga gccatctgaa gtctgaggac acagccatgt attactgtgt aagaactagg     300
gggggaccct tgactactg ggccaaggc accactctca cagtctcctc a              351
```

<210> SEQ ID NO 83
<211> LENGTH: 106
<212> TYPE: PRT
<213> ORGANISM: Artificial Sequence
<220> FEATURE:
<223> OTHER INFORMATION: 2F11VL

<400> SEQUENCE: 83

Asp Ile Val Leu Thr Gln Thr Pro Ala Leu Met Ser Ala Ser Pro Gly
1               5                   10                  15

Glu Lys Val Thr Met Thr Cys Ser Ala Ser Ser Ser Val Gly Ser Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Ile Pro Pro Thr
                85                  90                  95

Phe Gly Ala Gly Thr Thr Leu Glu Leu Lys
            100                 105

<210> SEQ ID NO 84
<211> LENGTH: 318
<212> TYPE: DNA
<213> ORGANISM: Artificial Sequence
<220> FEATURE:
<223> OTHER INFORMATION: 2F11VL nucleotide

<400> SEQUENCE: 84

```
gatatcgtgc tcacccaaac tccagcactc atgtctgcat ctccagggga agtgtcacc      60 atgacctgca gtgccagctc aagtgtaggt tccatgcact ggtaccagca gaagtcaggc     120
acctccccca aagatggat ttatgacaca tccaaactgg cttctggagt ccctgctcgc      180
ttcagtggca gtgggtctgg gacctcttac tctctcacaa tcagcagcat ggaggctgaa     240
gatgctgcca cttattactg ccaacagtgg agtagtatcc cacccacgtt cggtgctggg     300
accacgctgg agctgaaa                                                    318
```

<210> SEQ ID NO 85
<211> LENGTH: 5
<212> TYPE: PRT
<213> ORGANISM: Artificial Sequence
<220> FEATURE:
<223> OTHER INFORMATION: 2F11 HCDR1

<400> SEQUENCE: 85

Ser Tyr Ala Met Ser
1               5

<210> SEQ ID NO 86
<211> LENGTH: 17
<212> TYPE: PRT
<213> ORGANISM: Artificial Sequence
<220> FEATURE:
<223> OTHER INFORMATION: 2F11 HCDR2

<400> SEQUENCE: 86

Ile Ile Gly Asp Gly Asp Thr Tyr Thr Tyr Tyr Pro Asp Ser Val Lys
1               5                   10                  15

Gly

<210> SEQ ID NO 87
<211> LENGTH: 8
<212> TYPE: PRT
<213> ORGANISM: Artificial Sequence
<220> FEATURE:
<223> OTHER INFORMATION: 2F11 HCDR3

<400> SEQUENCE: 87

Thr Arg Gly Gly Pro Phe Asp Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: 2F11 LCDR1

<400> SEQUENCE: 88

Ser Ala Ser Ser Ser Val Gly Ser Met His
1               5                   10

<210> SEQ ID NO 89
<211> LENGTH: 7
<212> TYPE: PRT
<213> ORGANISM: Artificial Sequence
<220> FEATURE:
<223> OTHER INFORMATION: 2F11 LCDR2

<400> SEQUENCE: 89

Asp Thr Ser Lys Leu Ala Ser
1               5

<210> SEQ ID NO 90
<211> LENGTH: 9
<212> TYPE: PRT
<213> ORGANISM: Artificial Sequence
<220> FEATURE:
<223> OTHER INFORMATION: 2F11 LCDR3

<400> SEQUENCE: 90

Gln Gln Trp Ser Ser Ile Pro Pro Thr
1               5

<210> SEQ ID NO 91
<211> LENGTH: 106
<212> TYPE: PRT
<213> ORGANISM: Artificial Sequence
<220> FEATURE:
<223> OTHER INFORMATION: 16647VL

<400> SEQUENCE: 91

Glu Ile Leu Leu Thr Gln Ser Pro Ala Phe Met Ser Ala Thr Pro Gly
1               5                   10                  15

Glu Lys Val Thr Ile Thr Cys Ser Ala Ser Ser Ser Val Gly Ser Met
            20                  25                  30

His Trp Tyr Gln Gln Lys Ser Gly Gln Ser Pro Arg Arg Leu Ile Tyr
        35                  40                  45

Asp Thr Ser Lys Leu Ala Ser Gly Val Pro Asp Arg Phe Ser Gly Ser
    50                  55                  60

Gly Ser Gly Thr Asp Tyr Thr Leu Thr Ile Ser Ser Leu Glu Ala Glu
65                  70                  75                  80

Asp Ala Ala Thr Tyr Tyr Cys Gln Gln Trp Ser Ser Ile Pro Pro Thr
                85                  90                  95

Phe Gly Ala Gly Thr Thr Leu Glu Leu Lys
            100                 105

<210> SEQ ID NO 92
<211> LENGTH: 318
<212> TYPE: DNA
<213> ORGANISM: Artificial Sequence
<220> FEATURE:
<223> OTHER INFORMATION: 16647VL nucleotide

<400> SEQUENCE: 92
gagatcctgc tgacccagag ccctgccttt atgagcgcca ccccggcga aggtgacc        60 atcacctgca gcgccagcag cagcgtgggc agcatgcact ggtatcaaca aaagagcggc   120
cagagcccca ggaggctgat ctacgacacc agcaagctgg ccagcggcgt gcctgacagg   180
ttctctggta gcggcagcgg caccgactac accctgacca tcagcagcct ggaggccgaa   240
gacgccgcca cctactactg ccagcagtgg agcagcatcc ctcccacctt cggcgctgga   300
accaccctgg agctgaag                                                 318

<210> SEQ ID NO 93
<211> LENGTH: 117
<212> TYPE: PRT
<213> ORGANISM: Artificial Sequence
<220> FEATURE:
<223> OTHER INFORMATION: 9419VH

<400> SEQUENCE: 93

Glu Val His Leu Gln Glu Ser Gly Gly Ala Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Glu Lys Gly Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Ser Asn Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 94
<211> LENGTH: 351
<212> TYPE: DNA
<213> ORGANISM: Artificial Sequence
<220> FEATURE:
<223> OTHER INFORMATION: 9419VH nucleotide

<400> SEQUENCE: 94
gaggtgcacc tgcaggagtc tggtggagcc ctggtgaagc ccggaggaag cctgagactg      60
agctgcgccg ccagcggctt caccttcagc agctacgcca tgagctgggt gagacaggcc     120
cctgagaagg gcctggagtg ggtggccatc atcggcgacg gcgacaccta cacctactac     180
cccgacagcg tgaagggcag gttcaccatc agcagggaca acgctaagaa caccctgtac     240
ctgcagatga gcaacctgaa gagcgaggac accgccatgt actactgcgt gaggaccaga     300
ggcggcccct tcgactactg gggccagggc accaccctga cagtgagcag c             351

<210> SEQ ID NO 95
<211> LENGTH: 117
<212> TYPE: PRT
<213> ORGANISM: Artificial Sequence
<220> FEATURE:
<223> OTHER INFORMATION: d9419VH

<400> SEQUENCE: 95

Glu Val His Leu Gln Glu Ser Gly Gly Ala Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Lys Pro Glu Lys Asn Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Asp Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 96
<211> LENGTH: 351
<212> TYPE: DNA
<213> ORGANISM: Artificial Sequence
<220> FEATURE:
<223> OTHER INFORMATION: d9419VH nucleotide

<400> SEQUENCE: 96
gaggtgcatc tgcaggagag cggcggagcc ctggtgaaac ctggcggaag cctgagactg      60
agctgcgccg cctccggctt caccttcagc tcctacgcca tgagctgggt gaggcagaag     120
```

```
cccgagaaga acctggagtg ggtggccatc atcggcgacg cgacaccta cacctactac    180 cccgacagcg tgaagggcag gttcaccatc agcagggaca acgccaagaa caccctgtac    240
ctgcagatga gcgacctgaa gagcgaggac accgccatgt actactgcgt gaggaccagg    300
ggcggccctt tcgactattg ggccagggc acaaccctga ccgtgagcag c              351
```

<210> SEQ ID NO 97
<211> LENGTH: 117
<212> TYPE: PRT
<213> ORGANISM: Artificial Sequence
<220> FEATURE:
<223> OTHER INFORMATION: 9424VH

<400> SEQUENCE: 97

```
Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Glu Lys Gly Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115
```

<210> SEQ ID NO 98
<211> LENGTH: 351
<212> TYPE: DNA
<213> ORGANISM: Artificial Sequence
<220> FEATURE:
<223> OTHER INFORMATION: 9424VH nucleotide

<400> SEQUENCE: 98

```
gaggtgcacc tgcaggagtc tggtggaggc ctggtgaagc ccggaggaag cctgagactg    60
agctgcgccg ccagcggctt caccttcagc agctacgcca tgagctgggt gagacagacc   120
cctgagaagg gcctggagtg gtggccatc atcggcgacg cgacaccta cacctactac    180 cccgacagcg tgaagggcag gttcaccatc agcagggaca acgctaagaa caccctgtac   240
ctgcagatga acagcctgaa gagcgaggac accgccatgt actactgcgt gaggaccaga   300
ggcggccctt tcgactactg ggccagggc accaccctga cagtgagcag c              351
```

<210> SEQ ID NO 99
<211> LENGTH: 117
<212> TYPE: PRT
<213> ORGANISM: Artificial Sequence
<220> FEATURE:
<223> OTHER INFORMATION: d9424VH

<400> SEQUENCE: 99

```
Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Thr Pro Glu Lys Asn Leu Glu Trp Val
        35                  40                  45

Ala Ile Ile Gly Asp Gly Asp Thr Tyr Thr Tyr Tyr Pro Asp Ser Val
50                      55                  60

Lys Gly Arg Phe Thr Ile Ser Arg Asp Asn Ala Lys Asn Thr Leu Tyr
65                  70                  75                  80

Leu Gln Met Asn Asp Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 100
<211> LENGTH: 351
<212> TYPE: DNA
<213> ORGANISM: Artificial Sequence
<220> FEATURE:
<223> OTHER INFORMATION: d9424 nucleotide

<400> SEQUENCE: 100
gaggtgcatc tgcaggagag cggcggaggc ctggtgaaac ctggcggaag cctgagactg      60
agctgcgccg cctccggctt caccttcagc tcctacgcca tgagctgggt gaggcagacg     120
cccgagaaga acctggagtg ggtggccatc atcggcgacg gcgacaccta cacctactac     180
cccgacagcg tgaagggcag gttcaccatc agcagggaca cgccaagaa caccctgtac     240 ctgcagatga acgacctgaa gagcgaggac accgccatgt actactgcgt gaggaccagg     300
ggcggccctt tcgactattg gggccagggc acaaccctga ccgtgagcag c              351

<210> SEQ ID NO 101
<211> LENGTH: 117
<212> TYPE: PRT
<213> ORGANISM: Artificial Sequence
<220> FEATURE:
<223> OTHER INFORMATION: 12674VH

<400> SEQUENCE: 101

Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ile Ile Gly Asp Gly Asp Thr Tyr Thr Tyr Tyr Pro Asp Ser Val
50                      55                  60

Lys Gly Arg Phe Thr Ile Ser Arg Asp Asn Ser Lys Asn Arg Leu Tyr
65                  70                  75                  80

Leu Gln Met Asn Ser Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 102
<211> LENGTH: 351
<212> TYPE: DNA

<213> ORGANISM: Artificial Sequence
<220> FEATURE:
<223> OTHER INFORMATION: 12674VH nucleotide

<400> SEQUENCE: 102

```
gaggtgcacc tgcaagagag cggaggaggc ctggtgaaac ctggcggcag cctgaggctg    60
agctgtgctg ccagcggctt caccttctcc agctacgcca tgagctgggt gaggcaggcg   120
cccggcaaag gcctggagtg ggtggccatc atcggcgacg gcgacaccta cacctactac   180
cccgacagcg tgaagggcag gttcaccatc agcagggaca cagcaagaa caggctgtac    240
ctgcagatga acagcctgaa gagcgaggac accgccatgt actactgcgt gaggaccaga   300
ggcggcccctt tcgactactg gggccaggga accaccctga ccgtgagcag c           351
```

<210> SEQ ID NO 103
<211> LENGTH: 117
<212> TYPE: PRT
<213> ORGANISM: Artificial Sequence
<220> FEATURE:
<223> OTHER INFORMATION: d12674VH

<400> SEQUENCE: 103

```
Glu Val His Leu Gln Glu Ser Gly Gly Gly Leu Val Lys Pro Gly Gly
 1               5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ala Ile Ile Gly Asp Gly Asp Thr Tyr Thr Tyr Tyr Pro Asp Ser Val
    50                  55                  60
Lys Gly Arg Phe Thr Ile Ser Arg Asp Asn Ser Lys Asn Arg Leu Tyr
65                  70                  75                  80
Leu Gln Met Asn Asp Leu Lys Ser Glu Asp Thr Ala Met Tyr Tyr Cys
                85                  90                  95
Val Arg Thr Arg Gly Gly Pro Phe Asp Tyr Trp Gly Gln Gly Thr Thr
            100                 105                 110
Leu Thr Val Ser Ser
        115
```

<210> SEQ ID NO 104
<211> LENGTH: 351
<212> TYPE: DNA
<213> ORGANISM: Artificial Sequence
<220> FEATURE:
<223> OTHER INFORMATION: d12674 nucleotide

<400> SEQUENCE: 104

```
gaggtgcacc tgcaagagag cggaggcgga ctggtgaaac ctggcggcag cctgagactg    60
agctgtgccg ccagcggctt caccttcagc agctacgcca tgagctgggt gaggcaggcc   120
cccggtaagg gcctggagtg ggtggccatc atcggcgacg gcgacaccta cacctactac   180
cccgacagcg tgaagggcag attcaccatc agcagggaca actccaagaa caggctgtac    240
ctgcagatga acgacctgaa gagcgaggac accgccatgt actactgcgt gaggaccagg   300
ggcggcccctt tcgattactg gggccagggc acaaccctga ccgtgagcag c           351
```

<210> SEQ ID NO 105
<211> LENGTH: 117
<212> TYPE: PRT
<213> ORGANISM: Artificial Sequence

```
<220> FEATURE:
<223> OTHER INFORMATION: 12996VH

<400> SEQUENCE: 105

Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Glu Lys Gly Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 106
<211> LENGTH: 351
<212> TYPE: DNA
<213> ORGANISM: Artificial Sequence
<220> FEATURE:
<223> OTHER INFORMATION: 12996VH nucleotide

<400> SEQUENCE: 106
gaggtgcacc tgcaagagag cggaggaggc ctggtgaaac ctggcggcag cctgaggctg      60
agctgtgctg ccagcggctt caccttctcc agctacgcca tgagctgggt gaggcaggcg     120
cccgagaaag gcctggagtg ggtggccatc atcggcgacg gcgacaccta cacctactac     180
cccgacagcg tgaagggcag gttcaccatc agcagggaca cagcaagaa caggctgtac      240 ctgcagatga acagcctgaa gagcgaggac accgccatgt actactgcgt gaggaccaga     300 ggcggcccctt tcgactactg gggccaggga accaccctga ccgtgagcag c             351

<210> SEQ ID NO 107
<211> LENGTH: 117
<212> TYPE: PRT
<213> ORGANISM: Artificial Sequence
<220> FEATURE:
<223> OTHER INFORMATION: d12996VH

<400> SEQUENCE: 107

Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Glu Pro Glu Lys Asn Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Asp Leu Lys Ser Glu Asp Thr Ala Met Tyr Tyr Cys
                85                  90                  95
```

```
Val Arg Thr Arg Gly Gly Pro Phe Asp Tyr Trp Gln Gly Thr Thr
            100                 105                 110

Leu Thr Val Ser Ser
        115

<210> SEQ ID NO 108
<211> LENGTH: 351
<212> TYPE: DNA
<213> ORGANISM: Artificial Sequence
<220> FEATURE:
<223> OTHER INFORMATION: d12996VH nucleotide

<400> SEQUENCE: 108
gaggtgcacc tgcaagagag cggaggcgga ctggtgaaac ctggcggcag cctgagactg     60
agctgtgccg ccagcggctt caccttcagc agctacgcca tgagctgggt gaggcaggaa    120
cccgagaaga acctggagtg ggtggccatc atcggcgacg gcgacaccta cacctactac    180
cccgacagcg tgaagggcag attcaccatc agcagggaca ctccaagaa caggctgtac     240 ctgcagatga acgacctgaa gagcgaggac accgccatgt actactgcgt gaggaccagg    300 ggcggcccctt tcgattactg gggccagggc acaaccctga ccgtgagcag c             351

<210> SEQ ID NO 109
<211> LENGTH: 117
<212> TYPE: PRT
<213> ORGANISM: Artificial Sequence
<220> FEATURE:
<223> OTHER INFORMATION: 14822VH

<400> SEQUENCE: 109

Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Met Pro Gly Lys Gly Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115

<210> SEQ ID NO 110
<211> LENGTH: 351
<212> TYPE: DNA
<213> ORGANISM: Artificial Sequence
<220> FEATURE:
<223> OTHER INFORMATION: 14822VH nucleotide

<400> SEQUENCE: 110
gaggtgcacc tgcaagagag cggaggaggc ctggtgaaac ctggcggcag cctgaggctg     60
agctgtgctg ccagcggctt caccttctcc agctacgcca tgagctgggt gaggcagatg    120
cccggcaaag gcctggagtg ggtggccatc atcggcgacg gcgacaccta cacctactac    180
cccgacagcg tgaagggcag gttcaccatc agcagggaca acagcaagaa cacgctgtac    240
```

```
ctgcagatga acagcctgaa gagcgaggac accgccatgt actactgcgt gaggaccaga      300
ggcggcccct tcgactactg gggccaggga accaccctga ccgtgagcag c              351
```

<210> SEQ ID NO 111
<211> LENGTH: 117
<212> TYPE: PRT
<213> ORGANISM: Artificial Sequence
<220> FEATURE:
<223> OTHER INFORMATION: d14882VH

<400> SEQUENCE: 111

```
Glu Val His Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Asp Lys Gly Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asp Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser
        115
```

<210> SEQ ID NO 112
<211> LENGTH: 351
<212> TYPE: DNA
<213> ORGANISM: Artificial Sequence
<220> FEATURE:
<223> OTHER INFORMATION: d14882VH nucleotide

<400> SEQUENCE: 112

```
gaggtgcacc tgcaagagag cggaggcgga ctggtgaaac ctggcggcag cctgagactg      60
agctgtgccg ccagcggctt caccttcagc agctacgcca tgagctgggt gaggcagacc      120
cccgataagg gcctggagtg gtggccatc atcggcgacg gcgacaccta cacctactac      180
cccgacagcg tgaagggcag attcaccatc agcagggaca actccaagaa cacgctgtac      240
ctgcagatga cgacctgaa gagcgaggac accgccatgt actactgcgt gaggaccagg      300
ggcggcccct tcgattactg gggccagggc acaaccctga ccgtgagcag c              351
```

<210> SEQ ID NO 113
<211> LENGTH: 117
<212> TYPE: PRT
<213> ORGANISM: Artificial Sequence
<220> FEATURE:
<223> OTHER INFORMATION: 16647VH

<400> SEQUENCE: 113

```
Gln Val Glu Leu Arg Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Met Pro Gly Lys Gly Leu Glu Trp Val
        35                  40                  45
```

```
Ala Ile Ile Gly Asp Gly Asp Thr Tyr Thr Tyr Tyr Pro Asp Ser Val
         50                  55                  60

Lys Gly Arg Phe Thr Ile Ser Arg Asp Asn Ser Lys Asn Arg Leu Tyr
 65                  70                  75                  80

Leu Gln Met Asn Ser Leu Lys Ser Glu Asp Thr Ala Met Tyr Tyr Cys
                 85                  90                  95

Val Arg Thr Arg Gly Gly Pro Phe Asp Tyr Trp Gly Gln Gly Thr Thr
                100                 105                 110

Leu Thr Val Ser Ser
        115
```

<210> SEQ ID NO 114
<211> LENGTH: 351
<212> TYPE: DNA
<213> ORGANISM: Artificial Sequence
<220> FEATURE:
<223> OTHER INFORMATION: 16647VH nucleotide

<400> SEQUENCE: 114

```
caggtggagc tgagagagag cggaggaggc ctggtgaaac ctggcggcag cctgaggctg      60
agctgtgctg ccagcggctt caccttctcc agctacgcca tgagctgggt gaggcagatg     120
cccggcaaag gcctggagtg ggtggccatc atcggcgacg gcgacaccta cacctactac     180
cccgacagcg tgaagggcag gttcaccatc agcagggaca cagcaagaa caggctgtac      240
ctgcagatga acagcctgaa gagcgaggac accgccatgt actactgcgt gaggaccaga     300
ggcggcccct tcgactactg gggccaggga accaccctga ccgtgagcag c              351
```

<210> SEQ ID NO 115
<211> LENGTH: 117
<212> TYPE: PRT
<213> ORGANISM: Artificial Sequence
<220> FEATURE:
<223> OTHER INFORMATION: d16647VH

<400> SEQUENCE: 115

```
Gln Val Glu Leu Arg Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Thr Pro Asp Lys Gly Leu Glu Trp Val
         35                  40                  45

Ala Ile Ile Gly Asp Gly Asp Thr Tyr Thr Tyr Tyr Pro Asp Ser Val
         50                  55                  60

Lys Gly Arg Phe Thr Ile Ser Arg Asp Asn Ser Lys Asn Arg Leu Tyr
 65                  70                  75                  80

Leu Gln Met Asn Asp Leu Lys Ser Glu Asp Thr Ala Met Tyr Tyr Cys
                 85                  90                  95

Val Arg Thr Arg Gly Gly Pro Phe Asp Tyr Trp Gly Gln Gly Thr Thr
                100                 105                 110

Leu Thr Val Ser Ser
        115
```

<210> SEQ ID NO 116
<211> LENGTH: 351
<212> TYPE: DNA
<213> ORGANISM: Artificial Sequence
<220> FEATURE:
<223> OTHER INFORMATION: d16647VH nucleotide

<400> SEQUENCE: 116

```
caggtggagc tgagggagag cggaggcgga ctggtgaaac ctggcggcag cctgagactg      60
agctgtgccg ccagcggctt caccttcagc agctacgcca tgagctgggt gaggcagacc     120
cccgataagg gcctggagtg ggtggccatc atcggcgacg gcgacaccta cacctactac     180
cccgacagcg tgaagggcag attcaccatc agcagggaca actccaagaa caggctgtac     240
ctgcagatga acgacctgaa gagcgaggac accgccatgt actactgcgt gaggaccagg     300
ggcggccctt tcgattactg gggccagggc acaaccctga ccgtgagcag c              351
```

<210> SEQ ID NO 117
<211> LENGTH: 214
<212> TYPE: PRT
<213> ORGANISM: Artificial Sequence
<220> FEATURE:
<223> OTHER INFORMATION: m2E7light chain

<400> SEQUENCE: 117

```
Asp Ile Val Met Thr Gln Ser Thr Ala Ile Met Ser Ala Ser Pro Gly
1               5                   10                  15
Glu Lys Val Thr Met Thr Cys Ser Ala Ser Ser Ser Val Ser Tyr Met
            20                  25                  30
His Trp Tyr Gln Gln Lys Ser Gly Thr Ser Pro Arg Arg Trp Ile Tyr
        35                  40                  45
Asp Thr Ser Arg Leu Ala Ser Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Asn Thr Pro Pro Phe
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 118
<211> LENGTH: 446
<212> TYPE: PRT
<213> ORGANISM: Artificial Sequence
<220> FEATURE:
<223> OTHER INFORMATION: m2E7 heavy chain

<400> SEQUENCE: 118

```
Glu Val Gln Leu Gln Glu Ser Gly Pro Glu Leu Lys Lys Pro Gly Glu
1               5                   10                  15
```

```
Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Gln Trp Met
        35                  40                  45

Gly Trp Ile Asn Thr Asn Ser Gly Val Pro Thr Tyr Val Glu Asp Phe
    50                  55                  60

Lys Gly Arg Phe Ala Phe Ser Leu Glu Ser Ala Asn Thr Ala Tyr
65                  70                  75                  80

Leu Gln Ile Asn Asn Leu Lys Asn Glu Asp Thr Ala Ile Tyr Phe Cys
                85                  90                  95

Thr Arg Glu Gly Asp Ala Leu Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430
```

```
Asn His Tyr Thr Gln Lys Ser Leu Ser Leu Ser Pro Gly Lys
        435                 440                 445
```

<210> SEQ ID NO 119
<211> LENGTH: 214
<212> TYPE: PRT
<213> ORGANISM: Artificial Sequence
<220> FEATURE:
<223> OTHER INFORMATION: m2B8 light chain

<400> SEQUENCE: 119

```
Asp Ile Val Met Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Arg Glu Lys Pro Gly Lys Thr Asn Asn Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 450
<212> TYPE: PRT
<213> ORGANISM: Artificial Sequence
<220> FEATURE:
<223> OTHER INFORMATION: m2B8 heavy chain

<400> SEQUENCE: 120

```
Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Asn Phe Asn Thr Tyr
            20                  25                  30

Thr Met Asn Trp Val Arg Gln Ala Pro Gly Lys Gly Leu Glu Trp Val
        35                  40                  45

Ala Arg Ile Arg Tyr Lys Ser Asn Asn Tyr Ala Thr Tyr Tyr Ala Asp
    50                  55                  60

Ser Val Lys Asp Arg Phe Thr Ile Ser Arg Asp Asp Ser Glu Ser Ile
65                  70                  75                  80
```

```
Leu Tyr Leu Gln Met Asn Asn Leu Arg Thr Asp Asp Thr Ala Ile Tyr
                85                  90                  95
Phe Cys Val Arg Glu Leu Gly Leu Trp Tyr Phe Asp Val Trp Gly Ala
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 121
<211> LENGTH: 214
<212> TYPE: PRT
<213> ORGANISM: Artificial Sequence
<220> FEATURE:
```

<223> OTHER INFORMATION: m4H3 light chain

<400> SEQUENCE: 121

Asp Ile Val Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Met His Trp Tyr Gln Gln Arg Lys Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Thr Asn Asn Trp Pro Trp
                85                  90                  95

Thr Phe Gly Gly Gly Thr Lys Leu Glu Phe Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 451
<212> TYPE: PRT
<213> ORGANISM: Artificial Sequence
<220> FEATURE:
<223> OTHER INFORMATION: m4H3 heavy chain

<400> SEQUENCE: 122

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Asn Ile Asn Trp Val Lys Gln Thr Asn Gly Lys Ser Leu Glu Trp Ile
        35                  40                  45

Gly Ile Ile Asn Pro Asn Tyr Gly Thr Thr Ser Tyr Asn Gln Lys Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Arg Asn Gly Asp Tyr Val Gly Tyr Ala Met Asp Ser Trp Gly
            100                 105                 110

Gln Gly Thr Ser Val Thr Val Ser Ser Ala Ser Thr Lys Gly Pro Ser
        115                 120                 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 123
<211> LENGTH: 214
<212> TYPE: PRT
<213> ORGANISM: Artificial Sequence
<220> FEATURE:
<223> OTHER INFORMATION: m3E7 light chain

<400> SEQUENCE: 123

Asp Ile Val Met Thr Gln Thr Thr Ala Ile Met Ser Ala Phe Pro Gly
1               5                   10                  15

Glu Lys Val Thr Met Thr Cys Ser Ala Ser Ser Ser Val Ser Tyr Met
            20                  25                  30
```

His Trp Tyr Gln Gln Lys Ser Gly Thr Ser Pro Lys Arg Trp Ile Tyr
        35                  40                  45

Asp Thr Ser Lys Leu Ala Ser Gly Val Pro Val Arg Phe Ser Gly Ser
 50                  55                  60

Gly Ser Gly Thr Ser Tyr Ser Leu Thr Ile Ser Asn Met Glu Ala Glu
 65                  70                  75                  80

Asp Ala Ala Thr Tyr Tyr Cys Gln Gln Trp Ser Arg Asn Pro Pro Phe
                 85                  90                  95

Thr Phe Gly Ala Gly Thr Lys Leu Glu Leu Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 124
<211> LENGTH: 446
<212> TYPE: PRT
<213> ORGANISM: Artificial Sequence
<220> FEATURE:
<223> OTHER INFORMATION: m3E7 heavy chain

<400> SEQUENCE: 124

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu His Trp Met
        35                  40                  45

Gly Trp Ile Asn Thr His Ser Gly Ala Pro Thr Tyr Val Asp Asp Phe
 50                  55                  60

Lys Gly Arg Phe Ala Phe Ser Leu Glu Thr Ser Ala Ser Thr Ala Phe
 65                  70                  75                  80

Leu Gln Ile Asn Asn Leu Ile Asn Glu Asp Thr Ala Thr Tyr Phe Cys
                 85                  90                  95

Ala Arg Glu Gly Asp Ala Leu Asp Tyr Trp Gly Gln Gly Thr Ser Val
             100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 125
<211> LENGTH: 214
<212> TYPE: PRT
<213> ORGANISM: Artificial Sequence
<220> FEATURE:
<223> OTHER INFORMATION: m1A8 light chain

<400> SEQUENCE: 125

Asp Ile Val Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Leu
                85                  90                  95
```

```
Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 126
<211> LENGTH: 452
<212> TYPE: PRT
<213> ORGANISM: Artificial Sequence
<220> FEATURE:
<223> OTHER INFORMATION: m1A8 heavy chain

<400> SEQUENCE: 126

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ser Phe Thr Ser Ser
            20                  25                  30

Trp Met His Trp Val Lys Gln Arg Pro Gly Gln Gly Leu Glu Trp Ile
        35                  40                  45

Gly Met Ile His Pro Asp Ser Gly Phe Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Arg Thr Ser Tyr Tyr Asp Thr Ser Tyr Thr Ser Met Asp Phe Trp
            100                 105                 110

Gly Gln Gly Asn Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 127
<211> LENGTH: 214
<212> TYPE: PRT
<213> ORGANISM: Artificial Sequence
<220> FEATURE:
<223> OTHER INFORMATION: m4G1 light chain

<400> SEQUENCE: 127

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Ile Leu Ser Ile Asn Ser Val Glu Ser
65                  70                  75                  80

Glu Asp Ile Ala Asp Tyr Tyr Cys Gln Gln Ser Asn Ser Trp Pro Trp
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 453
<212> TYPE: PRT
<213> ORGANISM: Artificial Sequence
<220> FEATURE:
<223> OTHER INFORMATION: m4G1 heavy chain

<400> SEQUENCE: 128

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ala Tyr
            20                  25                  30

Asn Met Asn Trp Val Lys Gln Ser Lys Gly Lys Ser Leu Glu Trp Ile
        35                  40                  45

Gly Leu Ile Asn Pro Asn Tyr Ala Thr Thr Ser Tyr Asn Gln Lys Phe
    50                  55                  60

Lys Asp Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Tyr Tyr Ser Tyr Tyr Ser Tyr Gly Gly Gly Tyr Ala Met Asp Tyr
            100                 105                 110

Trp Gly Gln Gly Thr Ser Val Thr Val Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450

<210> SEQ ID NO 129
<211> LENGTH: 213
<212> TYPE: PRT
<213> ORGANISM: Artificial Sequence
<220> FEATURE:
<223> OTHER INFORMATION: m2G3 light chain

<400> SEQUENCE: 129

Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Val Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190
```

```
Cys Glu Val Thr His Gln Gly Leu Ser Ser Pro Val Thr Lys Ser Phe
        195                 200                 205
Asn Arg Gly Glu Cys
    210

<210> SEQ ID NO 130
<211> LENGTH: 447
<212> TYPE: PRT
<213> ORGANISM: Artificial Sequence
<220> FEATURE:
<223> OTHER INFORMATION: m2G3 heavy chain

<400> SEQUENCE: 130

Glu Val Lys Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
            20                  25                  30

Ala Met Ser Trp Ile Arg Gln Thr Pro Glu Lys Arg Leu Glu Trp Val
        35                  40                  45

Ala Ala Ile Ser Asp Gly Gly Thr Tyr Thr Tyr Tyr Pro Asn Asn Val
    50                  55                  60

Lys Gly Arg Phe Thr Ile Ser Arg Asp Asp Ala Lys Asn Asn Leu Tyr
65                  70                  75                  80

Leu Gln Met Ser His Leu Lys Ser Glu Asp Thr Ala Met Tyr Tyr Cys
                85                  90                  95

Val Arg Asn Arg Gly Gly Pro Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 131
<211> LENGTH: 213
<212> TYPE: PRT
<213> ORGANISM: Artificial Sequence
<220> FEATURE:
<223> OTHER INFORMATION: m2F11 light chain

<400> SEQUENCE: 131

Asp Ile Val Leu Thr Gln Thr Pro Ala Leu Met Ser Ala Ser Pro Gly
1               5                   10                  15

Glu Lys Val Thr Met Thr Cys Ser Ala Ser Ser Ser Val Gly Ser Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Ile Pro Pro Thr
                85                  90                  95

Phe Gly Ala Gly Thr Thr Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 132
<211> LENGTH: 447
<212> TYPE: PRT
<213> ORGANISM: Artificial Sequence
```

<220> FEATURE:
<223> OTHER INFORMATION: m2F11 heavy chain

<400> SEQUENCE: 132

```
Glu Val Gln Leu Gln Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Ile Ile Gly Asp Gly Asp Thr Tyr Thr Tyr Tyr Pro Asp Ser Val
    50                  55                  60

Lys Gly Arg Phe Thr Val Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Val Arg Thr Arg Gly Gly Pro Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 133
<211> LENGTH: 218
<212> TYPE: PRT
<213> ORGANISM: Artificial Sequence
<220> FEATURE:
<223> OTHER INFORMATION: m3B8 light chain

<400> SEQUENCE: 133

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Phe Ala Met Tyr Phe Cys Gln Gln Ser Arg
                85                  90                  95

Lys Ile Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 134
<211> LENGTH: 451
<212> TYPE: PRT
<213> ORGANISM: Artificial Sequence
<220> FEATURE:
<223> OTHER INFORMATION: m3B8 heavy chain

<400> SEQUENCE: 134

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
```

```
            35                  40                  45
Gly Val Ile Trp Gly Asp Gly Thr Thr Asn Tyr His Ser Ala Leu Ile
 50                  55                  60
Ser Arg Leu Ile Ile Ser Lys Asp Asn Ser Lys Ser Gln Val Phe Leu
 65                  70                  75                  80
Lys Leu Asn Ser Leu Gln Thr Asp Asp Thr Ala Thr Tyr Tyr Cys Ala
                 85                  90                  95
Lys Glu Gly Asp Tyr Gly Asp Tyr Val Gly Trp Phe Ala Tyr Trp Gly
                100                 105                 110
Gln Gly Thr Leu Val Thr Val Ser Ala Ala Ser Thr Lys Gly Pro Ser
            115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450
```

<210> SEQ ID NO 135
<211> LENGTH: 652
<212> TYPE: DNA
<213> ORGANISM: Artificial Sequence
<220> FEATURE:
<223> OTHER INFORMATION: m2E7light chain(nucleotide)

<400> SEQUENCE: 135

```
gatattgtga tgacacaatc tacagcaatc atgtctgcat ctccagggga gaaggtcacc    60
atgacctgca gtgccagctc aagtgtaagt tacatgcact ggtaccagca gaagtcaggc   120
acctccccca agagatggat ttatgacaca tccagactgg cttctggagt ccctgctcgc   180
ttcagtggca gtgggtctgg gacctcttac tctctcacaa tcagcagcat ggaggctgaa   240
gatgctgcca cttattactg ccagcagtgg agtaataccc acccttcac gttcggtgct    300
gggaccaagt tggagctgaa acgtacggtg ctgcaccat ctgtcttcat cttcccgcca    360
tctgatgagc agttgaaatc tggtaccgct agcgttgtgt gcctgctgaa taacttttat   420
ccacgggagg ctaaggtgca gtggaaagtg gacaatgccc tccagagcgg aaatagccaa   480
gagtccgtta ccgaacagga ctctaaagac tctacatact ccctgtcctc cacactgacc   540
ctctccaagg ccgactatga gaaacacaag gtttacgcat gcgaggtcac acaccaggga   600
ctctcctctc ccgtgaccaa gagcttcaac cggggagaat gctaatgaat tc           652
```

<210> SEQ ID NO 136
<211> LENGTH: 1348
<212> TYPE: DNA
<213> ORGANISM: Artificial Sequence
<220> FEATURE:
<223> OTHER INFORMATION: m2E7 heavy chain(nucleotide)

<400> SEQUENCE: 136

```
gaggtgcagc tgcaggagtc tggacctgag ctgaagaagc ctggagagac agtcaagatc    60
tcctgcaagg cttctgggta taccttcaca acctatggaa tgagctgggt gaaacaggct   120
ccaggaaagg gtttacagtg gatgggctgg ataaacacca actctggagt gccaacctat   180
gttgaggact tcaagggacg gtttgccttc tctttggaat cctctgccaa cactgcctat   240
ttgcagatca acaacctcaa aaatgaggac acggctatat acttctgtac aagagagggg   300
gatgctctgg actactgggg tcaaggaacc tcagtcaccg tctcctcagc cagcactaag   360
gggccctctg tgtttccact cgcccttct agcaaaagca cttccggagg cactgcagca   420
ctcgggtgtc tggtcaaaga ttatttccct gagccagtca ccgtgagctg aactctggc    480
gccctcacct ccggggttca cccttcca gccgtcctgc agtcctccgg cctgtactcc     540
ctgagcagcg tcgttaccgt gccatcctct tctctgggga cccagacata catctgcaat   600
gtcaaccata agcctagcaa caccaaggtg gacaaaaagg tcgagccaaa gagctgcgat   660
aagacacaca cctgccctcc atgccccgca cctgaactcc tgggcgggcc ttccgttttc   720
ctgtttcctc ccaagcccaa ggatacactg atgattagcc gcaccccga agtcacttgc    780
gtggtggtgg atgtgagcca tgaagatcca gaagttaagt ttaactggta tgtggacggg   840
gtcgaggtgc acaatgctaa acaaagccc agggaggagc aatataactc cacatacaga   900
gtggtgtccg ttctgacagt cctgcaccag gactggctga acgggaagga atacaagtgc   960
aaggtgtcta ataaggcact gccagccccc atagagaaga caatctctaa agctaaaggc  1020
caaccacgcg agcctcaggt ctacacactg ccaccatcca gggacgaact gaccaagaat  1080
```

```
caggtgagcc tgacttgtct cgtcaaagga ttctacccaa cgacatcgc cgtggagtgg   1140 gaatccaacg gccaaccaga gaacaactac aagaccaccc caccagtcct ggactctgat   1200
gggagctttt tcctgtattc aagctgaca gtggacaagt ctcggtggca acagggcaac   1260
gtgttcagct gctccgtgat gcatgaagcc ctgcataacc actataccca gaaaagcctc   1320
agcctgtccc ccgggaaata atgaattc                                     1348

<210> SEQ ID NO 137
<211> LENGTH: 652
<212> TYPE: DNA
<213> ORGANISM: Artificial Sequence
<220> FEATURE:
<223> OTHER INFORMATION: m2B8 light chain(nucleotide)

<400> SEQUENCE: 137
gacattgtga tgacccagtc tccatcttat cttgctgcat ctcctggaga aaccattact    60
ataaattgca gggcaagtaa gagcattagc aaatatttag cctggtatcg agagaaacct   120
gggaaaacta taatcttct tatctactct ggatccactt tgcaatctgg aattccatca    180
aggttcagtg gcagtggatc tggtacagat ttcactctca ccatcagtag cctggagcct   240
gaagattttg caatgtatta ctgtcaacag cataatgaat accccgctcac gttcggtgct   300 gggaccaagc tggagctgaa acgtacggtg gctgcaccat ctgtcttcat cttcccgcca   360
tctgatgagc agttgaaatc tggtaccgct agcgttgtgt gcctgctgaa taacttttat   420
ccacgggagg ctaaggtgca gtggaaagtg gacaatgccc tccagagcgg aaatagccaa   480
gagtccgtta ccgaacagga ctctaaagac tctacatact ccctgtcctc cacactgacc   540
ctctccaagg ccgactatga gaaacacaag gtttacgcat gcgaggtcac acaccaggga   600
ctctcctctc ccgtgaccaa gagcttcaac cggggagaat gctaatgaat tc           652

<210> SEQ ID NO 138
<211> LENGTH: 1360
<212> TYPE: DNA
<213> ORGANISM: Artificial Sequence
<220> FEATURE:
<223> OTHER INFORMATION: m2B8 heavy chain(nucleotide)

<400> SEQUENCE: 138
gaggtgcagc tgcaggagtc tggtggagga ttggtgcagc ctaaagggtc attgaaactc    60
tcatgtgcag cctctggatt caacttcaat acctacacca tgaactgggt ccgccaggct   120
ccaggaaagg gtttggaatg ggttgctcgc ataagatata aagtaataa ttatgcaaca   180 tattatgccg attcagtgaa agacagattc accatctcca gagatgattc agaaagcatc   240
ctctatctgc aaatgaacaa cttgagaact gacgacacag ccatttattt ctgtgtgagg   300
gaactgggac tgtggtactt cgatgtctgg ggcgcaggga ccacggtcac cgtctcctca   360
gccagcacta gggggccctc tgtgtttcca ctcgccccctt ctagcaaaag cacttccgga   420
ggcactgcag cactcgggtg tctggtcaaa gattatttcc ctgagccagt caccgtgagc   480
tggaactctg gcgccctcac ctccggggtt cacaccttc cagccgtcct gcagtcctcc   540
ggcctgtact ccctgagcag cgtcgttacc gtgccatcct cttctctggg gacccagaca   600
tacatctgca atgtcaacca taagcctagc aacaccaagg tggacaaaaa ggtcgagcca   660
aagagctgcg ataagacaca cacctgccct ccatgccccg cacctgaact cctgggcggg   720
ccttccgttt tcctgtttcc tcccaagccc aaggatacac tgatgattag ccgcaccccc   780
gaagtcactt gcgtggtggt ggatgtgagc catgaagatc cagaagttaa gtttaactgg   840
```

```
tatgtggacg gggtcgaggt gcacaatgct aaaacaaagc ccagggagga gcaatataac    900
tccacataca gagtggtgtc cgttctgaca gtcctgcacc aggactggct gaacgggaag    960
gaatacaagt gcaaggtgtc taataaggca ctgccagccc ccatagagaa gacaatctct   1020
aaagctaaag gccaaccacg cgagcctcag gtctacacac tgccaccatc cagggacgaa   1080
ctgaccaaga atcaggtgag cctgacttgt ctcgtcaaag gattctaccc aagcgacatc   1140
gccgtggagt gggaatccaa cggccaacca gagaacaact acaagaccac cccaccagtc   1200
ctggactctg atgggagctt tttcctgtat tccaagctga cagtggacaa gtctcggtgg   1260
caacagggca acgtgttcag ctgctccgtg atgcatgaag ccctgcataa ccactatacc   1320
cagaaaagcc tcagcctgtc ccccgggaaa taatgaattc                         1360

<210> SEQ ID NO 139
<211> LENGTH: 652
<212> TYPE: DNA
<213> ORGANISM: Artificial Sequence
<220> FEATURE:
<223> OTHER INFORMATION: m4H3 light chain(nucleotide)

<400> SEQUENCE: 139
gatatcgttc tcacccagtc tccagccatc ctctctgtga gtccaggaga aagagtcagt     60
ttctcctgca gggccagtca gagcattggc acaagcatgc actggtatca gcaaagaaaa    120
aatggttctc caaggcttct cataaagtat gcttctgagt ctatctctgg gatcccttcc    180
aggtttagtg gcagtggatc aggacagat tttactctta gcatcaacag tgtggagtct    240
gaggatattg cagattatta ctgtcaacaa actaataact ggccgtggac gttcggtgga    300
ggcaccaagc tggaattcaa acgtacggtg gctgcaccat ctgtcttcat cttcccgcca    360
tctgatgagc agttgaaatc tggtaccgct agcgttgtgt gcctgctgaa taacttttat    420
ccacgggagg ctaaggtgca gtggaaagtg gacaatgccc tccagagcgg aaatagccaa    480
gagtccgtta ccgaacagga ctctaaagac tctacatact ccctgtcctc cacactgacc    540
ctctccaagg ccgactatga gaaacacaag gtttacgcat gcgaggtcac acaccaggga    600
ctctcctctc ccgtgaccaa gagcttcaac cggggagaat gctaatgaat tc            652

<210> SEQ ID NO 140
<211> LENGTH: 1363
<212> TYPE: DNA
<213> ORGANISM: Artificial Sequence
<220> FEATURE:
<223> OTHER INFORMATION: m4H3 heavy chain(nucleotide)

<400> SEQUENCE: 140
caggtgcagc tgcagcagtc tggacctgag ctggtgaagc ctggcgcttc agtgaagata     60
tcctgcaagg cttctggtta ctcattcact gcctacaaca ttaactgggt gaagcagacc    120
aatggaaaga gccttgagtg gattggaata attaatccta ctatggtac tactagttac    180 aaccagaagt tcaagggcaa ggccacattg actgtagacc aatcttccag tacagcctac    240
atgcagctca acagcctgac atctgaggac tctgcagtct attactgtgc aagacggaat    300
ggtgactacg tgggatatgc tatggactcc tggggtcaag aacctcagt caccgtctcc    360 tcagccagca ctaaggggcc ctctgtgttt ccactcgccc cttctagcaa aagcacttcc    420
ggaggcactg cagcactcgg tgtctggtc aaagattatt tccctgagcc agtcaccgtg    480
agctggaact ctggcgccct cacctccggg gttcacacct ttccagccgt cctgcagtcc    540
```

```
tccggcctgt actccctgag cagcgtcgtt accgtgccat cctcttctct ggggacccag    600
acatacatct gcaatgtcaa ccataagcct agcaacacca aggtggacaa aaaggtcgag    660
ccaaagagct gcgataagac acacacctgc cctccatgcc ccgcacctga actcctgggc    720
gggccttccg ttttcctgtt tcctcccaag cccaaggata cactgatgat tagccgcacc    780
cccgaagtca cttgcgtggt ggtggatgtg agccatgaag atccagaagt taagtttaac    840
tggtatgtgg acggggtcga ggtgcacaat gctaaaacaa agcccaggga ggagcaatat    900
aactccacat acagagtggt gtccgttctg acagtcctgc accaggactg gctgaacggg    960
aaggaataca gtgcaaggt gtctaataag gcactgccag cccccataga aagacaatc    1020 tctaaagcta aaggccaacc acgcgagcct caggtctaca cactgccacc atccagggac    1080
gaactgacca agaatcaggt gagcctgact tgtctcgtca aggattcta cccaagcgac    1140 atcgccgtgg agtgggaatc caacggccaa ccagagaaca actacaagac caccccacca    1200
gtcctggact ctgatgggag cttttttcctg tattccaagc tgacagtgga caagtctcgg    1260
tggcaacagg gcaacgtgtt cagctgctcc gtgatgcatg aagccctgca taaccactat    1320
acccagaaaa gcctcagcct gtcccccggg aaataatgaa ttc    1363

<210> SEQ ID NO 141
<211> LENGTH: 652
<212> TYPE: DNA
<213> ORGANISM: Artificial Sequence
<220> FEATURE:
<223> OTHER INFORMATION: m3E7 light chain(nucleotide)

<400> SEQUENCE: 141
gacattgtga tgacccaaac tacagcaatc atgtctgcat ttccagggga aaggtcacc    60 atgacctgca gtgccagctc aagtgtaagt tacatgcact ggtaccagca gaagtcaggc    120
acctccccca aaagatggat ttatgacaca tccaaactgg cttctggagt ccctgttcgc    180
ttcagtggca gtgggtctgg gacctcttac tctctcacaa tcagcaacat ggaggctgaa    240
gatgctgcca cttattattg ccagcagtgg agtcgtaacc cacccttcac gttcggtgct    300
gggaccaagc tggagctgaa acgtacggtg gctgcaccat ctgtcttcat cttcccgcca    360
tctgatgagc agttgaaatc tggtaccgct agcgttgtgt gcctgctgaa taacttttat    420
ccacgggagg ctaaggtgca gtggaaagtg gacaatgccc tccagagcgg aaatagccaa    480
gagtccgtta ccgaacagga ctctaaagac tctacatact ccctgtcctc cacactgacc    540
ctctccaagg ccgactatga aaacacaag gtttacgcat gcgaggtcac acaccaggga    600
ctctcctctc ccgtgaccaa gagcttcaac cggggagaat gctaatgaat tc    652

<210> SEQ ID NO 142
<211> LENGTH: 1348
<212> TYPE: DNA
<213> ORGANISM: Artificial Sequence
<220> FEATURE:
<223> OTHER INFORMATION: m3E7 heavy chain(nucleotide)

<400> SEQUENCE: 142
cagatccagc tggtgcagag cggaccagaa ctgaagaagc caggagagac agtcaagatc    60
tcctgcaagg cttctggata cgttcaca acctatggaa tgagctgggt gaaacaggct    120
ccaggaaagg gtttgcactg gatgggctgg ataaacaccc actctggagc gccaacatat    180
gttgatgact caagggacg gtttgccttc tctttggaaa cctctgccag cactgccttt    240
ttgcagatca acaacctcat aaatgaggac acggctacat atttctgtgc aagagagggg    300
```

```
gatgctctgg actactgggg tcaaggaacc tcagtcaccg tctcctcagc cagcactaag      360
gggccctctg tgtttccact cgccccttct agcaaaagca cttccggagg cactgcagca      420
ctcgggtgtc tggtcaaaga ttatttccct gagccagtca ccgtgagctg gaactctggc      480
gccctcacct ccggggttca cacctttcca gccgtcctgc agtcctccgg cctgtactcc      540
ctgagcagcg tcgttaccgt gccatcctct tctctgggga cccagacata catctgcaat      600
gtcaaccata agcctagcaa caccaaggtg gacaaaaagg tcgagccaaa gagctgcgat      660
aagacacaca cctgccctcc atgccccgca cctgaactcc tgggcgggcc ttccgttttc      720
ctgtttcctc caagcccaa ggatacactg atgattagcc gccccccga agtcacttgc       780 gtggtggtgg atgtgagcca tgaagatcca gaagttaagt ttaactggta tgtggacggg      840
gtcgaggtgc acaatgctaa acaaagccc agggaggagc aatataactc cacatacaga      900
gtggtgtccg ttctgacagt cctgcaccag gactggctga cgggaagga atacaagtgc       960 aaggtgtcta ataaggcact gccagccccc atagagaaga caatctctaa agctaaaggc     1020
caaccacgcg agcctcaggt ctacacactg ccaccatcca gggacgaact gaccaagaat     1080
caggtgagcc tgacttgtct cgtcaaagga ttctacccaa gcgacatcgc cgtggagtgg     1140
gaatccaacg gccaaccaga gaacaactac aagaccaccc caccagtcct ggactctgat     1200
gggagctttt tcctgtattc caagctgaca gtggacaagt ctcggtggca cagggcaac      1260 gtgttcagct gctccgtgat gcatgaagcc ctgcataacc actataccca gaaaagcctc     1320
agcctgtccc ccgggaaata atgaattc                                        1348
```

<210> SEQ ID NO 143
<211> LENGTH: 652
<212> TYPE: DNA
<213> ORGANISM: Artificial Sequence
<220> FEATURE:
<223> OTHER INFORMATION: m1A8 light chain(nucleotide)

<400> SEQUENCE: 143

```
gatattgtgc tgacccagtc tccagccatc ctgtctgtga gtccaggaga aagagtcagt       60
ttctcctgca gggccagtca gagcattggc acaagcatac attggtatca gcaaagaaca      120
aatggttctc caaggcttct cataaagtat gcttctgagt ctatctctgg gatcccttcc      180
aggtttagtg gcagtggatc aggacagat tttactctta gcatcaacag tgtggagtct       240
gaagatattg cagattatta ctgtcaacaa agtaatagct ggccactcac gttcggtgct      300
gggaccaagc tggagctgaa acgtacggtg gctgcaccat ctgtcttcat cttcccgcca      360
tctgatgagc agttgaaatc tggtaccgct agcgttgtgt gcctgctgaa taacttttat      420
ccacgggagg ctaaggtgca gtggaaagtg acaatgccc tccagagcgg aaatagccaa       480
gagtccgtta ccgaacagga ctctaaagac tctacatact ccctgtcctc cacactgacc      540
ctctccaagg ccgactatga aaacacaag gtttacgcat gcgaggtcac acaccaggga      600
ctctcctctc ccgtgaccaa gagcttcaac cggggagaat gctaatgaat tc             652
```

<210> SEQ ID NO 144
<211> LENGTH: 1366
<212> TYPE: DNA
<213> ORGANISM: Artificial Sequence
<220> FEATURE:
<223> OTHER INFORMATION: m1A8 heavy chain(nucleotide)

<400> SEQUENCE: 144

```
gaggtgcagc tgcaggagtc tggggctgaa ttggtaaagc ctggggcttc agtgaagttg      60
tcctgcaagg cttctggcta cagtttcacc agctcctgga tgcactgggt gaagcagagg     120
cctggacaag gccttgagtg gattggaatg attcatcctg atagtggttt tactaactac     180
aatgagaagt tcaagagcaa ggccacactg actgtagaca atcctccag cacagcctac      240 atgcgcctca gcagcctgac atctgaggac tctgcggtct attactgtgc aaggacctct     300
tactacgata ctagctacac ttctatggac ttctggggtc aaggaaactc agtcaccgtc     360
tcctcagcca gcactaaggg gccctctgtg tttccactcg ccccttctag caaaagcact     420
tccggaggca ctgcagcact cggggtgtctg gtcaaagatt atttccctga gccagtcacc     480
gtgagctgga actctggcgc cctcacctcc ggggttcaca ccttccagc cgtcctgcag      540 tcctccggcc tgtactccct gagcagcgtc gttaccgtgc catcctcttc tctggggacc     600
cagacataca tctgcaatgt caaccataag cctagcaaca ccaaggtgga caaaaaggtc     660
gagccaaaga gctgcgataa acacacacc tgccctccat gccccgcacc tgaactcctg      720
ggcgggcctt ccgttttcct gtttcctccc aagcccaagg atacactgat gattagccgc     780 accccccgaag tcacttgcgt ggtggtggat gtgagccatg aagatccaga agttaagttt     840
aactggtatg tggacggggt cgaggtgcac aatgctaaaa caaagcccag ggaggagcaa     900
tataactcca catacagagt ggtgtccgtt ctgacagtcc tgcaccagga ctggctgaac     960
gggaaggaat acaagtgcaa ggtgtctaat aaggcactgc cagcccccat agagaagaca    1020
atctctaaag ctaaaggcca accacgcgag cctcaggtct acacactgcc accatccagg    1080
gacgaactga ccaagaatca ggtgagcctg acttgtctcg tcaaaggatt ctacccaagc    1140
gacatcgccg tggagtggga atccaacggc caaccagaga caactacaa gaccacccca    1200 ccagtcctgg actctgatgg gagctttttc ctgtattcca gctgacagt ggacaagtct    1260 cggtggcaac agggcaacgt gttcagctgc tccgtgatgc atgaagccct gcataaccac    1320
tatacccaga aaagcctcag cctgtccccc gggaaataat gaattc                  1366
```

<210> SEQ ID NO 145
<211> LENGTH: 321
<212> TYPE: DNA
<213> ORGANISM: Artificial Sequence
<220> FEATURE:
<223> OTHER INFORMATION: m4G1 light chain(nucleotide)

<400> SEQUENCE: 145

```
gatatcttgc tgacccaatc tccagccatc ctgtctgtga gtccaggaga aagagtcagt      60
ttttcctgca gggccagtca gagcattggc acaagcatac actggtatca gcaaagaaca     120
aatgggtctc caaggcttct cataaagtat gcttctgagt ctatctctgg gatcccttcc     180
aggtttagtg gcagtggatc agggacagat tttattctta gcatcaacag tgtggagtct     240
gaggatattg ctgattatta ctgtcagcaa agtaatagct ggccgtggac gttcggtgga     300
ggcaccaggc tggaaatcaa a                                                321
```

<210> SEQ ID NO 146
<211> LENGTH: 1369
<212> TYPE: DNA
<213> ORGANISM: Artificial Sequence
<220> FEATURE:
<223> OTHER INFORMATION: m4G1 heavy chain(nucleotide)

<400> SEQUENCE: 146

```
caggtccagc tgcagcagtc cggacctgag ctggtgaagc ctggcgcttc agtgaagata      60
```

```
tcatgcaagg cttctggtta ctcattcact gcctacaaca tgaactgggt gaagcagagc      120
aagggaaaga gccttgagtg gattggacta attaatccta actatgccac gactagttac      180
aatcagaagt tcaaggacaa ggccacattg actgtggacc aatcttccag cacagcctac      240
atgcagctca acagcctgac atctgaggac tctgcagtct attactgtgc ctactatagt      300
tactatagtt acggggggga atatgctatg gactactggg gtcaaggaac ctcagtcacc      360
gtctcctcag ccagcactaa ggggccctct gtgtttccac tcgccccttc tagcaaaagc      420
acttccggag gcactgcagc actcgggtgt ctggtcaaag attatttccc tgagccagtc      480
accgtgagct ggaactctgg cgccctcacc tccggggttc acacctttcc agccgtcctg      540
cagtcctccg gcctgtactc cctgagcagc gtcgttaccg tgccatcctc ttctctgggg      600
acccagacat acatctgcaa tgtcaaccat aagcctagca acaccaaggt ggacaaaaag      660
gtcgagccaa agagctgcga taagacacac acctgccctc catgccccgc acctgaactc      720
ctgggcgggc cttccgtttt cctgtttcct cccaagccca aggatacact gatgattagc      780
cgcacccccg aagtcacttg cgtggtggtg gatgtgagcc atgaagatcc agaagttaag      840
tttaactggt atgtggacgg ggtcgaggtg cacaatgcta aaacaaagcc cagggaggag      900
caatataact ccacatacag agtggtgtcc gttctgacag tcctgcacca ggactggctg      960
aacgggaagg aatacaagtg caaggtgtct aataaggcac tgccagcccc catagagaag     1020
acaatctcta aagctaaagg ccaaccacgc gagcctcagg tctacacact gccaccatcc     1080
agggacgaac tgaccaagaa tcaggtgagc ctgacttgtc tcgtcaaagg attctaccca     1140
agcgacatcg ccgtggagtg ggaatccaac ggccaaccag agaacaacta caagaccacc     1200
ccaccagtcc tggactctga tgggagcttt ttcctgtatt ccaagctgac agtggacaag     1260
tctcggtggc aacagggcaa cgtgttcagc tgctccgtga tgcatgaagc cctgcataac     1320
cactataccc agaaaagcct cagcctgtcc cccgggaaat aatgaattc                 1369
```

<210> SEQ ID NO 147
<211> LENGTH: 649
<212> TYPE: DNA
<213> ORGANISM: Artificial Sequence
<220> FEATURE:
<223> OTHER INFORMATION: m2G3 light chain(nucleotide)

<400> SEQUENCE: 147

```
gatatcgtgc tcactcagtc tccagcaatc atgtctgcat ctccagggga gaaggtcacc       60
atgacctgca gtgccagctc aagtgtaagt tacatgaact ggtaccagca gaagtcaggc      120
acctccccca aaagatggat ttatgacaca tccaaactgg cttctggagt ccctgttcgc      180
ttcagtggca gtgggtctgg gacctcttac tctctcacaa tcagcagcat ggaggctgaa      240
gatgctgcca cttattactg ccagcagtgg aatagtaacc acccacgtt cggtgctggg       300 accaagctgg agctgaaacg tacggtggct gcaccatctg tcttcatctt cccgccatct      360
gatgagcagt tgaaatctgg taccgctagc gttgtgtgcc tgctgaataa cttttatcca      420
cgggaggcta aggtgcagtg gaaagtggac aatgccctcc agagcggaaa tagccaagag      480
tccgttaccg aacaggactc taaagactct acatactccc tgtcctccac actgaccctc      540
tccaaggccg actatgagaa acacaaggtt tacgcatgcg aggtcacaca ccagggactc      600
tcctctcccg tgaccaagag cttcaaccgg ggagaatgct aatgaattc                  649
```

<210> SEQ ID NO 148

<211> LENGTH: 1351
<212> TYPE: DNA
<213> ORGANISM: Artificial Sequence
<220> FEATURE:
<223> OTHER INFORMATION: m2G3 heavy chain(nucleotide)

<400> SEQUENCE: 148

| | | | | | |
|---|---|---|---|---|---|
| gaggtgaagc | tgcaggagtc | tgggggaggc | ttagtgaagc | ctggagggtc | cctgaaactc | 60 |
| tcctgtgcag | cctctggatt | cactttcagt | agctttgcca | tgtcttggat | tcgccagact | 120 |
| ccggaaaaga | ggctggagtg | gtcgcgggcc | attagtgatg | gtggtactta | cacctactat | 180 |
| ccaaacaatg | taaagggccg | attcaccatc | tccagagacg | atgccaagaa | taacctgtac | 240 |
| ctgcaaatga | gtcatctgaa | gtctgaggac | acagccatgt | attactgtgt | aagaaatagg | 300 |
| gggggacccct | ttgactactg | gggccaaggc | accactctca | cagtctcctc | agccagcact | 360 |
| aaggggcccct | ctgtgtttcc | actcgcccct | tctagcaaaa | gcacttccgg | aggcactgca | 420 |
| gcactcgggt | gtctggtcaa | agattatttc | cctgagccag | tcaccgtgag | ctggaactct | 480 |
| ggcgccctca | cctccggggt | tcacaccttt | ccagccgtcc | tgcagtcctc | cggcctgtac | 540 |
| tccctgagca | gcgtcgttac | cgtgccatcc | tcttctctgg | gacccagac | atacatctgc | 600 |
| aatgtcaacc | ataagcctag | caacaccaag | gtggacaaaa | aggtcgagcc | aaagagctgc | 660 |
| gataagacac | acacctgccc | tccatgcccc | gcacctgaac | tcctgggcgg | gccttccgtt | 720 |
| ttcctgtttc | ctcccaagcc | caaggataca | ctgatgatta | gccgcacccc | cgaagtcact | 780 |
| tgcgtggtgg | tggatgtgag | ccatgaagat | ccagaagtta | agtttaactg | gtatgtggac | 840 |
| ggggtcgagg | tgcacaatgc | taaaacaaag | cccagggagg | agcaatataa | ctccacatac | 900 |
| agagtggtgt | ccgttctgac | agtcctgcac | caggactggc | tgaacgggaa | ggaatacaag | 960 |
| tgcaaggtgt | ctaataaggc | actgccagcc | cccatagaga | gacaatctc | taaagctaaa | 1020 |
| ggccaaccac | gcgagcctca | ggtctacaca | ctgccaccat | ccagggacga | actgaccaag | 1080 |
| aatcaggtga | gcctgacttg | tctcgtcaaa | ggattctacc | caagcgacat | cgccgtggag | 1140 |
| tgggaatcca | acggccaacc | agagaacaac | tacaagacca | cccaccagt | cctggactct | 1200 |
| gatgggagct | ttttcctgta | ttccaagctg | acagtggaca | agtctcggtg | caacagggc | 1260 |
| aacgtgttca | gctgctccgt | gatgcatgaa | gccctgcata | accactatac | ccagaaaagc | 1320 |
| ctcagcctgt | cccccgggaa | ataatgaatt | c | | | 1351 |

<210> SEQ ID NO 149
<211> LENGTH: 649
<212> TYPE: DNA
<213> ORGANISM: Artificial Sequence
<220> FEATURE:
<223> OTHER INFORMATION: m2F11 light chain(nucleotide)

<400> SEQUENCE: 149

| | | | | | |
|---|---|---|---|---|---|
| gatatcgtgc | tcacccaaac | tccagcactc | atgtctgcat | ctccagggga | gaaggtcacc | 60 |
| atgacctgca | gtgccagctc | aagtgtaggt | tccatgcact | ggtaccagca | gaagtcaggc | 120 |
| acctcccca | aaagatggat | ttatgacaca | tccaaactgg | cttctggagt | ccctgctcgc | 180 |
| ttcagtggca | gtgggtctgg | gacctcttac | tctctcacaa | tcagcagcat | ggaggctgaa | 240 |
| gatgctgcca | cttattactg | ccaacagtgg | agtagtatcc | cacccacgtt | cggtgctggg | 300 |
| accacgctgg | agctgaaacg | tacggtggct | gcaccatctg | tcttcatctt | cccgccatct | 360 |
| gatgagcagt | tgaaatctgg | taccgctagc | gttgtgtgcc | tgctgaataa | cttttatcca | 420 |
| cgggaggcta | aggtgcagtg | gaaagtggac | aatgcccctcc | agagcggaaa | tagccaagag | 480 |

| | |
|---|---|
| tccgttaccg aacaggactc taaagactct acatactccc tgtcctccac actgaccctc | 540 |
| tccaaggccg actatgagaa acacaaggtt tacgcatgcg aggtcacaca ccagggactc | 600 |
| tcctctcccg tgaccaagag cttcaaccgg ggagaatgct aatgaattc | 649 |

<210> SEQ ID NO 150
<211> LENGTH: 1351
<212> TYPE: DNA
<213> ORGANISM: Artificial Sequence
<220> FEATURE:
<223> OTHER INFORMATION: m2F11 heavy chain(nucleotide)

<400> SEQUENCE: 150

| | |
|---|---|
| gaggtgcagc tgcaggagtc tgggggagac ttagtgaagc ctggagggtc cctgaaactc | 60 |
| tcctgtgcag cctctggatt cactttcagt agctatgcca tgtcttgggt tcgccagact | 120 |
| ccggaaaaga ggctggagtg ggtcgcaatc attggtgatg gtgatactta cacctactat | 180 |
| ccagacagtg taaagggccg attcaccgtc tccagagaca atgccaagaa caacctctac | 240 |
| ctgcaaatga gccatctgaa gtctgaggac acagccatgt attactgtgt aagaactagg | 300 |
| gggggacccct ttgactactg gggccaaggc accactctca cagtctcctc agccagcact | 360 |
| aagggcccct ctgtgtttcc actcgcccct tctagcaaaa gcacttccgg aggcactgca | 420 |
| gcactcgggt gtctggtcaa agattatttc cctgagccag tcaccgtgag ctggaactct | 480 |
| ggcgccctca cctccggggt tcacaccttt ccagccgtcc tgcagtcctc cggcctgtac | 540 |
| tccctgagca gcgtcgttac cgtgccatcc tcttctctgg ggaccagac atacatctgc | 600 |
| aatgtcaacc ataagcctag caacaccaag gtggacaaaa aggtcgagcc aaagagctgc | 660 |
| gataagacac acacctgccc ctccatgccc gcacctgaac tcctgggcgg gccttccgtt | 720 |
| ttcctgtttc ctcccaagcc caaggataca ctgatgatta gccgcacccc cgaagtcact | 780 |
| tgcgtggtgg tggatgtgag ccatgaagat ccagaagtta agtttaactg gtatgtggac | 840 |
| ggggtcgagg tgcacaatgc taaaacaaag cccagggagg agcaatataa ctccacatac | 900 |
| agagtggtgt ccgttctgac agtcctgcac caggactggc tgaacgggaa ggaatacaag | 960 |
| tgcaaggtgt ctaataaggc actgccagcc cccatagaga agacaatctc taaagctaaa | 1020 |
| ggccaaccac gcgagcctca ggtctacaca ctgccaccat ccagggacga actgaccaag | 1080 |
| aatcaggtga gcctgacttg tctcgtcaaa ggattctacc caagcgacat cgccgtggag | 1140 |
| tgggaatcca acggccaacc agagaacaac tacaagacca ccccaccagt cctggactct | 1200 |
| gatgggagct ttttcctgta ttccaagctg acagtggaca gtctcggtg caacagggc | 1260 |
| aacgtgttca gctgctccgt gatgcatgaa gccctgcata ccactatac ccagaaaagc | 1320 |
| ctcagcctgt cccccgggaa ataatgaatt c | 1351 |

<210> SEQ ID NO 151
<211> LENGTH: 664
<212> TYPE: DNA
<213> ORGANISM: Artificial Sequence
<220> FEATURE:
<223> OTHER INFORMATION: m3B8 light chain(nucleotide)

<400> SEQUENCE: 151

| | |
|---|---|
| gatatcgtgc tgacccaatc tccagcttct ttggctgtgt ctctagggca gagagccacc | 60 |
| atctcctgca gagccagtga aagtgttgaa tattatggca aagtttaat gcagtggtac | 120 |
| caacagaaac caggacagcc acccaaactc ctcatctatg ctgcatccaa cgtagaatct | 180 |

| | |
|---|---|
| ggggtccctg ccaggtttag tggcagtggg tctgggacag acttcagcct caacatccat | 240 |
| cctgtggagg aggatgattt tgcaatgtat ttctgtcagc aaagtaggaa gattccttac | 300 |
| acgttcggag gggggaccaa gctggaaata aaacgtacgg tggctgcacc atctgtcttc | 360 |
| atcttcccgc catctgatga gcagttgaaa tctggtaccg ctagcgttgt gtgcctgctg | 420 |
| aataactttt atcccgggga ggctaaggtg cagtggaaag tggacaatgc ctccagagc | 480 |
| ggaaatagcc aagagtccgt taccgaacag gactctaaag actctacata ctccctgtcc | 540 |
| tccacactga ccctctccaa ggccgactat gagaaacaca aggtttacgc atgcgaggtc | 600 |
| acacaccagg gactctcctc tcccgtgacc aagagcttca ccggggagag atgctaatga | 660 |
| attc | 664 |

<210> SEQ ID NO 152
<211> LENGTH: 1363
<212> TYPE: DNA
<213> ORGANISM: Artificial Sequence
<220> FEATURE:
<223> OTHER INFORMATION: m3B8 heavy chain(nucleotide)

<400> SEQUENCE: 152

| | |
|---|---|
| caggtccagc tgcaggagtc aggacctggc ctggtggcgc cctcacagag cctgtccatc | 60 |
| acatgcactg tctcagggtt ctcattaacc aactatgctg taagctgggt tcgccagcct | 120 |
| ccaggaaagg gtctggagtg gctgggagta atatggggtg acgggaccac aaattatcat | 180 |
| tcagctctca tatccagact gattatcagc aaggataact ccaagagcca gttttctta | 240 |
| aaactgaaca gtctgcaaac tgatgacaca gccacgtact actgtgccaa agagggcgac | 300 |
| tatggtgact acgtaggctg gtttgcttac tggggccaag gactctggt cactgtctct | 360 |
| gcagccagca ctaagggcc ctctgtgttt ccactcgccc cttctagcaa aagcacttcc | 420 |
| ggaggcactg cagcactcgg gtgtctggtc aaagattatt ccctgagcc agtcaccgtg | 480 |
| agctggaact ctggcgccct cacctccggg gttcacacct ttccagccgt cctgcagtcc | 540 |
| tccggcctgt actccctgag cagcgtcgtt accgtgccat cctcttctct ggggacccag | 600 |
| acatacatct gcaatgtcaa ccataagcct agcaacacca aggtggacaa aaggtcgag | 660 |
| ccaaagagct cgataagac acacacctgc cctccatgcc ccgcacctga actcctgggc | 720 |
| gggccttccg tttttcctgt tcctcccaag cccaaggata cactgatgat tagccgcacc | 780 |
| cccgaagtca cttgcgtggt ggtggatgtg agccatgaag atccagaagt taagtttaac | 840 |
| tggtatgtgg acggggtcga ggtgcacaat gctaaaacaa gcccaggga ggagcaatat | 900 |
| aactccacat acagagtggt gtccgttctg acagtcctgc accaggactg gctgaacggg | 960 |
| aaggaataca gtgcaaggt gtctaataag gcactgccag cccccataga aagacaatc | 1020 |
| tctaaagcta aggccaacc acgcgagcct caggtctaca cactgccacc atccagggac | 1080 |
| gaactgacca gaatcaggt gagcctgact tgtctcgtca aggattcta cccaagcgac | 1140 |
| atcgccgtgg agtgggaatc caacggccaa ccagagaaca actacaagac cacccccacca | 1200 |
| gtcctggact ctgatgggag cttttttcctg tattccaagc tgacagtgga caagtctcgg | 1260 |
| tggcaacagg gcaacgtgtt cagctgctcc gtgatgcatg aagccctgca taaccactat | 1320 |
| acccagaaaa gcctcagcct gtcccccggg aaataatgaa ttc | 1363 |

US 11,795,230 B2

ANTI-CD27 ANTIBODIES AND USE THEREOF

CROSS-REFERENCE TO RELATED APPLICATIONS

This application is a National Stage Application and claims priority under 35 U.S.C. § 371 to Patent Cooperation Treaty application PCT/CN2018/083095, filed Apr. 13, 2018. Priority is claimed to this application and the disclosure of this prior application is considered part of the disclosure of this application and to the extent allowed the entire contents of the aforementioned application is incorporated herein.

SEQUENCE LISTING

This application incorporates by reference in its entirety the Sequence Listing entitled "262790-474754_Seq_Listing_2020-10-12_ST25.txt", is 141,120 bytes in size and was created on Oct. 12, 2020, and filed electronically herewith.

BACKGROUND

CD27 is a member of the TNF receptor family and belongs to type I transmembrane glycoprotein. CD27 presents on the cell surface as a pair of disulfide-linked homodimers (van Lier et al., 1987). Unlike other TNF receptor family members, CD27 is constitutively expressed on the surface of T cells, NK cells and some memory B cells (van Lier et al., 1987; Sugita et al., 1992; Xiao et al., 2004). When T cells are activated, the expression of CD27 is up-regulated, thereby having a synergistic co-stimulatory effect on the activation of prion cells.

CD70, as a ligand of CD27, interacts with CD27 and recruits intracellular TRAF protein to the intracellular domain of CD27, thereby activating downstream signals, including activation of canonical and non-canonical NF-κB signaling pathways and JNK signaling pathways. It plays an important role in the proliferation, activation and cytotoxicity of CD8$^+$ T cells (Carr et al., 2006; Rowley and Al-Shamkhani, 2004; Taraban et al., 2006). In addition to expression on normal cells, CD27 is also highly expressed in B-cell lymphomas and B-cell chronic lymphocytic leukemia cells (EA et al., 1995).

Previous studies have shown that agonistic antibodies of CD27 could enhance the killing ability of T cells in many mouse tumor models and have anti-tumor activities (Li-zhen He et al., 2013). However, there is still a strong need for CD27 antibodies having better affinity and/or activities.

SUMMARY

The present disclosure provides an antibody, or an antigen binding fragment or variant thereof, which is capable of binding to CD27 and could exhibit at least one of the following properties: 1) having a high affinity to CD27; 2) specifically binding to human CD27 and monkey CD27; 3) capable of activating and/or increasing CD27 mediated NF-κB activity; 4) capable of stimulating CD4$^+$ and/or CD8$^+$ T cell proliferation; 5) capable of stimulating secretion of IFN-γ by CD4$^+$ and/or CD8$^+$ T cells; 6) having a relatively high stability; and 7) staying as dimers in solutions during prolonged storage. In addition, the present disclosure also provides a method for preparing and/or using the antibody, or the antigen binding fragment or variant thereof.

In one aspect, the present disclosure provides an antibody, or an antigen binding fragment or variant thereof. The antibody, or its fragment or variant could bind to CD27 and exhibit at least one of the following properties: 1) specifically binds to CD27, and does not substantially bind to CD137, OX40 or GITR; 2) binds to CD27 with a K$_D$ of 10$^{-8}$ M or less; 3) activates and/or increases CD27 mediated NF-κB activity, as shown in Luciferase Reporter Assay; 4) stimulates CD4$^+$ and/or CD8$^+$ T cell proliferation; 5) binds to human CD27 expressed on a cell surface; 6) binds to monkey CD27 expressed on a cell surface; 7) stimulates secretion of IFN-γ by CD4$^+$ and/or CD8$^+$ T cells; 8) has a T$_m$ of at least 60° C. as tested by DSC; 9) shows a relative decrease of dimerization of less than about 5% in SEC-HPLC analysis when dissolved in a PBS solution at a concentration of about 10 mg/ml, with a pH of about 7.4, under 45° C., during a course of about 30 days; and 10) shows a change of concentration of less than about 20% when dissolved in a PBS solution at a concentration of about 8-12 mg/ml, with a pH of about 7.4, under 45° C., during a course of about 30 days.

In some embodiments, the antibody is selected from the group consisting of: a monoclonal antibody, a chimeric antibody, a humanized antibody, a fully human antibody and a bispecific antibody.

In some embodiments, the antigen binding fragment is selected from the group consisting of: a Fab fragment, a Fab' fragment, a F(ab')2 fragment, a F(ab)2 fragment, a Fv fragment, and an ScFv.

In some embodiments, the variant is selected from the group consisting of: 1) a polypeptide different from the antibody or antigen binding fragment thereof by an addition, deletion or substitution of one or more amino acid; and 2) a polypeptide having a sequence identity of at least 80% with the antibody or antigen binding fragment thereof.

In some embodiments, the antibody or the antigen binding fragment or variant thereof competes with a reference antibody for binding to CD27. The reference antibody may comprise: 1) light chain CDR1-3 comprising an amino acid sequence as set forth in SEQ ID NO: 8-10 respectively, and heavy chain CDR 1-3 comprising an amino acid sequence as set forth in SEQ ID NO: 5-7 respectively; 2) light chain CDR1-3 comprising an amino acid sequence as set forth in SEQ ID NO: 18-20 respectively, and heavy chain CDR 1-3 comprising an amino acid sequence as set forth in SEQ ID NO: 15-17 respectively; 3) light chain CDR1-3 comprising an amino acid sequence as set forth in SEQ ID NO: 28-30 respectively, and heavy chain CDR 1-3 comprising an amino acid sequence as set forth in SEQ ID NO: 25-27 respectively; 4) light chain CDR1-3 comprising an amino acid sequence as set forth in SEQ ID NO: 38-40 respectively, and heavy chain CDR 1-3 comprising an amino acid sequence as set forth in SEQ ID NO: 35-37 respectively; 5) light chain CDR1-3 comprising an amino acid sequence as set forth in SEQ ID NO: 48-50 respectively, and heavy chain CDR 1-3 comprising an amino acid sequence as set forth in SEQ ID NO: 45-47 respectively; 6) light chain CDR1-3 comprising an amino acid sequence as set forth in SEQ ID NO: 58-60 respectively, and heavy chain CDR 1-3 comprising an amino acid sequence as set forth in SEQ ID NO: 55-57 respectively; 7) light chain CDR1-3 comprising an amino acid sequence as set forth in SEQ ID NO: 68-70 respectively, and heavy chain CDR 1-3 comprising an amino acid sequence as set forth in SEQ ID NO: 65-67 respectively; 8) light chain CDR1-3 comprising an amino acid sequence as set forth in SEQ ID NO: 78-80 respectively, and heavy chain CDR 1-3 comprising an amino acid sequence as set forth in SEQ ID NO: 75-77 respectively; 9) light chain CDR1-3 comprising an amino acid sequence as set forth in SEQ ID NO: 88-90 respectively, and heavy chain CDR 1-3 comprising an amino acid sequence as set forth in SEQ ID NO: 85-87 respectively; 10) a light chain variable region comprising an amino acid sequence as set forth in SEQ ID NO: 3, and a heavy chain variable region comprising an amino acid sequence as set forth in SEQ ID NO: 1; 11) a light chain variable region comprising an amino acid sequence as set forth in SEQ ID NO: 13, and a heavy chain variable region comprising an amino acid sequence as set forth in SEQ ID NO: 11; 12) a light chain variable region comprising an amino acid sequence as set forth in SEQ ID NO: 23, and a heavy chain variable region comprising an amino acid sequence as set forth in SEQ ID NO: 21; 13) a light chain variable region comprising an amino acid sequence as set forth in SEQ ID NO: 33, and a heavy chain variable region comprising an amino acid sequence as set forth in SEQ ID NO: 31; 14) a light chain variable region comprising an amino acid sequence as set forth in SEQ ID NO: 43, and a heavy chain variable region comprising an amino acid sequence as set forth in SEQ ID NO: 41; 15) a light chain variable region comprising an amino acid sequence as set forth in SEQ ID NO: 53, and a heavy chain variable region comprising an amino acid sequence as set forth in SEQ ID NO: 51; 16) a light chain variable region comprising an amino acid sequence as set forth in SEQ ID NO: 63, and a heavy chain variable region comprising an amino acid sequence as set forth in SEQ ID NO: 61; 17) a light chain variable region comprising an amino acid sequence as set forth in SEQ ID NO: 73, and a heavy chain variable region comprising an amino acid sequence as set forth in SEQ ID NO: 71; 18) a light chain variable region comprising an amino acid sequence as set forth in SEQ ID NO: 83, and a heavy chain variable region comprising an amino acid sequence as set forth in SEQ ID NO: 81; 19) a light chain variable region comprising an amino acid sequence as set forth in SEQ ID NO: 91, and a heavy chain variable region comprising an amino acid sequence as set forth in SEQ ID NO: 115; 20) a light chain variable region comprising an amino acid sequence as set forth in SEQ ID NO: 91, and a heavy chain variable region comprising an amino acid sequence as set forth in SEQ ID NO: 107; 21) a light chain variable region comprising an amino acid sequence as set forth in SEQ ID NO: 91, and a heavy chain variable region comprising an amino acid sequence as set forth in SEQ ID NO: 95; 22) a light chain variable region comprising an amino acid sequence as set forth in SEQ ID NO: 91, and a heavy chain variable region comprising an amino acid sequence as set forth in SEQ ID NO: 99; 23) a light chain variable region comprising an amino acid sequence as set forth in SEQ ID NO: 91, and a heavy chain variable region comprising an amino acid sequence as set forth in SEQ ID NO: 111; 24) a light chain variable region comprising an amino acid sequence as set forth in SEQ ID NO: 91, and a heavy chain variable region comprising an amino acid sequence as set forth in SEQ ID NO: 103; 25) a light chain variable region comprising an amino acid sequence as set forth in SEQ ID NO: 91, and a heavy chain variable region comprising an amino acid sequence as set forth in SEQ ID NO: 113; 26) a light chain variable region comprising an amino acid sequence as set forth in SEQ ID NO: 91, and a heavy chain variable region comprising an amino acid sequence as set forth in SEQ ID NO: 105; 27) a light chain variable region comprising an amino acid sequence as set forth in SEQ ID NO: 91, and a heavy chain variable region comprising an amino acid sequence as set forth in SEQ ID NO: 93; 28) a light chain variable region comprising an amino acid sequence as set forth in SEQ ID NO: 91, and a heavy chain variable region comprising an amino acid sequence as set forth in SEQ ID NO: 97; 29) a light chain variable region comprising an amino acid sequence as set forth in SEQ ID NO: 91, and a heavy chain variable region comprising an amino acid sequence as set forth in SEQ ID NO: 109; or 30) a light chain variable region comprising an amino acid sequence as set forth in SEQ ID NO: 91, and a heavy chain variable region comprising an amino acid sequence as set forth in SEQ ID NO: 101.

In some embodiments, the antibody comprises a light chain or a fragment thereof. The light chain or a fragment thereof may comprise a light chain CDR1, and the light chain CDR1 comprises an amino acid sequence selected from SEQ ID NO: 8, 18, 28, 38, 48, 58, 68, 78 and 88. In some embodiments, the light chain or a fragment thereof comprises a light chain CDR2, and the light chain CDR2 comprises an amino acid sequence selected from SEQ ID NO: 9, 19, 29, 39, 49, 59, 69, 79 and 89. In some embodiments, the light chain or a fragment thereof comprises a light chain CDR3, and the light chain CDR3 comprises an amino acid sequence selected from SEQ ID NO: 10, 20, 30, 40, 50, 60, 70, 80 and 90.

In some embodiments, the light chain or a fragment thereof comprises a light chain variable region, and the light chain variable region comprises an amino acid sequence selected from SEQ ID NO: 3, 13, 23, 33, 43, 53, 63, 73, 83 and 91.

In some embodiments, the light chain or a fragment thereof comprises a light chain constant region, and the light chain constant region comprises a human Igκ constant region.

In some embodiments, the light chain or a fragment thereof comprises an amino acid sequence selected from SEQ ID NO: 117, 119, 121, 123, 125, 127, 129, 131 and 133.

In some embodiments, the antibody comprises a heavy chain or a fragment thereof. The heavy chain or a fragment thereof may comprise a heavy chain CDR1, and the heavy chain CDR1 comprises an amino acid sequence selected from SEQ ID NO: 5, 15, 25, 35, 45, 55, 65, 75 and 85. In some embodiments, the heavy chain or a fragment thereof comprises a heavy chain CDR2, and the heavy chain CDR2 comprises an amino acid sequence selected from SEQ ID NO: 6, 16, 26, 36, 46, 56, 66, 76 and 86. In some embodiments, the heavy chain or a fragment thereof comprises a heavy chain CDR3, and the heavy chain CDR3 comprises an amino acid sequence selected from SEQ ID NO: 7, 17, 27, 37, 47, 57, 67, 77 and 87.

In some embodiments, the heavy chain or a fragment thereof comprises a heavy chain variable region, and the heavy chain variable region comprises an amino acid sequence selected from SEQ ID NO: 1, 11, 21, 31, 41, 51, 61, 71, 81, 93, 95, 97, 99, 101, 103, 105, 107, 109, 111, 113 and 115.

In some embodiments, the heavy chain or a fragment thereof comprises a heavy chain constant region, and the heavy chain constant region comprises a human IgG constant region. In some embodiments, the human IgG constant region comprises an IgG1 constant region.

In some embodiments, the heavy chain or a fragment thereof comprises an amino acid sequence selected from SEQ ID NO: 118, 120, 122, 124, 126, 128, 130, 132 and 134.

In some embodiments, the CD27 is selected from the group consisting of: a human CD27, a mouse CD27 and a monkey CD27.

In some embodiments, the antibody or the antigen binding fragment or variant thereof comprises: 1) light chain CDR1-3 comprising an amino acid sequence as set forth in SEQ ID NO: 8-10 respectively, and heavy chain CDR 1-3 comprising an amino acid sequence as set forth in SEQ ID NO: 5-7 respectively; 2) light chain CDR1-3 comprising an amino acid sequence as set forth in SEQ ID NO: 18-20 respectively, and heavy chain CDR 1-3 comprising an amino acid sequence as set forth in SEQ ID NO: 15-17 respectively; 3) light chain CDR1-3 comprising an amino acid sequence as set forth in SEQ ID NO: 28-30 respectively, and heavy chain CDR 1-3 comprising an amino acid sequence as set forth in SEQ ID NO: 25-27 respectively; 4) light chain CDR1-3 comprising an amino acid sequence as set forth in SEQ ID NO: 38-40 respectively, and heavy chain CDR 1-3 comprising an amino acid sequence as set forth in SEQ ID NO: 35-37 respectively; 5) light chain CDR1-3 comprising an amino acid sequence as set forth in SEQ ID NO: 48-50 respectively, and heavy chain CDR 1-3 comprising an amino acid sequence as set forth in SEQ ID NO: 45-47 respectively; 6) light chain CDR1-3 comprising an amino acid sequence as set forth in SEQ ID NO: 58-60 respectively, and heavy chain CDR 1-3 comprising an amino acid sequence as set forth in SEQ ID NO: 55-57 respectively; 7) light chain CDR1-3 comprising an amino acid sequence as set forth in SEQ ID NO: 68-70 respectively, and heavy chain CDR 1-3 comprising an amino acid sequence as set forth in SEQ ID NO: 65-67 respectively; 8) light chain CDR1-3 comprising an amino acid sequence as set forth in SEQ ID NO: 78-80 respectively, and heavy chain CDR 1-3 comprising an amino acid sequence as set forth in SEQ ID NO: 75-77 respectively; 9) light chain CDR1-3 comprising an amino acid sequence as set forth in SEQ ID NO: 88-90 respectively, and heavy chain CDR 1-3 comprising an amino acid sequence as set forth in SEQ ID NO: 85-87 respectively; 10) a light chain variable region comprising an amino acid sequence as set forth in SEQ ID NO: 3, and a heavy chain variable region comprising an amino acid sequence as set forth in SEQ ID NO: 1; 11) a light chain variable region comprising an amino acid sequence as set forth in SEQ ID NO: 13, and a heavy chain variable region comprising an amino acid sequence as set forth in SEQ ID NO: 11; 12) a light chain variable region comprising an amino acid sequence as set forth in SEQ ID NO: 23, and a heavy chain variable region comprising an amino acid sequence as set forth in SEQ ID NO: 21; 13) a light chain variable region comprising an amino acid sequence as set forth in SEQ ID NO: 33, and a heavy chain variable region comprising an amino acid sequence as set forth in SEQ ID NO: 31; 14) a light chain variable region comprising an amino acid sequence as set forth in SEQ ID NO: 43, and a heavy chain variable region comprising an amino acid sequence as set forth in SEQ ID NO: 41; 15) a light chain variable region comprising an amino acid sequence as set forth in SEQ ID NO: 53, and a heavy chain variable region comprising an amino acid sequence as set forth in SEQ ID NO: 51; 16) a light chain variable region comprising an amino acid sequence as set forth in SEQ ID NO: 63, and a heavy chain variable region comprising an amino acid sequence as set forth in SEQ ID NO: 61; 17) a light chain variable region comprising an amino acid sequence as set forth in SEQ ID NO: 73, and a heavy chain variable region comprising an amino acid sequence as set forth in SEQ ID NO: 71; 18) a light chain variable region comprising an amino acid sequence as set forth in SEQ ID NO: 83, and a heavy chain variable region comprising an amino acid sequence as set forth in SEQ ID NO: 81; 19) a light chain variable region comprising an amino acid sequence as set forth in SEQ ID NO: 91, and a heavy chain variable region comprising an amino acid sequence as set forth in SEQ ID NO: 115; 20) a light chain variable region comprising an amino acid sequence as set forth in SEQ ID NO: 91, and a heavy chain variable region comprising an amino acid sequence as set forth in SEQ ID NO: 107; 21) a light chain variable region comprising an amino acid sequence as set forth in SEQ ID NO: 91, and a heavy chain variable region comprising an amino acid sequence as set forth in SEQ ID NO: 95; 22) a light chain variable region comprising an amino acid sequence as set forth in SEQ ID NO: 91, and a heavy chain variable region comprising an amino acid sequence as set forth in SEQ ID NO: 99; 23) a light chain variable region comprising an amino acid sequence as set forth in SEQ ID NO: 91, and a heavy chain variable region comprising an amino acid sequence as set forth in SEQ ID NO: 111; 24) a light chain variable region comprising an amino acid sequence as set forth in SEQ ID NO: 91, and a heavy chain variable region comprising an amino acid sequence as set forth in SEQ ID NO: 103; 25) a light chain variable region comprising an amino acid sequence as set forth in SEQ ID NO: 91, and a heavy chain variable region comprising an amino acid sequence as set forth in SEQ ID NO: 113; 26) a light chain variable region comprising an amino acid sequence as set forth in SEQ ID NO: 91, and a heavy chain variable region comprising an amino acid sequence as set forth in SEQ ID NO: 105; 27) a light chain variable region comprising an amino acid sequence as set forth in SEQ ID NO: 91, and a heavy chain variable region comprising an amino acid sequence as set forth in SEQ ID NO: 93; 28) a light chain variable region comprising an amino acid sequence as set forth in SEQ ID NO: 91, and a heavy chain variable region comprising an amino acid sequence as set forth in SEQ ID NO: 97; 29) a light chain variable region comprising an amino acid sequence as set forth in SEQ ID NO: 91, and a heavy chain variable region comprising an amino acid sequence as set forth in SEQ ID NO: 109; or 30) a light chain variable region comprising an amino acid sequence as set forth in SEQ ID NO: 91, and a heavy chain variable region comprising an amino acid sequence as set forth in SEQ ID NO: 101.

In another aspect, the present disclosure provides a fusion protein comprising the antibody or the antigen binding fragment or variant thereof according to the present disclosure.

In another aspect, the present disclosure provides isolated nucleic acid molecule or molecules, encoding for the antibody or the antigen binding fragment or variant thereof according to the present disclosure, or the fusion protein according to the present disclosure.

In another aspect, the present disclosure provides vector or vectors, comprising the isolated nucleic acid molecule or molecules according to the present disclosure.

In another aspect, the present disclosure provides a cell, comprising the isolated nucleic acid molecule or molecules or the vector or vectors according to the present disclosure.

In another aspect, the present disclosure provides a method for producing the antibody or the antigen binding fragment or variant thereof or the fusion protein according to the present disclosure, comprising culturing the cell according to the present disclosure under conditions enabling expression of said antibody or said antigen binding fragment or variant thereof, or said fusion protein.

In some embodiments, the method further comprises harvesting the antibody or the antigen binding fragment or variant thereof according to the present disclosure, or the fusion protein according to the present disclosure.

In another aspect, the present disclosure provides a composition, comprising the antibody or the antigen binding fragment or variant thereof, the fusion protein, the isolated nucleic acid molecule or molecules, the vector or vectors, and/or the cell according to the present disclosure, and optionally a pharmaceutically acceptable excipient.

In another aspect, the present disclosure provides a use of the antibody or the antigen binding fragment or variant thereof, the fusion protein, the isolated nucleic acid molecule or molecules, the vector or vectors, and/or the cell according to the present disclosure in the manufacture of a medicament for preventing and/or treating cancer.

In another aspect, the present disclosure provides a use of the antibody or the antigen binding fragment or variant thereof, or the fusion protein according to the present disclosure in the manufacture of an agent for determining the presence and/or amount of CD27 in a sample.

In another aspect, the present disclosure provides a method for preventing and/or treating cancer in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure.

In another aspect, the present disclosure provides a method for inducing or enhancing an immune response in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure.

In some embodiments, the immune response is mediated by T cells.

In another aspect, the present disclosure provides a method for stimulating the proliferation of T cells, comprising administering to the T cells an effective amount of the antibody or the antigen binding fragment or variant thereof, the fusion protein, the isolated nucleic acid molecule or molecules, the vector or vectors, and/or the cell according to the present disclosure.

In another aspect, the present disclosure provides a method for activating a CD27 mediated signaling or for increasing an activity of the signaling in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure.

In another aspect, the present disclosure provides a method for determining the presence and/or amount of CD27 in a sample, comprising: a) contacting the sample with the antibody or the antigen binding fragment or variant thereof, or the fusion protein according to the present disclosure; and b) determining the presence and/or amount of the antibody, the antigen binding fragment or variant thereof, or the fusion protein bound to the sample.

In another aspect, the present disclosure provides the antibody or the antigen binding fragment or variant thereof, the fusion protein, the isolated nucleic acid molecule or molecules, the vector or vectors, or the cell according to the present disclosure, for a) preventing and/or treating cancer, b) inducing or enhancing an immune response, c) stimulating the proliferation of T cells, d) activating a CD27 mediated signaling or increasing an activity of the signaling, and/or e) determining the presence and/or amount of CD27 in a sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the application are set forth with particularity in the appended claims. A better understanding of the features and advantages of the present application will be obtained by reference to the following detailed description that sets forth illustrative embodiments, in which the principles of the application are employed, and the accompanying drawings (also "figure" and "FIG." herein), of which:

DETAILED DESCRIPTION

Figure 1A:
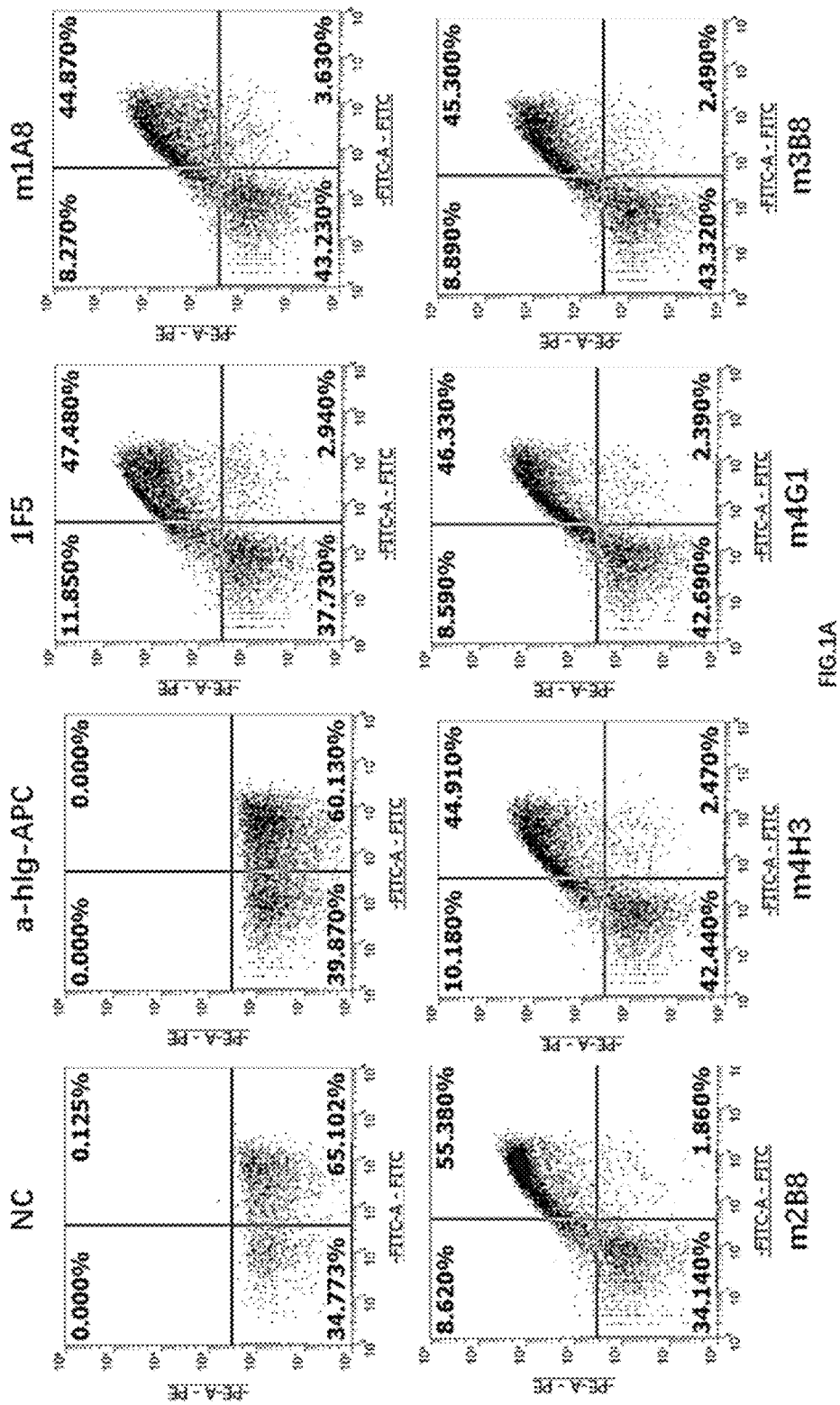
FIGS. 1A-1B illustrate binding of the anti-CD27 antibodies of the present disclosure to cell surface CD27, as detected by FACS.

While various embodiments of the application have been shown and described herein, it will be obvious to those skilled in the art that such embodiments are provided by way of example only. Numerous variations, changes, and substitutions may occur to those skilled in the art without departing from the application. It should be understood that various alternatives to the embodiments of the application described herein may be employed.

The term "antibody", as used herein, generally refers to an immunoglobulin molecule usually composed of two identical pairs of polypeptide chains each having one "light" (L) chain and one "heavy" (H) chain. The light chains of an antibody can be classified as κ and λ light chains. The heavy chains can be classified as μ, δ, γ, α or ε, and the isotypes of an antibody are defined as IgM, IgD, IgG, IgA and IgE, respectively. Within the light and heavy chains, the variable and constant regions are joined by a "J" region of about 12 or more amino acids, and the heavy chains further comprise a "D" region of about 3 or more amino acids. Each heavy chain consists of a heavy chain variable region (VH) and a heavy chain constant region (CH). The heavy chain constant region consists of three domains (CH1, CH2 and CH3). Each light chain consists of a light chain variable region (VL) and a light chain constant region (CL). The light chain constant region consists of one domain, CL. The constant region of an antibody may mediate binding of the immunoglobulin to the host tissue or factor, including various cells of the immune system (e.g., effector cells) and the first component (Clq) of the classical complement system. The VH and VL regions can also be subdivided into regions with high variability known as complementarity determining regions (CDRs) interspersed with more conserved regions known as framework regions (FRs). Each VH and VL consists of 3 CDRs and 4 FRs arranged from N-terminal to C-terminal in the following order: FR1, CDR1, FR2, CDR2, FR3, CDR3, FR4. The variable regions (VH and VL) of each heavy/light chain pair form the antibody binding site, respectively. Distribution of amino acids to regions or domains follows the definition of Kabat Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. The amino acid positions described in the present invention are based on an online comparison of abysis tools and do not represent actual positions in the amino acid sequence. The term "antibody" is not limited by any antibody-producing method. For example, it includes recombinant antibodies, monoclonal antibodies, and polyclonal antibodies. Antibodies may be antibodies of different isotypes, e.g., IgG (e.g., IgG1, IgG2, IgG3 or IgG4 subtype), IgA1, IgA2, IgD, IgE or IgM antibody.

The term "antigen binding fragment", as used herein, generally refers to one or more fragments of a full-length antibody that retains the ability to bind the same antigen to which the antibody binds (e.g., CD27) and competes against an intact antibody for an antigen specific binding. Antigen binding fragment can be produced by recombinant DNA techniques or by enzymatic or chemical cleavage of intact antibodies. In some cases, the antigen binding site includes Fab, Fab", F(ab')2, F (ab)2, Fd, Fv, dAb and complementarity determining region (CDR) fragments, single chain antibodies (e.g., scFv), chimeric antibodies, diabodies, and polypeptides that comprise at least a portion of an antibody that is sufficient to confer specific antigen-binding ability to the polypeptide.

The term "variant", as used herein, generally refers to a protein that differs from a parent molecule (e.g., polypeptide) by at least one amino acid. A variant may refer to the molecule itself, a composition comprising the molecule. It may also refer to the amino acid sequence of the molecule, when such a molecule is a polypeptide or protein. In some cases, a variant differs from its parent molecule (e.g., a protein) by an addition, deletion or substitution of one or more amino acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 amino acid. In some cases, the variant may possess at least about 80% (e.g., at least 85%, at least 90%, at least 91%, at least 92%, at least 93%, at least 94%, at least 95%, at least 96%, at least 97%, at least 98%, at least 99% or higher) sequence homology with the amino acid sequence of its parent molecule.

The term "CD27", as used herein, generally refers to the protein CD27 or a nucleic acid molecule encoding it. CD27 is a member of the tumor necrosis factor receptor superfamily. It binds to ligand CD70 and plays a key role in regulating B-cell activation and immunoglobulin synthesis. CD27 transduces signals that lead to the activation of NF-κB and MAPK8/JNK.

The term "binding specificity", as used herein, generally refers to an ability of one substance to bind another substance specifically, and not easily to bind any other substance at random. For example, one protein may bind to another protein specifically due to their specific structures. For example, a targeting moiety may exhibit binding specificity to a corresponding tumor antigen.

The term "not substantially", as used herein, generally refers to little or almost no binding to a particular substance. For example, very few or almost no (e.g., less than 10%, less than 9%, less than 8%, less than 7%, less than 6%, less than 5%, less than 4%, less than 3%, less than 2%, less than 1%, less than 0.5%, less than 0.1%, or less than 0.01%) antibody, or the antigen binding fragment or variant thereof according to the present application binds to CD137, OX40 or GITR.

The term "CD137", as used herein, generally refers to the protein CD137 or a nucleic acid molecule encoding it. CD137 is a member of the tumor necrosis factor (TNF) receptor family. CD137 is a co-stimulatory immune checkpoint molecule, and it is also known as 4-1BB, TNFRSF9 and ILA. CD137 can be expressed by activated T cells, in addition, dendritic cells, B cells, follicular dendritic cells, natural killer cells, granulocytes and cells of blood vessel walls at sites of inflammation may also express it.

The term "OX40", as used herein, generally refers to the protein OX40 or a nucleic acid molecule encoding it. OX40 is also known as tumor necrosis factor receptor superfamily member 4 (TNFRSF4), or CD134. OX40 is a secondary co-stimulatory immune checkpoint molecule. OX40L binds to OX40 receptors on T-cells, preventing them from dying and subsequently increasing cytokine production. OX40 has a critical role in the maintenance of an immune response beyond the first few days and onwards to a memory response due to its ability to enhance survival. OX40 also plays a crucial role in both Th1 and Th2 mediated reactions in vivo.

The term "GITR", as used herein, generally refers to glucocorticoid-induced TNFR-related protein, or tumor necrosis factor receptor superfamily member 18 (TNFRSF18). In humans, it is encoded by the TNFRSF18 gene. GITR is a co-stimulatory immune checkpoint molecule. It has been shown to be involved in inhibiting the suppressive activity of T-regulatory cells and extending the survival of T-effector cells. In mouse models, GITR was initially noted to be selectively enriched on the surface of regulatory T cells.

The term "$K_D$", as used herein, generally refers to dissociation constant, a specific type of equilibrium constant that measures the propensity of a larger object to separate (dissociate) reversibly into smaller components, as when a complex falls apart into its component molecules. The dissociation constant is the inverse of the association constant. In the specific case of antibodies (Ab) binding to antigen (Ag), usually the term affinity constant refers to the association constant. This chemical equilibrium is also the ratio of the on-rate ($k_{forward}$) and off-rate ($k_{back}$) constants. Two antibodies can have the same affinity, but one may have both a high on- and off-rate constant, while the other may have both a low on- and off-rate constant.

The term "CD27 mediated NF-κB activity", as used herein, generally refers to noncanonical nuclear factor-κB (NF-κB) signaling pathway mediated by CD27, which mediates activation of the p52/RelB NF-κB complex and, thereby, regulates specific immunological processes. This NF-κB pathway relies on the inducible processing of NF-κB2 precursor protein, p100, as opposed to the degradation of IκBα in the canonical NF-κB pathway. A central signaling component of the noncanonical NF-κB pathway is NF-κB-inducing kinase (NIK), which functions together with a downstream kinase, inhibitor of NF-κB kinase α (IKKα), to induce phosphorylation-dependent ubiquitination and processing of p100. Under normal conditions, NIK is targeted for continuous degradation by a tumor necrosis factor (TNF) receptor-associated factor-3 (TRAF3)-dependent E3 ubiquitin ligase. In response to signals mediated by a subset of TNF receptor superfamily members, NIK becomes stabilized as a result of TRAF3 degradation, leading to the activation of noncanonical NF-κB. It is found that a specific subset of TNFR superfamily members mediates induction of noncanonical NF-κB signaling; these include LTβR, CD40, BAFFR, RANK, TNFR2, CD27, etc.

The term "$T_m$", as used herein, generally refers to a midpoint value of a stability curve (melting temperature, also known as the temperature of hydrophobic exposure, $T_h$). It may be obtained by gradually increasing the temperature to unfold the protein and measuring the fluorescence at each point. The higher the $T_m$, the more stable a protein is.

The term "dimerization", as used herein, generally refers to the process of dimer formation. A dimer is an oligomer consisting of two monomers associated with each other by bonds that can be either covalent or non-covalent. When the two monomers are identical, the dimer is a homodimer; when the two monomers are not identical, the dimer is a heterodimer.

The term "monoclonal antibody", as used herein, generally refers to antibodies that are made by identical immune cells that are all clones of a unique parent cell. Monoclonal antibodies can have monovalent affinity, in that they bind to the same epitope (the part of an antigen that is recognized by the antibody). It has become an important tool in biochemistry, molecular biology, and medicine. Several monoclonal antibody technologies had been developed recently, such as phage display, single B cell culture, single cell amplification from various B cell populations and single plasma cell interrogation technologies.

The term "chimeric antibody", as used herein, generally refers to an antibody in which the Variable (V) region of light and heavy chains is of mouse origin, while the Constant (C) region is of human origin, so that nearly two-thirds of the entire antibody molecule is of human origin, which greatly reduces the immunogenicity degree of mouse-origin proteins compared to the original mouse monoclonal antibody. In general, the chimeric antibody retains the specificity and affinity of the original mouse monoclonal antibody, and HAMA response is also significantly reduced.

The term "humanized antibody", as used herein, generally refers to antibodies from non-human species whose protein sequences have been modified to increase their similarity to antibody variants produced naturally in humans. Humanization can be necessary when the process of developing a specific antibody involves generation in a non-human immune system (such as that in mice). The protein sequences of antibodies produced in this way are partially distinct from homologous antibodies occurring naturally in humans and are therefore potentially immunogenic when administered to human patients. The protein sequence of a humanized antibody is essentially identical to that of a human variant, despite the non-human origin of some of its complementarity determining region (CDR) segments responsible for the ability of the antibody to bind to its target antigen.

The term "fully human antibody", as used herein, generally refers to an antibody with fully human amino acid sequence derived antibody region therapeutics where antigen specificity has been selected either in vivo by the use of genetically modified mice or by antibody engineering processes combined with screening. Fully human and humanized antibodies carry a lower risk for inducing immune responses in humans than mouse or chimeric antibodies.

The term "bispecific antibody", as used herein, generally refers to an artificial protein that can simultaneously bind to two different types of antigen. The main types of manufacturing methods are quadromas, chemical conjugation, and genetic recombination. IgG-like format retains the traditional monoclonal antibody (mAb) structure of two Fab arms and one Fc region, except the two Fab sites bind different antigens. Each heavy and light chain pair is from a unique mAb. The Fc region made from the two heavy chains forms the third binding site. Non-IgG-like format includes chemically linked Fabs, consisting of only the Fab regions, and various types of bivalent and trivalent single-chain variable fragments (scFvs). There are also fusion proteins mimicking the variable domains of two antibodies. Bispecific antibodies have a higher cytotoxic potential and bind to antigens that are expressed relatively weakly with a lower effective dose. Additionally, targeting more than one molecule can be useful to circumvent the regulation of parallel pathways and avoid resistance to the treatment.

The term "Fab fragment", as used herein, generally refers to a portion (such as an antigen-binding fragment) of an immunoglobulin molecule. An Fab fragment may comprise one light chain and part of a heavy chain with a single antigen-binding site. A Fab fragment may be obtained by papain digestion of an immunoglobulin molecule. For example, a Fab fragment may be composed of one constant and one variable domain of each of the heavy and the light chain. The variable domain may contain the paratope (the antigen-binding site), comprising a set of complementarity determining regions, at the amino terminal end of the immunoglobulin molecule. The enzyme papain may be used to cleave an immunoglobulin molecule into two Fab fragments and one Fc fragment. The enzyme pepsin cleaves below the hinge region, so a F(ab')2 fragment and a pFc' fragment is formed. Divalent F(ab)2 or F(ab')2 fragments have two antigen binding regions that are linked by disulfide bonds. Reduction of F(ab)2 or F(ab')2 fragments produces 2 monovalent Fab or Fab' fragments, which have a free sulfhydryl group that is useful for conjugation to other molecules.

The term "Fv fragment", as used herein, generally refers to the smallest fragment made from enzymatic cleavage of IgG and IgM class antibodies. Fv fragments have the antigen-binding site made of the VH and VL regions, but they lack the CH1 and CL regions. The VH and VL chains are held together in Fv fragments by non-covalent interactions.

The term "ScFv", as used herein, generally refers to a single-chain antibody fragment. An ScFv may refer to a recombinant single chain polypeptide molecule in which light and heavy chain variable regions of an antibody are connected by a peptide linker. Single chain antibodies (ScFv) generally do not include portions of the Fc region of antibodies that are involved in effector functions and are thus naked antibodies, although methods are known for adding such regions to known ScFv molecules if desired. See Helfrich et al., A rapid and versatile method for harnessing ScFv antibody fragments with various biological functions. J Immunol Methods 237: 131-145 (2000) and de Haard et al., Creating and engineering human antibodies for immunotherapy. Advanced Drug Delivery Reviews 31:5-31 (1998).

The term "IgG", as used herein, generally refers to a subtype of an antibody. Each IgG has two antigen binding sites. Representing approximately 75% of serumantibodies in humans, IgG is the most common type of antibody found in the circulation. The recognized immunoglobulin genes include the κ, λ, α, γ (IgG1, IgG2, IgG3, IgG4).

The term "fusion protein", as used herein, generally refers to a polypeptide that comprises, or alternatively consists of, an amino acid sequence of a polypeptide fused directly or indirectly (e.g., via a linker) to an amino acid sequence of a heterologous polypeptide (i.e., a polypeptide unrelated to the former polypeptide or the domain thereof).

The term "isolated nucleic acid molecule or molecules" as used herein, generally refers to a polymeric form of nucleotides of any length, either deoxyribonucleotides or ribonucleotides, or analogs thereof, isolated from its native environment, or that is artificially synthesized.

The term "vector or vectors" as used herein, generally refers to a nucleic acid vehicle into which a polynucleotide encoding a protein can be inserted and expressed. The genetic material elements carried in the vector can be expressed in a host cell by transforming, transducing, or transfecting the host cell with the vector. Embodiments of vectors include: plasmids; phagemids; cosmos; artificial chromosomes such as yeast artificial chromosomes (YACs), bacterial artificial chromosomes (BACs) or P1-derived artificial chromosomes (PACs); phages such as λ phage or M13 phage and animal viruses. Animal virus used as a carrier include retrovirus (including lentivirus), adenovirus, adeno-associated virus, herpes virus (such as herpes simplex virus), jaundice virus, baculovirus, papilloma virus, papovaviruses (such as SV40). A vector may contain a variety of elements that control expression, including promoter sequences, transcriptional initiation sequences, enhancer sequences, selection elements, and reporter genes. In addition, the vector may also contain an origin of replication. It is also possible that the vector may include components that assist its entry into the cell, such as viral particles, liposomes or protein shells, but not only these substances.

The term "cell" as used herein, generally refers to a cell into which a vector is introduced and includes many cell types such as prokaryotic cells such as Escherichia coli and Bacillus subtilis, fungal cells such as yeast cells or Aspergillus cells, insect cells such as S2 Drosophila cells or Sf9, or animal cells such as fibroblasts, CHO cells, COS cells, NSO cells, HeLa cells, BHK cells, HEK293 cells or human cells.

The term "conditions enabling expression", as used herein, generally refers to conditions enabling the expression of the antibody or the antigen binding fragment or variant thereof of the present application. In some embodiments, the conditions to enable expression include but not limited to incubation time, temperature, and culture medium, and may depend on cell type and may be readily determined by one of ordinary skill in the art. In some embodiments, during the process of producing the antibody or the antigen binding fragment or variant thereof of the present disclosure, the cells are grown in cultures, and in any apparatus that may be used to grow cultures, including fermenters. Cells may be grown as monolayers or attached to a surface. Alternatively, the cells may be grown in suspension. The cells can be grown in a culture medium that is serum-free.

The term "cancer" as used herein, generally refers to a group of diseases involving abnormal cell growth with the potential to invade or spread to other parts of the body. Cancer is fundamentally a disease of tissue growth regulation. In order for a normal cell to transform into a cancer cell, the genes that regulate cell growth and differentiation must be altered. The affected genes are divided into two broad categories. Oncogenes are genes that promote cell growth and reproduction. Tumor suppressor genes are genes that inhibit cell division and survival. Malignant transformation can occur through the formation of novel oncogenes, the inappropriate over-expression of normal oncogenes, or by the under-expression or disabling of tumor suppressor genes. Typically, changes in multiple genes are required to transform a normal cell into a cancer cell. Cancers are classified by the type of cell that include carcinoma, sarcoma, lymphoma and leukemia, germ cell tumor and blastoma.

The term "T cell" as used herein, generally refers to a type of lymphocyte (a subtype of white blood cell) that plays a central role in cell-mediated immunity. T cells can be distinguished from other lymphocytes, such as B cells and natural killer cells, by the presence of a T-cell receptor on the cell surface. They are called T cells because they mature in the thymus from thymocytes. The majority of human T cells rearrange their alpha and beta chains on the cell receptor and are termed alpha beta T cells (αβ T cells) and are part of the adaptive immune system. Specialized gamma delta T cells, (a small minority of T cells in the human body, more frequent in ruminants), have invariant T-cell receptors with limited diversity, that can effectively present antigens to other T cells and are considered to be part of the innate immune system.

The term "pharmaceutically acceptable excipient", as used herein, generally refers to any and all solvents, dispersion media, coatings, isotonic and absorption delaying agents, etc., that are compatible with pharmaceutical administration.

The term "about", as used herein, generally refers to an approximation to a given value that would reasonably be inferred based on the ordinary skill in the art, including equivalents and approximations due to the experimental and/or measurement conditions for such given value. For example, it may refer to a value that is no more than 10% above or below the value being modified by the term. For example, the term "about 5 µg/kg" means a range of 4.5 µg/kg to 5.5 µg/kg. As another example, "about 1 hour" means a range of 48 minutes to 72 minutes.

The term "effective amount", as used herein, generally refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific component, the route of administration, the rate of clearance, the duration of treatment, the age, body weight, sex, diet, and general health of the subject, and other related factors.

The term "binding specificity" as used herein, generally refers to the ability to specifically bind (e.g., immunoreact with) a given target (while not binding or substantially not binding a non-target). An antibody (or its antigen binding fragment or variant) of the present disclosure may be monospecific and contain one or more binding sites which specifically bind a target or may be multispecific (e.g., bispecific or trispecific) and contain two or more binding sites which specifically bind the same or different targets.

The term "modification" as used herein, generally refers to any manipulation of the peptide backbone (e.g. amino acid sequence) or any post-translational modifications (e.g. glycosylation) of a polypeptide. For example, a modification is in comparison to the sequence of a corresponding wild-type polypeptide. A modification may be a substitution, an addition, and/or a deletion of one or more amino acids (e.g., 1, 2, 3, 4, 5, 6, 7, 8, 9, 10, or more).

The term "amino acid substitution" as used herein, generally refers to that one amino acid at a specific position of a polypeptide is replaced by another amino acid.

The term "EU index of the KABAT number" as used herein, generally refers to the index of the EU number corresponding to the amino acid sequence according to Kabat et al. (1971) Ann. NY Acad, Sci. 190:382-391 and Kabat, E. A., et al. (1991) Sequences of Proteins of Immunological Interest, Fifth Edition, U.S. Department of Health and Human Services, NIH Publication No. 91-3242.

The term "isolated polynucleotide" as used herein, generally refers to a polymeric form of nucleotides of any length, either deoxyribonucleotides or ribonucleotides, or analogs thereof, isolated from its native environment, or that is artificially synthesized.

CD27 Antibody, the Antigen Binding Fragment or Variant Thereof

In one aspect, the present disclosure provides an antibody, or an antigen binding fragment or variant thereof, which may bind to CD27.

The antibody, or the antigen binding fragment or variant thereof may specifically bind to CD27, and does not substantially bind to CD137, OX40 or GITR. For example, the antibody, or the antigen binding fragment or variant thereof may bind to CD27 with a percentage of at least 30% (for example, at least 35%, at least 40%, at least 45%, at least 50%, at least 55%, at least 60%, at least 65%, at least 70%, at least 75%, at least 80%, at least 85%, at least 90% or more), as measured by FACS. In addition, the antibody, or the antigen binding fragment or variant thereof may bind to OX40 with a percentage of at most 5% (for example, at most 4.5%, at most 4%, at most 3.5%, at most 3%, at most 2.5%, at most 2%, at most 1.5%, at most 1%, at most 0.5%, or less), as measured by FACS. In addition, the antibody, or the antigen binding fragment or variant thereof may bind to CD137 with a percentage of at most 5% (for example, at most 4.5%, at most 4%, at most 3.5%, at most 3%, at most 2.5%, at most 2%, at most 1.5%, at most 1%, at most 0.5%, or less), as measured by FACS. In addition, the antibody, or the antigen binding fragment or variant thereof may bind to GITR with a percentage of at most 5% (for example, at most 4.5%, at most 4%, at most 3.5%, at most 3%, at most 2.5%, at most 2%, at most 1.5%, at most 1%, at most 0.5%, or less), as measured by FACS.

The antibody, or the antigen binding fragment or variant thereof may bind to CD27 with a $K_D$ of $10^{-7}$ M or less, e.g., with a $K_D$ of $10^{-8}$ M or less, of $9\times10^{-9}$ M or less, of $8\times10^{-9}$ M or less, of $7\times10^{-9}$ M or less, of $6\times10^{-9}$ M or less, of $5\times10^{-9}$ M or less, of $4\times10^{-9}$ M or less, of $3\times10^{-9}$ M or less, of $2\times10^{-9}$ M or less, of $1\times10^{-9}$ M or less, of $9\times10^{-10}$ M or less, of $8\times10^{-10}$ M or less, of $7\times10^{-10}$ M or less, of $5\times10^{-10}$ M or less, or of $1\times10^{-10}$ M or less.

The antibody, or the antigen binding fragment or variant thereof may activate and/or increase CD27 mediated NF-κB activity. For example, as shown in Luciferase Reporter Assay.

The antibody, or the antigen binding fragment or variant thereof may stimulate CD4$^+$ and/or CD8$^+$ T cell proliferation. For example, the proliferation rate of the CD4$^+$ and/or CD8$^+$ T cell may be enhanced by 20% or more, 30% or more, 40% or more, 50% or more, 60% or more, 70% or more, 80% or more, 90% or more, 100% or more, 150% or more, 200% or more, 250% or more, 300% or more, 350% or more, or 400% or more.

The antibody, or the antigen binding fragment or variant thereof may bind to human CD27 expressed on a cell surface. The antibody, or the antigen binding fragment or variant thereof may also bind to monkey CD27 expressed on a cell surface.

The antibody, or the antigen binding fragment or variant thereof may stimulate secretion of IFN-γ by CD4$^+$ and/or CD8$^+$ T cells. For example, the secretion of IFN-γ may be enhanced to at least 200 pg/mL, at least 400 pg/mL, at least 600 pg/mL, at least 800 pg/mL, at least 1000 pg/mL, at least 2000 pg/mL, at least 2500 pg/mL, at least 3000 pg/mL, at least 3500 pg/mL, or at least 4000 pg/mL or more.

The antibody, or the antigen binding fragment or variant thereof may have a $T_m$ of at least 50° C. (for example, at least 55° C., at least 59° C., at least 60° C., at least 61° C., at least 62° C., at least 63° C., at least 64° C., at least 65° C., at least 66° C., at least 67° C., at least 68° C., at least 69° C., at least 70° C. or higher), for example as tested by DSC.

The antibody, or the antigen binding fragment or variant thereof may show a relative decrease of dimerization of less than about 10% (e.g., less than about 9%, less than about 8%, less than about 7%, less than about 6%, less than about 5.5%, less than about 5%, less than about 4%, less than about 3%, less than about 2%, less than about 1% or less) in SEC-HPLC analysis. For example, when dissolved in a PBS solution at a concentration of 5-15 mg/ml (for example, about 5-14 mg/ml, about 5-13 mg/ml, about 5-12 mg/ml, about 5-11 mg/ml, about 5-10 mg/ml, about 5-9 mg/ml, about 5-8 mg/ml, about 5-7 mg/ml, about 5-6 mg/ml). The pH may be about 6.5-about 8.5 (e.g., about 6.8-about 8.5, about 7.0-about 8.5, about 7.1-about 8.5, about 7.2-about 8.5, about 7.3-about 8.5, about 7.4-about 8.5, about 7.5-about 8.5, about 7.6-about 8.5, about 7.7-about 8.5, about 7.8-about 8.5, about 7.9-about 8.5, or about 8.0-about 8.5). May be under a temperature of about 30° C. to about 70° C. (e.g., about 35° C. to about 70° C., about 40° C. to about 70° C., about 41° C. to about 70° C., about 42° C. to about 70° C., about 43° C. to about 70° C., about 44° C. to about 70° C., about 45° C. to about 70° C., about 46° C. to about 70° C., about 47° C. to about 70° C., about 48° C. to about 70° C., about 49° C. to about 70° C., about 50° C. to about 70° C., about 55° C. to about 70° C., about 60° C. to about 70° C., or about 65° C. to about 70° C.). During a course of about 10-45 days (e.g., about 15-45 days, about 20-45 days, about 25-45 days, about 26-45 days, about 27-45 days, about 28-45 days, about 29-45 days, about 30-45 days, about 31-45 days, about 32-45 days, about 33-45 days, about 34-45 days, about 35-45 days, or about 40-45 days).

In the present disclosure, it is preferable for the antibody, or the antigen binding fragment or variant thereof to remain in the form of a dimer (e.g., instead of monomer, trimer or other multimers).

The antibody, or the antigen binding fragment or variant thereof may show a change of concentration of less than about 30% (e.g., less than about 25%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, or less than about 5% or less) when dissolved in a solvent solution (e.g., a PBS solution). The antibody, or the antigen binding fragment or variant thereof may be dissolved at a concentration of about 5-15 mg/ml (e.g., about 6-15 mg/ml, about 7-15 mg/ml, about 8-15 mg/ml, about 9-15 mg/ml, about 10-15 mg/ml, about 11-15 mg/ml, about 12-15 mg/ml, about 13-15 mg/ml, or about 14-15 mg/ml, such as about 8-12 mg/ml, about 9-11 mg/ml, or about 9.5-10.5 mg/ml). The pH may be about 6.5-about 8.5 (e.g., about 6.8-about 8.5, about 7.0-about 8.5, about 7.1-about 8.5, about 7.2-about 8.5, about 7.3-about 8.5, about 7.4-about 8.5, about 7.5-about 8.5, about 7.6-about 8.5, about 7.7-about 8.5, about 7,8-about 8.5, about 7.9-about 8.5, or about 8.0-about 8.5). May be under a temperature of about 30° C. to about 70° C. (e.g., about 35° C. to about 70° C., about 40° C. to about 70° C., about 41° C. to about 70° C., about 42° C. to about 70° C., about 43° C. to about 70° C., about 44° C. to about 70° C., about 45° C. to about 70° C., about 46° C. to about 70° C., about 47° C. to about 70° C., about 48° C. to about 70° C., about 49° C. to about 70° C., about 50° C. to about 70° C., about 55° C. to about 70° C., about 60° C. to about 70° C., or about 65° C. to about 70° C.). During a course of about 10-45 days (e.g., about 15-45 days, about 20-45 days, about 25-45 days, about 26-45 days, about 27-45 days, about 28-45 days, about 29-45 days, about 30-45 days, about 31-45 days, about 32-45 days, about 33-45 days, about 34-45 days, about 35-45 days, or about 40-45 days).

The antibody according to the present disclosure may be selected from the group consisting of: a monoclonal antibody, a chimeric antibody, a humanized antibody, a fully human antibody and a bispecific antibody.

The antigen binding fragment according to the present disclosure may be selected from the group consisting of: a Fab fragment, a Fab' fragment, a F(ab)2 fragment, a F(ab')2 fragment, a Fv fragment, and an ScFv.

In some cases, the variant may be a polypeptide different from the antibody or antigen binding fragment thereof according to the present disclosure by an addition, deletion or substitution of one or more amino acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 amino acids.

In some cases, the variant may be a polypeptide having a sequence identity of at least 80% (e.g., at least 85%, at least 90%, at least 91%, at least 92%, at least 93%, at least 94%, at least 95%, at least 96%, at least 97%, at least 98%, at least 99% or higher) with the antibody or antigen binding fragment thereof according to the present disclosure.

In the present disclosure, the antibody or the antigen binding fragment or variant thereof may compete with a reference antibody for binding to CD27.

In some cases, the reference antibody comprises light chain CDR1-3 and heavy chain CDR1-3, the light chain CDR1 may comprise an amino acid sequence as set forth in SEQ ID NO: 8, the light chain CDR2 may comprise an amino acid sequence as set forth in SEQ ID NO: 9, the light chain CDR3 may comprise an amino acid sequence as set forth in SEQ ID NO: 10, the heavy chain CDR1 may comprise an amino acid sequence as set forth in SEQ ID NO: 5, the heavy chain CDR2 may comprise an amino acid sequence as set forth in SEQ ID NO: 6, and the heavy chain CDR3 may comprise an amino acid sequence as set forth in SEQ ID NO: 7.

In some cases, the reference antibody comprises light chain CDR1-3 and heavy chain CDR1-3, the light chain CDR1 may comprise an amino acid sequence as set forth in SEQ ID NO: 18, the light chain CDR2 may comprise an amino acid sequence as set forth in SEQ ID NO: 19, the light chain CDR3 may comprise an amino acid sequence as set forth in SEQ ID NO: 20, the heavy chain CDR1 may comprise an amino acid sequence as set forth in SEQ ID NO: 15, the heavy chain CDR2 may comprise an amino acid sequence as set forth in SEQ ID NO: 16, and the heavy chain CDR3 may comprise an amino acid sequence as set forth in SEQ ID NO: 17.

In some cases, the reference antibody comprises light chain CDR1-3 and heavy chain CDR1-3, the light chain CDR1 may comprise an amino acid sequence as set forth in SEQ ID NO: 28, the light chain CDR2 may comprise an amino acid sequence as set forth in SEQ ID NO: 29, the light chain CDR3 may comprise an amino acid sequence as set forth in SEQ ID NO: 30, the heavy chain CDR1 may comprise an amino acid sequence as set forth in SEQ ID NO: 25, the heavy chain CDR2 may comprise an amino acid sequence as set forth in SEQ ID NO: 26, and the heavy chain CDR3 may comprise an amino acid sequence as set forth in SEQ ID NO: 27.

In some cases, the reference antibody comprises light chain CDR1-3 and heavy chain CDR1-3, the light chain CDR1 may comprise an amino acid sequence as set forth in SEQ ID NO: 38, the light chain CDR2 may comprise an amino acid sequence as set forth in SEQ ID NO: 39, the light chain CDR3 may comprise an amino acid sequence as set forth in SEQ ID NO: 40, the heavy chain CDR1 may comprise an amino acid sequence as set forth in SEQ ID NO: 35, the heavy chain CDR2 may comprise an amino acid sequence as set forth in SEQ ID NO: 36, and the heavy chain CDR3 may comprise an amino acid sequence as set forth in SEQ ID NO: 37.

In some cases, the reference antibody comprises light chain CDR1-3 and heavy chain CDR1-3, the light chain CDR1 may comprise an amino acid sequence as set forth in SEQ ID NO: 48, the light chain CDR2 may comprise an amino acid sequence as set forth in SEQ ID NO: 49, the light chain CDR3 may comprise an amino acid sequence as set forth in SEQ ID NO: 50, the heavy chain CDR1 may comprise an amino acid sequence as set forth in SEQ ID NO: 45, the heavy chain CDR2 may comprise an amino acid sequence as set forth in SEQ ID NO: 46, and the heavy chain CDR3 may comprise an amino acid sequence as set forth in SEQ ID NO: 47.

In some cases, the reference antibody comprises light chain CDR1-3 and heavy chain CDR1-3, the light chain CDR1 may comprise an amino acid sequence as set forth in SEQ ID NO: 58, the light chain CDR2 may comprise an amino acid sequence as set forth in SEQ ID NO: 59, the light chain CDR3 may comprise an amino acid sequence as set forth in SEQ ID NO: 60, the heavy chain CDR1 may comprise an amino acid sequence as set forth in SEQ ID NO: 55, the heavy chain CDR2 may comprise an amino acid sequence as set forth in SEQ ID NO: 56, and the heavy chain CDR3 may comprise an amino acid sequence as set forth in SEQ ID NO: 57.

In some cases, the reference antibody comprises light chain CDR1-3 and heavy chain CDR1-3, the light chain CDR1 may comprise an amino acid sequence as set forth in SEQ ID NO: 68, the light chain CDR2 may comprise an amino acid sequence as set forth in SEQ ID NO: 69, the light chain CDR3 may comprise an amino acid sequence as set forth in SEQ ID NO: 70, the heavy chain CDR1 may comprise an amino acid sequence as set forth in SEQ ID NO: 65, the heavy chain CDR2 may comprise an amino acid sequence as set forth in SEQ ID NO: 66, and the heavy chain CDR3 may comprise an amino acid sequence as set forth in SEQ ID NO: 67.

In some cases, the reference antibody comprises light chain CDR1-3 and heavy chain CDR1-3, the light chain CDR1 may comprise an amino acid sequence as set forth in SEQ ID NO: 78, the light chain CDR2 may comprise an amino acid sequence as set forth in SEQ ID NO: 79, the light chain CDR3 may comprise an amino acid sequence as set forth in SEQ ID NO: 80, the heavy chain CDR1 may comprise an amino acid sequence as set forth in SEQ ID NO: 75, the heavy chain CDR2 may comprise an amino acid sequence as set forth in SEQ ID NO: 76, and the heavy chain CDR3 may comprise an amino acid sequence as set forth in SEQ ID NO: 77.

In some cases, the reference antibody comprises light chain CDR1-3 and heavy chain CDR1-3, the light chain CDR1 may comprise an amino acid sequence as set forth in SEQ ID NO: 88, the light chain CDR2 may comprise an amino acid sequence as set forth in SEQ ID NO: 89, the light chain CDR3 may comprise an amino acid sequence as set forth in SEQ ID NO: 90, the heavy chain CDR1 may comprise an amino acid sequence as set forth in SEQ ID NO: 85, the heavy chain CDR2 may comprise an amino acid sequence as set forth in SEQ ID NO: 86, and the heavy chain CDR3 may comprise an amino acid sequence as set forth in SEQ ID NO: 87.

In some cases, the reference antibody comprises a light chain variable region and a heavy chain variable region, the light chain variable region may comprise an amino acid sequence as set forth in SEQ ID NO: 3, and the heavy chain variable region may comprise an amino acid sequence as set forth in SEQ ID NO: 1.

In some cases, the reference antibody comprises a light chain variable region and a heavy chain variable region, the light chain variable region may comprise an amino acid sequence as set forth in SEQ ID NO: 13, and the heavy chain variable region may comprise an amino acid sequence as set forth in SEQ ID NO: 11.

In some cases, the reference antibody comprises a light chain variable region and a heavy chain variable region, the light chain variable region may comprise an amino acid sequence as set forth in SEQ ID NO: 23, and the heavy chain variable region may comprise an amino acid sequence as set forth in SEQ ID NO: 21.

In some cases, the reference antibody comprises a light chain variable region and a heavy chain variable region, the light chain variable region may comprise an amino acid sequence as set forth in SEQ ID NO: 33, and the heavy chain variable region may comprise an amino acid sequence as set forth in SEQ ID NO: 31.

In some cases, the reference antibody comprises a light chain variable region and a heavy chain variable region, the light chain variable region may comprise an amino acid sequence as set forth in SEQ ID NO: 43, and the heavy chain variable region may comprise an amino acid sequence as set forth in SEQ ID NO: 41.

In some cases, the reference antibody comprises a light chain variable region and a heavy chain variable region, the light chain variable region may comprise an amino acid sequence as set forth in SEQ ID NO: 53, and the heavy chain variable region may comprise an amino acid sequence as set forth in SEQ ID NO: 51.

In some cases, the reference antibody comprises a light chain variable region and a heavy chain variable region, the light chain variable region may comprise an amino acid sequence as set forth in SEQ ID NO: 63, and the heavy chain variable region may comprise an amino acid sequence as set forth in SEQ ID NO: 61.

In some cases, the reference antibody comprises a light chain variable region and a heavy chain variable region, the light chain variable region may comprise an amino acid sequence as set forth in SEQ ID NO: 73, and the heavy chain variable region may comprise an amino acid sequence as set forth in SEQ ID NO: 71.

In some cases, the reference antibody comprises a light chain variable region and a heavy chain variable region, the light chain variable region may comprise an amino acid sequence as set forth in SEQ ID NO: 83, and the heavy chain variable region may comprise an amino acid sequence as set forth in SEQ ID NO: 81.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 115.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 107.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 95.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 99.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 111.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 103.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 113.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 105.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 93.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 97.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 109.

In some cases, the reference antibody comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 101.

In the present disclosure, the antibody, or the antigen binding fragment or variant thereof may comprise an antibody light chain or a fragment thereof.

For example, the antibody light chain or fragment thereof may comprise LCDR1, and the LCDR1 may comprise an amino acid sequence selected from SEQ ID NO: 8, 18, 28, 38, 48, 58, 68, 78 and 88. The antibody light chain or fragment thereof may comprise LCDR2, and the LCDR2 may comprise an amino acid sequence selected from SEQ ID NO: 9, 19, 29, 39, 49, 59, 69, 79 and 89. The antibody light chain or fragment thereof may comprise LCDR3, and the LCDR3 may comprise an amino acid sequence selected from SEQ ID NO: 10, 20, 30, 40, 50, 60, 70, 80 and 90.

Further, the antibody light chain or fragment thereof may comprise a light chain variable region VL, and the light chain variable region VL may comprise an amino acid sequence selected from SEQ ID NO: 3, 13, 23, 33, 43, 53, 63, 73, 83 and 91.

The antibody light chain or the fragment thereof may also comprise a constant region. The light chain constant region may comprise an Igκ constant region, for example, a human Igκ constant region.

In some embodiments, the light chain or the fragment thereof comprises an amino acid sequence selected from SEQ ID NO: 117, 119, 121, 123, 125, 127, 129, 131 and 133.

In the present disclosure, the antibody, or the antigen binding fragment or variant thereof may comprise an antibody heavy chain or a fragment thereof.

For example, the antibody heavy chain or the fragment thereof may comprise HCDR1, and the HCDR1 may comprise an amino acid sequence selected from SEQ ID NO: 5, 15, 25, 35, 45, 55, 65, 75 and 85. The antibody heavy chain or the fragment thereof may comprise HCDR2, and the HCDR2 may comprise an amino acid sequence selected from SEQ ID NO: 6, 16, 26, 36, 46, 56, 66, 76 and 86. The antibody heavy chain or the fragment thereof may comprise HCDR3, and the HCDR3 may comprise an amino acid sequence selected from SEQ ID NO: 7, 17, 27, 37, 47, 57, 67, 77 and 87.

Further, the antibody heavy chain or the fragment thereof may comprise a heavy chain variable region VH, and the heavy chain variable region VH may comprise an amino acid sequence selected from SEQ ID NO: 1, 11, 21, 31, 41, 51, 61, 71, 81, 93, 95, 97, 99, 101, 103, 105, 107, 109, 111, 113 and 115.

The antibody heavy chain or the fragment thereof may also comprise a human constant region. For example, the human constant region may comprise a constant region of human IgG. For example, the IgG constant region may comprise the constant region of human IgG1.

In some embodiments, the heavy chain or the fragment thereof comprises an amino acid sequence selected from SEQ ID NO: 118, 120, 122, 124, 126, 128, 130, 132 and 134.

In the present disclosure, the CD27 may be selected from the group consisting of: a human CD27, a mouse CD27 and a monkey CD27.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 8, the light chain CDR2 may comprise an amino acid sequence as set forth in SEQ ID NO: 9, the light chain CDR3 may comprise an amino acid sequence as set forth in SEQ ID NO: 10, the heavy chain CDR1 may comprise an amino acid sequence as set forth in SEQ ID NO: 5, the heavy chain CDR2 may comprise an amino acid sequence as set forth in SEQ ID NO: 6, and the heavy chain CDR3 may comprise an amino acid sequence as set forth in SEQ ID NO: 7.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 18, the light chain CDR2 may comprise an amino acid sequence as set forth in SEQ ID NO: 19, the light chain CDR3 may comprise an amino acid sequence as set forth in SEQ ID NO: 20, the heavy chain CDR1 may comprise an amino acid sequence as set forth in SEQ ID NO: 15, the heavy chain CDR2 may comprise an amino acid sequence as set forth in SEQ ID NO: 16, and the heavy chain CDR3 may comprise an amino acid sequence as set forth in SEQ ID NO: 17.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 28, the light chain CDR2 may comprise an amino acid sequence as set forth in SEQ ID NO: 29, the light chain CDR3 may comprise an amino acid sequence as set forth in SEQ ID NO: 30, the heavy chain CDR1 may comprise an amino acid sequence as set forth in SEQ ID NO: 25, the heavy chain CDR2 may comprise an amino acid sequence as set forth in SEQ ID NO: 26, and the heavy chain CDR3 may comprise an amino acid sequence as set forth in SEQ ID NO: 27.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 38, the light chain CDR2 may comprise an amino acid sequence as set forth in SEQ ID NO: 39, the light chain CDR3 may comprise an amino acid sequence as set forth in SEQ ID NO: 40, the heavy chain CDR1 may comprise an amino acid sequence as set forth in SEQ ID NO: 35, the heavy chain CDR2 may comprise an amino acid sequence as set forth in SEQ ID NO: 36, and the heavy chain CDR3 may comprise an amino acid sequence as set forth in SEQ ID NO: 37.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 48, the light chain CDR2 may comprise an amino acid sequence as set forth in SEQ ID NO: 49, the light chain CDR3 may comprise an amino acid sequence as set forth in SEQ ID NO: 50, the heavy chain CDR1 may comprise an amino acid sequence as set forth in SEQ ID NO: 45, the heavy chain CDR2 may comprise an amino acid sequence as set forth in SEQ ID NO: 46, and the heavy chain CDR3 may comprise an amino acid sequence as set forth in SEQ ID NO: 47.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 58, the light chain CDR2 may comprise an amino acid sequence as set forth in SEQ ID NO: 59, the light chain CDR3 may comprise an amino acid sequence as set forth in SEQ ID NO: 60, the heavy chain CDR1 may comprise an amino acid sequence as set forth in SEQ ID NO: 55, the heavy chain CDR2 may comprise an amino acid sequence as set forth in SEQ ID NO: 56, and the heavy chain CDR3 may comprise an amino acid sequence as set forth in SEQ ID NO: 57.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 68, the light chain CDR2 may comprise an amino acid sequence as set forth in SEQ ID NO: 69, the light chain CDR3 may comprise an amino acid sequence as set forth in SEQ ID NO: 70, the heavy chain CDR1 may comprise an amino acid sequence as set forth in SEQ ID NO: 65, the heavy chain CDR2 may comprise an amino acid sequence as set forth in SEQ ID NO: 66, and the heavy chain CDR3 may comprise an amino acid sequence as set forth in SEQ ID NO: 67.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 78, the light chain CDR2 may comprise an amino acid sequence as set forth in SEQ ID NO: 79, the light chain CDR3 may comprise an amino acid sequence as set forth in SEQ ID NO: 80, the heavy chain CDR1 may comprise an amino acid sequence as set forth in SEQ ID NO: 75, the heavy chain CDR2 may comprise an amino acid sequence as set forth in SEQ ID NO: 76, and the heavy chain CDR3 may comprise an amino acid sequence as set forth in SEQ ID NO: 77.

In the present disclosure, the antibody or the antigen binding fragment thereof may comprise light chain CDR1-3 and heavy chain CDR1-3, the light chain CDR1 may comprise an amino acid sequence as set forth in SEQ ID NO: 88, the light chain CDR2 may comprise an amino acid sequence as set forth in SEQ ID NO: 89, the light chain CDR3 may comprise an amino acid sequence as set forth in SEQ ID NO: 90, the heavy chain CDR1 may comprise an amino acid sequence as set forth in SEQ ID NO: 85, the heavy chain CDR2 may comprise an amino acid sequence as set forth in SEQ ID NO: 86, and the heavy chain CDR3 may comprise an amino acid sequence as set forth in SEQ ID NO: 87.

In some cases, the antibody or the antigen binding fragment thereof comprises a light chain variable region and a heavy chain variable region, the light chain variable region may comprise an amino acid sequence as set forth in SEQ ID NO: 3, and the heavy chain variable region may comprise an amino acid sequence as set forth in SEQ ID NO: 1.

In some cases, the antibody or the antigen binding fragment thereof comprises a light chain variable region and a heavy chain variable region, the light chain variable region may comprise an amino acid sequence as set forth in SEQ ID NO: 13, and the heavy chain variable region may comprise an amino acid sequence as set forth in SEQ ID NO: 11.

In some cases, the antibody or the antigen binding fragment thereof comprises a light chain variable region and a heavy chain variable region, the light chain variable region may comprise an amino acid sequence as set forth in SEQ ID NO: 23, and the heavy chain variable region may comprise an amino acid sequence as set forth in SEQ ID NO: 21.

In some cases, the antibody or the antigen binding fragment thereof comprises a light chain variable region and a heavy chain variable region, the light chain variable region may comprise an amino acid sequence as set forth in SEQ ID NO: 33, and the heavy chain variable region may comprise an amino acid sequence as set forth in SEQ ID NO: 31.

In some cases, the antibody or the antigen binding fragment thereof comprises a light chain variable region and a heavy chain variable region, the light chain variable region may comprise an amino acid sequence as set forth in SEQ ID NO: 43, and the heavy chain variable region may comprise an amino acid sequence as set forth in SEQ ID NO: 41.

In some cases, the antibody or the antigen binding fragment thereof comprises a light chain variable region and a heavy chain variable region, the light chain variable region may comprise an amino acid sequence as set forth in SEQ ID NO: 53, and the heavy chain variable region may comprise an amino acid sequence as set forth in SEQ ID NO: 51.

In some cases, the antibody or the antigen binding fragment thereof comprises a light chain variable region and a heavy chain variable region, the light chain variable region may comprise an amino acid sequence as set forth in SEQ ID NO: 63, and the heavy chain variable region may comprise an amino acid sequence as set forth in SEQ ID NO: 61.

In some cases, the antibody or the antigen binding fragment thereof comprises a light chain variable region and a heavy chain variable region, the light chain variable region may comprise an amino acid sequence as set forth in SEQ ID NO: 73, and the heavy chain variable region may comprise an amino acid sequence as set forth in SEQ ID NO: 71.

In some cases, the antibody or the antigen binding fragment thereof comprises a light chain variable region and a heavy chain variable region, the light chain variable region may comprise an amino acid sequence as set forth in SEQ ID NO: 83, and the heavy chain variable region may comprise an amino acid sequence as set forth in SEQ ID NO: 81.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 115.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 107.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 95.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 99.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 111.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 103.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 113.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 105.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 93.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 97.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 109.

In some cases, the antibody or the antigen binding fragment thereof comprises a light chain variable region and a heavy chain variable region, the light chain variable region may comprise an amino acid sequence as set forth in SEQ ID NO: 91, and the heavy chain variable region may comprise an amino acid sequence as set forth in SEQ ID NO: 101.

For example, the antibody or the antigen binding fragment thereof may comprise LCDR1-3 and HCDR1-3 that are the same as those of the antibody m2E7. The LCDR1-3 of the antibody m2E7 are as set forth in SEQ ID NO: 28-30, respectively, and the HCDR1-3 of the antibody m2E7 are as set forth in SEQ ID NO: 25-27, respectively.

As another example, the antibody or the antigen binding fragment thereof may comprise LCDR1-3 and HCDR1-3 that are the same as those of the antibody m2B8. The LCDR1-3 of the antibody m2B8 are as set forth in SEQ ID NO: 18-20, respectively, and the HCDR1-3 of the antibody m2B8 are as set forth in SEQ ID NO: 15-17, respectively.

As another example, the antibody or the antigen binding fragment thereof may comprise LCDR1-3 and HCDR1-3 that are the same as those of the antibody m4H3. The LCDR1-3 of the antibody m4H3 are as set forth in SEQ ID NO: 68-70, respectively, and the HCDR1-3 of the antibody m4H3 are as set forth in SEQ ID NO: 65-67, respectively.

As another example, the antibody or the antigen binding fragment thereof may comprise LCDR1-3 and HCDR1-3 that are the same as those of the antibody m3E7. The LCDR1-3 of the antibody m3E7 are as set forth in SEQ ID NO: 38-40, respectively, and the HCDR1-3 of the antibody m3E7 are as set forth in SEQ ID NO: 35-37, respectively.

As another example, the antibody or the antigen binding fragment thereof may comprise LCDR1-3 and HCDR1-3 that are the same as those of the antibody m1A8. The LCDR1-3 of the antibody m1A8 are as set forth in SEQ ID NO: 8-10, respectively, and the HCDR1-3 of the antibody m1A8 are as set forth in SEQ ID NO: 5-7, respectively.

As another example, the antibody or the antigen binding fragment thereof may comprise LCDR1-3 and HCDR1-3 that are the same as those of the antibody m4G1. The LCDR1-3 of the antibody m4G1 are as set forth in SEQ ID NO: 58-60, respectively, and the HCDR1-3 of the antibody m4G1 are as set forth in SEQ ID NO: 55-57, respectively.

As another example, the antibody or the antigen binding fragment thereof may comprise LCDR1-3 and HCDR1-3 that are the same as those of the antibody m2G3. The LCDR1-3 of the antibody m2G3 are as set forth in SEQ ID NO: 78-80, respectively, and the HCDR1-3 of the antibody m2G3 are as set forth in SEQ ID NO: 75-77, respectively.

As another example, the antibody or the antigen binding fragment thereof may comprise LCDR1-3 and HCDR1-3 that are the same as those of the antibody m2F11. The LCDR1-3 of the antibody m2F11 are as set forth in SEQ ID NO: 88-90, respectively, and the HCDR1-3 of the antibody m2F11 are as set forth in SEQ ID NO: 85-87, respectively.

As another example, the antibody or the antigen binding fragment thereof may comprise LCDR1-3 and HCDR1-3 that are the same as those of the antibody m3B8. The LCDR1-3 of the antibody m3B8 are as set forth in SEQ ID NO: 48-50, respectively, and the HCDR1-3 of the antibody m3B8 are as set forth in SEQ ID NO: 45-47, respectively.

As another example, the antibody or the antigen binding fragment thereof may comprise a light chain variable region and a heavy chain variable region that are the same as those of the antibody m2E7. The light chain variable region of the antibody m2E7 is as set forth in SEQ ID NO: 21, and the heavy chain variable region of the antibody m2E7 is as set forth in SEQ ID NO: 23.

As another example, the antibody or the antigen binding fragment thereof may comprise a light chain variable region and a heavy chain variable region that are the same as those of the antibody d16647. The light chain variable region of the antibody d16647 is as set forth in SEQ ID NO: 91, and the heavy chain variable region of the antibody d16647 is as set forth in SEQ ID NO: 115.

As another example, the antibody or the antigen binding fragment thereof may comprise a light chain variable region and a heavy chain variable region that are the same as those of the antibody d12996. The light chain variable region of the antibody d12996 is as set forth in SEQ ID NO: 91, and the heavy chain variable region of the antibody d12996 is as set forth in SEQ ID NO: 107.

As another example, the antibody or the antigen binding fragment thereof may comprise a light chain variable region and a heavy chain variable region that are the same as those of the antibody d9419. The light chain variable region of the antibody d9419 is as set forth in SEQ ID NO: 91, and the heavy chain variable region of the antibody d9419 is as set forth in SEQ ID NO: 95.

As another example, the antibody or the antigen binding fragment thereof may comprise a light chain variable region and a heavy chain variable region that are the same as those of the antibody d9424. The light chain variable region of the antibody d9424 is as set forth in SEQ ID NO: 91, and the heavy chain variable region of the antibody d9424 is as set forth in SEQ ID NO: 99.

As another example, the antibody or the antigen binding fragment thereof may comprise a light chain variable region and a heavy chain variable region that are the same as those of the antibody d14822. The light chain variable region of the antibody d14822 is as set forth in SEQ ID NO: 91, and the heavy chain variable region of the antibody d14822 is as set forth in SEQ ID NO: 111.

As another example, the antibody or the antigen binding fragment thereof may comprise a light chain variable region and a heavy chain variable region that are the same as those of the antibody d12674. The light chain variable region of the antibody d12674 is as set forth in SEQ ID NO: 91, and the heavy chain variable region of the antibody d12674 is as set forth in SEQ ID NO: 103.

As another example, the antibody or the antigen binding fragment thereof may comprise a light chain variable region and a heavy chain variable region that are the same as those of the antibody 16647. The light chain variable region of the antibody 16647 is as set forth in SEQ ID NO: 91, and the heavy chain variable region of the antibody 16647 is as set forth in SEQ ID NO: 113.

As another example, the antibody or the antigen binding fragment thereof may comprise a light chain variable region and a heavy chain variable region that are the same as those of the antibody 12996. The light chain variable region of the antibody 12996 is as set forth in SEQ ID NO: 91, and the heavy chain variable region of the antibody 12996 is as set forth in SEQ ID NO: 105.

As another example, the antibody or the antigen binding fragment thereof may comprise a light chain variable region and a heavy chain variable region that are the same as those of the antibody 9419. The light chain variable region of the antibody 9419 is as set forth in SEQ ID NO: 91, and the heavy chain variable region of the antibody 9419 is as set forth in SEQ ID NO: 93.

As another example, the antibody or the antigen binding fragment thereof may comprise a light chain variable region and a heavy chain variable region that are the same as those of the antibody 9424. The light chain variable region of the antibody 9424 is as set forth in SEQ ID NO: 91, and the heavy chain variable region of the antibody 9424 is as set forth in SEQ ID NO: 97.

As another example, the antibody or the antigen binding fragment thereof may comprise a light chain variable region and a heavy chain variable region that are the same as those of the antibody 14822. The light chain variable region of the antibody 14822 is as set forth in SEQ ID NO: 91, and the heavy chain variable region of the antibody 14822 is as set forth in SEQ ID NO: 109.

As another example, the antibody or the antigen binding fragment thereof may comprise a light chain variable region and a heavy chain variable region that are the same as those of the antibody 12674. The light chain variable region of the antibody 12674 is as set forth in SEQ ID NO: 91, and the heavy chain variable region of the antibody 12674 is as set forth in SEQ ID NO: 101.

As another example, the antibody or the antigen binding fragment thereof may comprise a light chain variable region and a heavy chain variable region that are the same as those of the antibody m2B8. The light chain variable region of the antibody m2B8 is as set forth in SEQ ID NO: 13, and the heavy chain variable region of the antibody m2B8 is as set forth in SEQ ID NO: 11.

As another example, the antibody or the antigen binding fragment thereof may comprise a light chain variable region and a heavy chain variable region that are the same as those of the antibody m4H3. The light chain variable region of the antibody m4H3 is as set forth in SEQ ID NO: 63, and the heavy chain variable region of the antibody m4H3 is as set forth in SEQ ID NO: 61.

As another example, the antibody or the antigen binding fragment thereof may comprise a light chain variable region and a heavy chain variable region that are the same as those of the antibody m3E7. The light chain variable region of the antibody m3E7 is as set forth in SEQ ID NO: 33, and the heavy chain variable region of the antibody m3E7 is as set forth in SEQ ID NO: 31.

As another example, the antibody or the antigen binding fragment thereof may comprise a light chain variable region and a heavy chain variable region that are the same as those of the antibody m1A8. The light chain variable region of the antibody m1A8 is as set forth in SEQ ID NO: 3, and the heavy chain variable region of the antibody m1A8 is as set forth in SEQ ID NO: 1.

As another example, the antibody or the antigen binding fragment thereof may comprise a light chain variable region and a heavy chain variable region that are the same as those of the antibody m4G1. The light chain variable region of the antibody m4G1 is as set forth in SEQ ID NO: 53, and the heavy chain variable region of the antibody m4G1 is as set forth in SEQ ID NO: 51.

As another example, the antibody or the antigen binding fragment thereof may comprise a light chain variable region and a heavy chain variable region that are the same as those of the antibody m2G3. The light chain variable region of the antibody m2G3 is as set forth in SEQ ID NO: 73, and the heavy chain variable region of the antibody m2G3 is as set forth in SEQ ID NO: 71.

As another example, the antibody or the antigen binding fragment thereof may comprise a light chain variable region and a heavy chain variable region that are the same as those of the antibody m2F11. The light chain variable region of the antibody m2F11 is as set forth in SEQ ID NO: 83, and the heavy chain variable region of the antibody m2F11 is as set forth in SEQ ID NO: 81.

As another example, the antibody or the antigen binding fragment thereof may comprise a light chain variable region and a heavy chain variable region that are the same as those of the antibody m3B8. The light chain variable region of the antibody m3B8 is as set forth in SEQ ID NO: 43, and the heavy chain variable region of the antibody m3B8 is as set forth in SEQ ID NO: 41.

In some embodiments, the antibody according to the present disclosure is selected from the group consisting of: m2E7, m2B8, m4H3, m3E7, m1A8, m4G1, m2G3, m2F11, m3B8, d16647, d12996, d9419, d9424, d14822, d12674, 16647, 12996, 9419, 9424, 14822, 12674.

In another aspect, the present disclosure provides a fusion protein. The fusion protein may comprise the antibody, or the antigen binding fragment or variant thereof according to the present disclosure.

For example, the fusion protein may comprise one or more additional components, such as other pharmaceutical active components. The additional component may be fused to the antibody, or its antigen binding fragment or variant according to the present disclosure directly or indirectly (e.g., via a linker, such as a peptide linker). The fusion protein may still have at least some of the properties of the antibody, or its antigen binding fragment or variant according to the present disclosure.

Nucleic Acid, Vector, Cell and the Method of Preparation

In another aspect, the present disclosure provides isolated nucleic acid or isolated nucleic acids, encoding for the antibody, the antigen binding fragment or variant thereof, or the fusion protein according to the present disclosure.

The isolated nucleic acids may comprise one or more nucleic acid molecules, with each encoding the antibody of the present disclosure, an antigen binding fragment thereof, or a variant thereof. For example, the isolated nucleic acids may comprise at least two nucleic acid molecules, with one encoding the antibody heavy chain or a fragment/variant thereof, and one encoding the antibody light chain or a fragment/variant thereof. In some cases, the isolated nucleic acids may encode for a fusion protein.

The isolated nucleic acid or isolated nucleic acids may be synthesized using recombinant techniques well known in the art. For example, the isolated nucleic acid or isolated nucleic acids may be synthesized with an automated DNA synthesizer.

Standard recombinant DNA and molecular cloning techniques include those described by Sambrook, Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M et al., *Current Protocols in Molecular Biology*, pub. by Greene Publishing Assoc. and Wiley-Interscience (1987). Briefly, the subject nucleic acids may be prepared from genomic DNA fragments, cDNAs, and RNAs, all of which may be extracted directly from a cell or recombinantly produced by various amplification processes including but not limited to PCR and RT-PCR.

Direct chemical synthesis of nucleic acids typically involves sequential addition of 3'-blocked and 5'-blocked nucleotide monomers to the terminal 5'-hydroxyl group of a growing nucleotide polymer chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. See for example, Matteuci et al., *Tet. Lett.* 521:719 (1980); U.S. Pat. No. 4,500,707 to Caruthers et al.; and U.S. Pat. Nos. 5,436,327 and 5,700,637 to Southern et al.

In another aspect, the present disclosure provides a vector or vectors, comprising the isolated nucleic acid molecule or molecules.

The vector may be any linear nucleic acids, plasmids, phagemids, cosmids, RNA vectors, viral vectors and the like. Non-limiting examples of a viral vector may include a retrovirus, an adenovirus and an adeno-associated virus. In some embodiments, the vector is an expression vector, e.g. a phage display vector.

An expression vector may be suitable for use in particular types of host cells and not others. For example, the expression vector can be introduced into the host organism, which is then monitored for viability and expression of any genes/polynucleotides contained in the vector.

The expression vector may also contain one or more selectable marker genes that, upon expression, confer one or more phenotypic traits useful for selecting or otherwise identifying host cells that carry the expression vector. Non-limiting examples of suitable selectable markers for eukaryotic cells include dihydrofolate reductase and neomycin resistance.

The subject vectors can be introduced into a host cell stably or transiently by a variety of established techniques. For example, one method involves a calcium chloride treatment wherein the expression vector is introduced via a calcium precipitate. Other salts, for example calcium phosphate, may also be used following a similar procedure. In addition, electroporation (that is, the application of current to increase the permeability of cells to nucleic acids) may be used. Other examples of transformation methods include microinjection, DEAE dextran mediated transformation, and heat shock in the presence of lithium acetate. Lipid complexes, liposomes, and dendrimers may also be employed to transfect the host cells.

In another aspect, the present disclosure provides a cell (e.g., an isolated cell, such as a host cell), comprising the isolated nucleic acid molecule or molecules of the present disclosure or the vector or vectors of the present disclosure.

The cell may express the antibody, or the antigen binding fragment or variant thereof of the present disclosure, or the fusion protein of the present disclosure. The cell may be a eukaryotic cell or a prokaryotic cell. An appropriate cell may be transformed or transfected with the nucleic acid(s) or vector(s) of the present disclosure and utilized for the expression and/or secretion of the antibody, the antigen binding fragment or variant thereof, or the fusion protein. For example, the cell may be *E. coli* cells, other bacterial host cells, yeast cells, or various higher eukaryotic cells.

In another aspect, the present disclosure provides a method for producing the antibody, the antigen binding fragment or variant thereof, or the fusion protein of the present disclosure, comprising culturing the cell of the present disclosure under conditions enabling expression of the antibody, the antigen binding fragment or variant thereof, or the fusion protein.

The method may further comprise harvesting the antibody, the antigen binding fragment or variant thereof, or the fusion protein of the present disclosure.

Pharmaceutical Compositions

In another aspect, the present disclosure provides a composition, comprising the antibody, the antigen binding fragment or variant thereof, the vector or vectors, the fusion protein, and/or the isolated nucleic acid molecule or molecules according to the present disclosure, and optionally a pharmaceutically acceptable excipient.

In some embodiments, the pharmaceutical composition further comprises an effective amount of an additional therapeutically active component for cancer treatment. For example, the additional therapeutically active component for cancer treatment may be an agent for chemotherapy. In some embodiments, the agent for chemotherapy is a cytotoxic agent. Each of the active components may be present in the pharmaceutical composition in a pharmaceutically active amount.

Described below are non-limiting exemplary pharmaceutical compositions and methods for preparing the same. The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. In some embodiments, the pharmaceutical composition may be a liquid pharmaceutical composition suitable for oral consumption.

Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods typically include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The antibody, the antigen binding fragment or variant thereof, or the fusion protein of the present disclosure can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

The pharmaceutical compositions of the present disclosure may comprise a therapeutically effective amount of the active agent (e.g., the antibody, the antigen binding fragment or variant thereof, or the fusion protein of the present disclosure). A therapeutically effective amount is an amount of the subject pharmaceutical composition capable of preventing and/or curing (at least partially) a condition or disorder (e.g., cancer) and/or any complications thereof in a subject suffering from or having a risk of developing said condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. In some embodiments, the dosage applied may be from about 3 mg/kg/day to about 3.5 mg/kg/day, from 3.5 mg/kg/day to about 7.2 mg/kg/day, from about 7.2 mg/kg/day to about 11.0 mg/kg/day, from about 11.0 mg/kg/day to about 15.0 mg/kg/day. In some embodiments, the dosage applied is from about 10 mg/kg/day to about 50 mg/kg/day, for example, from about 20 mg to about 50 mg per day, administered twice/day. It shall be understood that these specific doses may be conveniently adjusted by a skilled person in the art (e.g., a doctor or a pharmacist) based on conditions of a specific patient, formulation, and/or disease.

Medical Use and Methods of Treatment

In another aspect, the present disclosure provides a use of the antibody or the antigen binding fragment or variant thereof, the fusion protein, the isolated nucleic acid molecule or molecules, the vector or vectors and/or the cell according to the present disclosure in the manufacture of a medicament for preventing and/or treating cancer.

For example, the cancer may comprise tumor cells with elevated expression of CD27. For example, the cancer may be a hematologic tumor (such as $CD27^+$ lymphomas) or a solid tumor. For example, the cancer may be selected from the group consisting of: renal cell carcinoma, thymic cancer, nasopharyngeal carcinoma, Hodgkin and non-Hodgkin's lymphoma, Waldenstoom giant globulinemia, chronic lymphocytic leukemia, T-cell leukemia, multiple myeloma, EBV related and HTLV-1 related malignancies, pancreatic, laryngocarcinoma, pharynx, melanoma, ovarian cancer, lung cancer (including lung adenocarcinoma), colon cancer, breast cancer and brain cancer.

In another aspect, the present disclosure provides a use of the antibody or the antigen binding fragment or variant thereof, or the fusion protein according to the present disclosure in the manufacture of an agent for determining the presence and/or amount of CD27 in a sample.

In another aspect, the present disclosure provides a method for preventing and/or treating cancer in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure.

In another aspect, the present disclosure provides a method for inducing or enhancing an immune response in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure. For example, the immune response may be mediated by T cells.

In another aspect, the present disclosure provides a method for stimulating the proliferation of T cells, comprising administering to the T cells an effective amount of the antibody or the antigen binding fragment or variant thereof, the fusion protein, the isolated nucleic acid molecule or molecules, the vector or vectors, and/or the cell according to the present disclosure. The method may be an in vitro method.

In another aspect, the present disclosure provides a method for activating a CD27 mediated signaling or for increasing an activity of the signaling in a subject in need thereof, comprising administering to the subject an effective amount of the antibody or the antigen binding fragment or variant thereof, the fusion protein, the isolated nucleic acid molecule or molecules, the vector or vectors, and/or the cell according to the present disclosure.

In another aspect, the present disclosure provides a method for determining the presence and/or amount of CD27 in a sample, comprising: a) contacting the sample with the antibody or the antigen binding fragment or variant thereof, or the fusion protein according to the present disclosure; and b) determining the presence and/or amount of the antibody, the antigen binding fragment or variant thereof, or the fusion protein bound to the sample.

In another aspect, the present disclosure provides the antibody or the antigen binding fragment or variant thereof, the fusion protein, the isolated nucleic acid molecule or molecules, the vector or vectors, or the cell according to the present disclosure, for a) preventing and/or treating cancer, b) inducing or enhancing an immune response, c) stimulating the proliferation of T cells, d) activating a CD27 mediated signaling or increasing an activity of the signaling, and/or e) determining the presence and/or amount of CD27 in a sample.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

The following examples are set forth so as to provide those of ordinary skill in the art with a complete disclosure and description of how to make and use the present application, and are not intended to limit the scope of what the applicants regard as their application nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Expression of Recombinant Human CD27 Protein and Preparation of Related EGFP Cells According to the protein database Uniprot, the amino acid sequence of the extracellular domain of human CD27 (i.e., residues 1 to 192 of P26842) was obtained according to the amino acid sequence of the human CD27 (hCD27, and the accession number in Uniprot is P26842). The amino acid sequence of the extracellular domain of the monkey CD27 (i.e., residues 1 to 192 of F7BYS2) was obtained according to the amino acid sequence of monkey CD27 (RhCD27, and the accession number in Uniprot is F7BYS2). The amino acid sequence of the human IgG1-Fc domain (Fc) (i.e., residues 104 to 330 of P01857) was obtained according to the amino acid sequence of the human immunoglobulin gamma1 (hIgG1, and the accession number in Uniprot is P01857). The amino acid sequence of the mouse IgG1-Fc (muFc) was obtained (i.e., residues 98 to 324 of P01868) was obtained according to the amino acid sequence of mouse immunoglobulin gamma1 (mIgG1, and the accession number in Uniprot is P01868). The corresponding coding DNA sequences were designed with the online tool DNAworks (helixweb.nih.gov/dnaworks), thereby obtaining the corresponding coding sequences for the fusion proteins hCD27-Fc, hCD27-muFc and RhCD27-muFc.

The amino acid sequence of green fluorescence protein EGFP (the accession number is C5MKY7), human CD137 (hCD137, the accession number is Q07011), human OX40 (hOX40, the accession number is P43489), human GITR (hGITR, the accession number is Q9Y5U5), human CD27 (hCD27, the accession number is P26842), murine CD27 (mCD27, the accession number is P41272), and monkey CD27 (RhCD27, the accession number is F7BYS2) were obtained from the Uniprot database. Their corresponding coding DNA sequences were designed with the online tool DNAworks (helixweb.nih.gov/dnaworks), thereby obtaining DNA sequences coding for the following EGFP-fusion proteins, respectively: hCD137-EGFP, hOX40-EGFP, hCD27-EGFP, hGITR-EGFP, mCD27-EGFP, and RhCD27-EGFP.

The synthesized DNA sequences were sub-cloned into the commercially available vector pcDNA4/myc-HisA (Invitrogen, V863-20), after being digested with Fermentas' HindIII and PmeI enzymes. The plasmids were verified by sequencing and the following recombinant plasmids were obtained: pcDNA4-hCD27-hFc, pcDNA4-hCD27-muFc, pcDNA4-RhCD27-muFc, pcDNA4-hOX40-EGFP, pcDNA4-hCD137-EGFP, pcDNA4-mCD27-EGFP, pcDNA4-hCD27-EGFP, pcDNA4-hGITR-EGFP, pcDNA4-mCD27-EGFP and pcDNA4-RhCD27-EGFP.

Then, the recombinant plasmids were introduced into HEK293 (ATCC, CRL-1573™) cells by transfection, the expression of hOX40, hCD137, hGITR, hCD27, mCD27, and RhCD27 was confirmed 48 hours after transfection by fluorescence activated signal sorting (FACS).

The plasmids pcDNA4-hCD27-Fc, pcDNA4-hCD27-muFc and pcDNA4-RhCD27-muFc were transiently introduced into HEK293 cells by transfection, and the corresponding proteins were produced. Briefly, these plasmids were diluted with Freestyle 293 medium and appropriate PEI (polyethyleneimine) solution was added. Then, each plasmid/PEI mixture was added into the cell suspension, and incubated under 37° C., 10% $CO_2$ and 90 rpm. After 5-6 days, the culture supernatant was collected and preliminarily purified by ProteinA affinity chromatography to obtain hCD27-Fc, hCD27-muFc and RhCD27-muFc protein samples. The obtained protein samples were analyzed with SDS-PAGE (FIGS. 12A-12B) and expression of the desired target proteins was confirmed.

Figure 12:
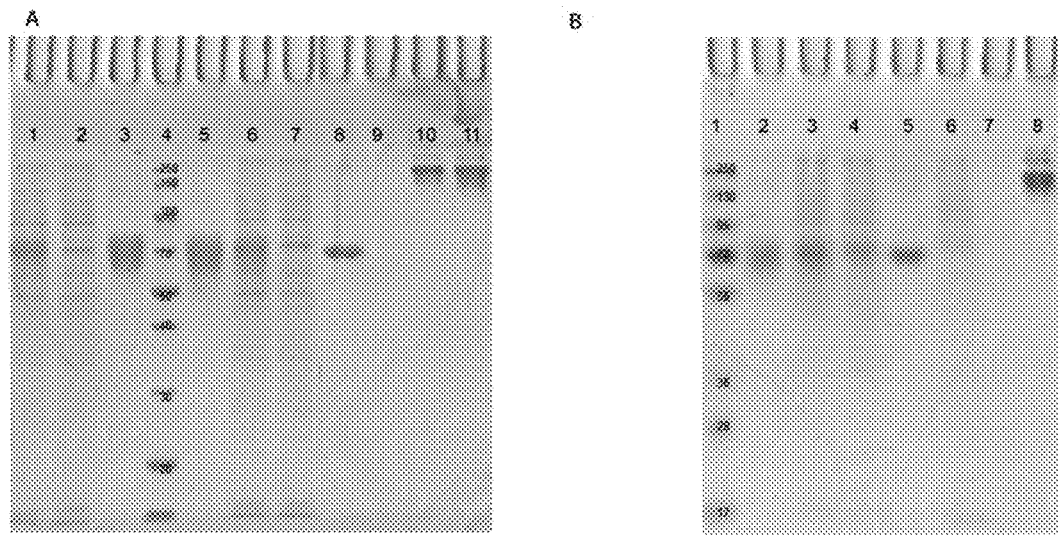
FIGS. 12A-12B illustrate the expression of the recombinant CD27 protein by SDS-PAGE.

FIGS. 12A-12B showed that CD27-Fc, CD27-muFc, RhCD27-muFc was successfully expressed and purified. In FIG. 12A, lane 1 was loaded with CD27-Fc (original sample); lane 2 was loaded with CD27-Fc (flow-through); lane 3 was loaded with CD27-Fc (eluted); lane 4 was loaded with marker (26630); lane 5 was loaded with CD27-muFc (eluted); lane 6 was loaded with CD27-muFc (original sample); lane 7 was loaded with CD27-muFc (flow-through); lane 8 was loaded with 1 µg Std; lane 9 was empty; lane 10 was loaded with CD27-Fc (eluted, non-reducing); and lane 11 was loaded with CD27-Fc (eluted, non-reducing).

In FIG. 12B, lane 1 was loaded with marker (26619); lane 2 was loaded with RhCD27-muFc (eluted); lane 3 was loaded with RhCD27-muFc (original sample); lane 4 was loaded with RhCD27-muFc (flow-through); lane 5 was loaded with 1 µg Std; lane 6 was blank; lane 7 was empty; lane 8 was loaded with RhCD27-muFc (eluted, non-reducing).

Example 2 Anti-CD27 Antibody Obtained from Hybridoma

Mice were immunized with the hCD27-muFc protein prepared as described in Example 1 and antibody titer was determined after three immunizations. The mice showing a high titer were selected for the fourth immunization. Spleen cells were isolated from the mice after the fourth immunization, and the spleen cells were fused with mouse myeloma cells SP2/0. The supernatant obtained from the fused cells was subjected to ELISA binding test, and a total of 400 hybridoma clones capable of binding to CD27 were obtained.

Briefly, the ELISA plate was coated with 2 µg/ml CD27-Fc, 100 µl/well and incubated overnight under 4° C. Then, it was washed once with 10 mM, pH 7.4 PBS/Tween (0.05%), and was blocked with PBST containing 5% skimmed milk powder, incubated at 37° C. for 2 h. After washing the plate for 4 times, the hybridoma supernatant was added and it was incubated at 37° C. for 40 min. The plate was then washed for 4 times, and anti-mouse IgG-HRP-conjugated secondary antibody (Abcam, Cat #ab97040) was added and incubated at 37° C. for 40 min. After washing, the signal was developed with TMB substrate and spectrophotometric analysis was performed at $OD_{450}$. Clones with an OD of above 0.5 were considered positive.

The binding activities and activation abilities of the selected positive clones were examined by FACS, and the antibodies showing an activation activity were selected for further study. The FACS analysis was performed according to instructions. Briefly, $5 \times 10^5$ CD27-EGFP cells prepared in Example 1 were washed twice in PBS, 50 µl hybridoma supernatant as well as 50 µl PBS were added and incubated at 4° C. for 30 min. Then they were washed twice in PBS, and anti-mouse Ig-PE (eBioscience, Cat #2-4010-8) was added and incubated at 4° C. for 30 min, washed twice with PBS, resuspended in 300 µl PBS, and examined with flow cytometry. A total of 300 positive clones were obtained.

50 clones with strong binding affinity were selected for activation assay. The activation assay was performed as follows: 293T-CD27-NF-κB cells were digested with trypsin, after 2-3 mins, DMEM complete medium was added. The cells were gently suspended and transferred to 96-well plates, 100 µl/well. Supernatants from the 50 selected clones were mixed with anti-mouse crosslinking antibody (Jackson ImmunoResearch Laboratories: 115-006-008) and added to a 96-well plate. Complete medium was added to the control group. The cells were lysed after 30 hours and then tested using the luciferase assay system (Promega: E1501). Nine antibodies were selected, sub-cloned, and the clones obtained were sequenced. These nine antibodies were 2E7, 2B8, 4H3, 3E7, 1A8, 4G1, 2G3, 2F11 and 3B8.

After sequencing, the amino acid sequences of the 9 selected antibodies were determined as follows: the amino acid sequence of VL of clone 2E7 is as set forth in SEQ ID NO: 23, the amino acid sequence of VH of clone 2E7 is as set forth in SEQ ID NO: 21. The amino acid sequence of VL of clone 2B8 is as set forth in SEQ ID NO: 13, and the amino acid sequence of VH of clone 2B8 is as set forth in SEQ ID NO: 11. The amino acid sequence of VL of clone 4H3 is as set forth in SEQ ID NO: 63, and the amino acid sequence of VH of clone 4H3 is as set forth in SEQ ID NO: 61. The amino acid sequence of VL of clone 3E7 is as set forth in SEQ ID NO: 33; and the amino acid sequence of VH of clone 3E7 is as set forth in SEQ ID NO: 31. The amino acid sequence of VL of clone 1A8 is as set forth in SEQ ID NO: 3, and the amino acid sequence of VH of clone 1A8 is as set forth in SEQ ID NO: 1. The amino acid sequence of VL of clone 4G1 is as set forth in SEQ ID NO: 53, and the amino acid sequence of VH of clone 4G1 is as set forth in SEQ ID NO: 51. The amino acid sequence of VL of clone 2G3 is as set forth in SEQ ID NO: 73, and the amino acid sequence of VH of clone 2G3 is as set forth in SEQ ID NO: 71. The amino acid sequence of VL of clone 2F11 is as set forth in SEQ ID NO: 83, and the amino acid sequence of VH of clone 2F11 is as set forth in SEQ ID NO: 81. The amino acid sequence of VL of clone 3B8 is as set forth in SEQ ID NO: 43, and the amino acid sequence of VH of clone 3B8 is as set forth in SEQ ID NO: 41.

Example 3 Preparation of Anti-CD27 Chimeric Antibodies

The amino acid sequence of human IgG1 constant region was obtained according to the amino acid sequence of the human immunoglobulin gamma1 (hIgG1, and the accession number in Uniprot is P01857). The corresponding coding nucleic acid sequence was designed using the online tool DNAworks (helixweb.nih.gov/dnaworks). The nucleic acid sequences encoding the VH of the selected antibodies from Example 2 were fused with the human IgG1 constant region sequences, respectively. The obtained fused sequences were then sub-cloned into the vector pcDNA4/myc-HisA to obtain the heavy chain expression plasmids for each antibody.

The amino acid sequence of human Kappa light chain constant region (Igκ) was obtained according to the amino acid sequence of the human immunoglobulin Kappa (the accession number in Uniprot is P01934). The corresponding coding nucleic acid sequence was designed using the online tool DNAworks (helixweb.nih.gov/dnaworks). The nucleic acid sequences encoding for the VL of the selected antibodies from Example 2 were fused with the human Igκ constant region sequences, respectively. The obtained fused sequences were then sub-cloned into the vector pcDNA4/myc-HisA to obtain the light chain expression plasmids for each antibody.

The heavy chain and light chain plasmids obtained as described above were extracted using the plasmid extraction kit (PL14) provided by AidLab. The heavy chain and light chain plasmids were then co-transfected into HEK293 cells for antibody expression. Briefly, the expression plasmids were diluted with Freestyle 293 medium and the PEI (Polyethyleneimine) solution was added. The plasmid/PEI mixture was added to the cell suspension and incubated under 37° C., 10% $CO_2$ at 90 rpm, with 50 µg/L IGF-1 added. After four hours, EX293 medium, 2 mM Glutamine and 50 µg/L IGF-1 were added and incubated under 135 rpm. Twenty-four hours later, 3.8 m MVPA was added. After culturing for 5 to 6 days, transient expression culture supernatants were harvested and purified by ProteinA affinity chromatography to obtain anti-CD27 chimeric antibodies, which are named as m2E7, m2B8, m4H3, m3E7, m1A8, m4G1, m2G3, m2F11 and m3B8, respectively.

Example 4 Characterization of the Anti-CD27 Chimeric Antibodies 4.1 Binding to Cell Surface CD27 (FACS)

Figure 1B:
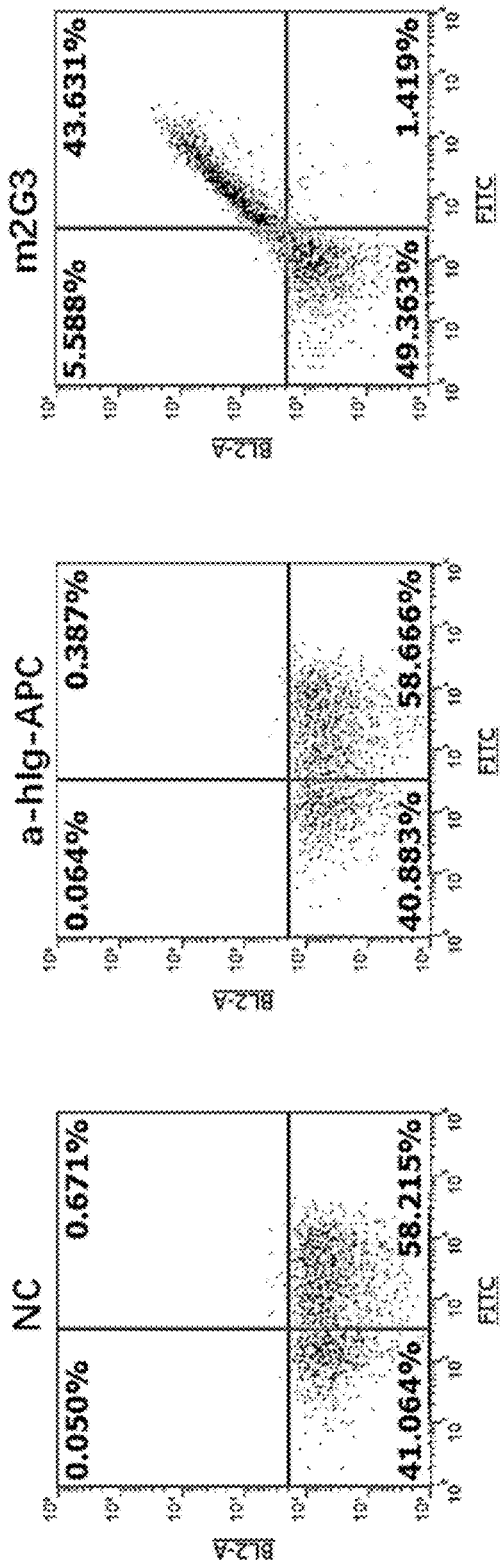
Figure 1B:
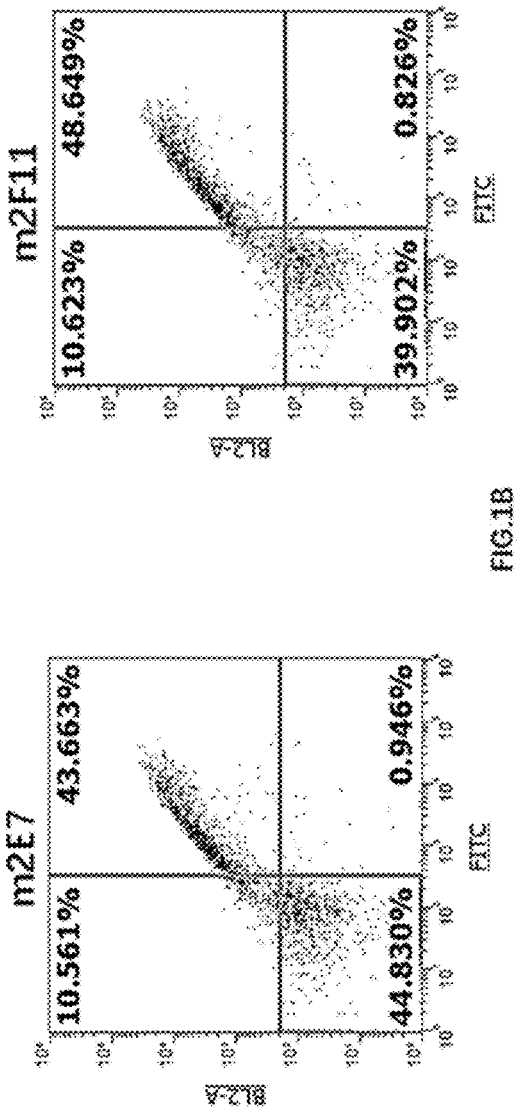

$5\times10^5$ CD27-EGFP cells prepared in Example 1 were washed twice in PBS, 10 µg/ml of each chimeric antibody prepared in Example 3 (m2E7, m2B8, m4H3, m3E7, m1A8, m4G1, m2G3, m2F11 and m3B8) was added to the cells and incubated at 4° C. for 30 min. Then it was washed twice in PBS, anti-human Ig-APC (Jackson ImmunoResearch Laboratories, Cat #109-135-098) was added, incubated at 4° C. for 30 min, washed twice with PBS and resuspended in 300 µl PBS. It was then examined by flow cytometry, and the results are shown in FIGS. 1A-1B. In FIGS. 1A-1B, NC represents negative control (PBS), a-hIg-APC represents secondary antibody only, the other panels represent results obtained with each of the corresponding clone, respectively.

It can be seen from the results of FIGS. 1A-1B that all the chimeric antibodies obtained from Example 3 could bind to cell surface CD27.

4.2 Binding Specificity to hCD27 (FACS)

Figure 2A:
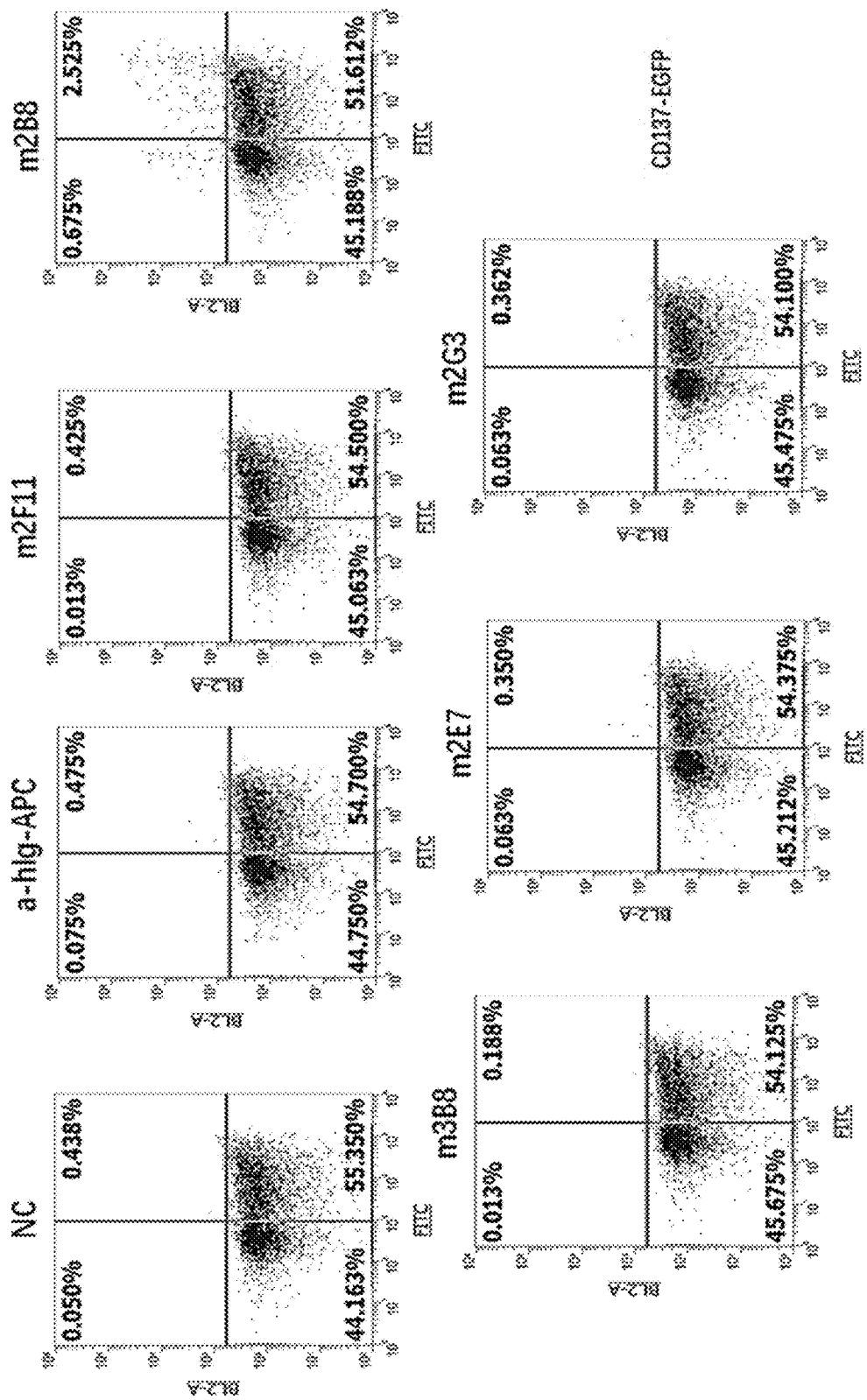
FIGS. 2A-2C illustrates the specific binding of the anti-CD27 antibodies of the present disclosure to human CD27, as detected by FACS.
Figure 2B:
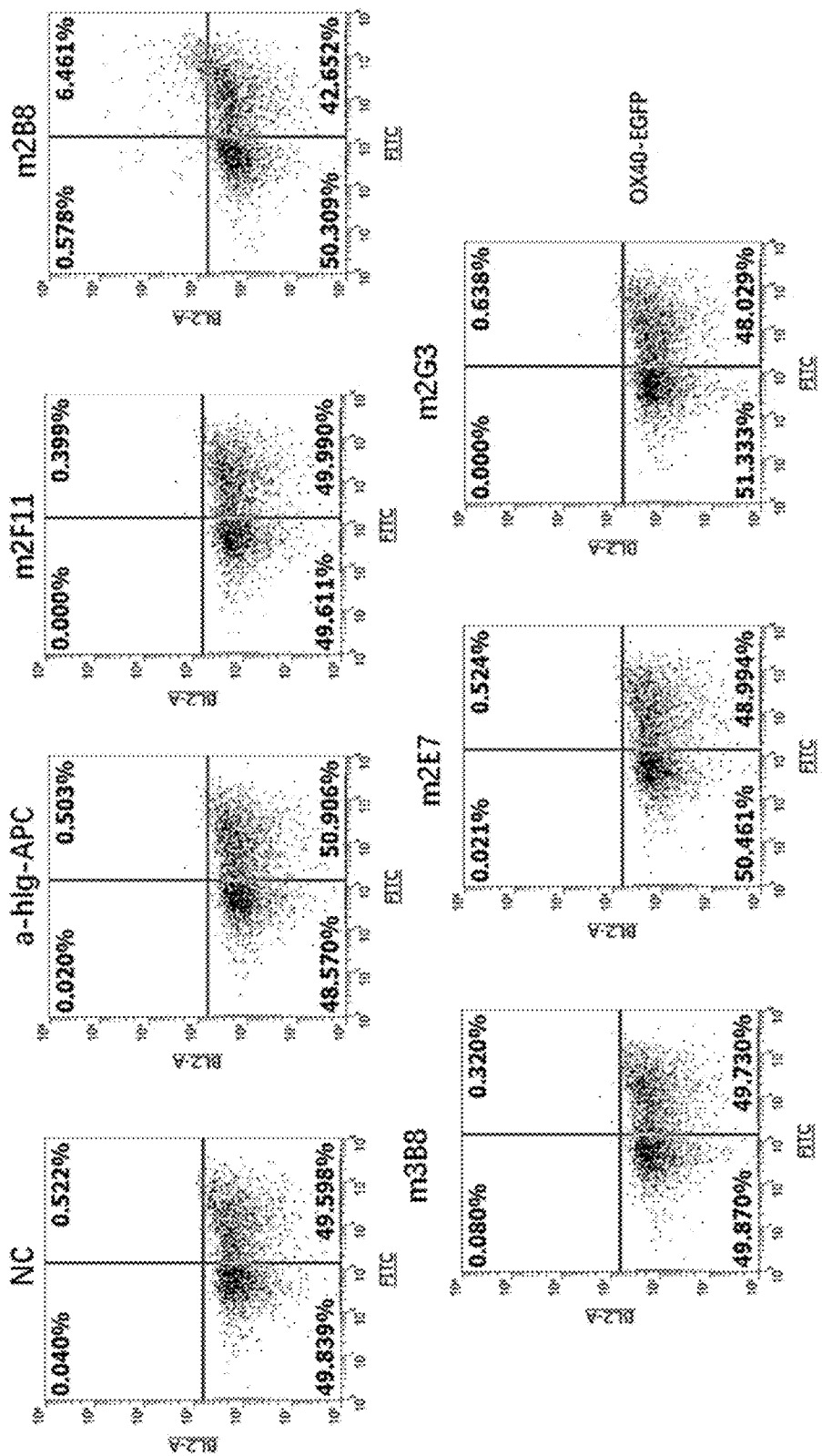
Figure 2C:
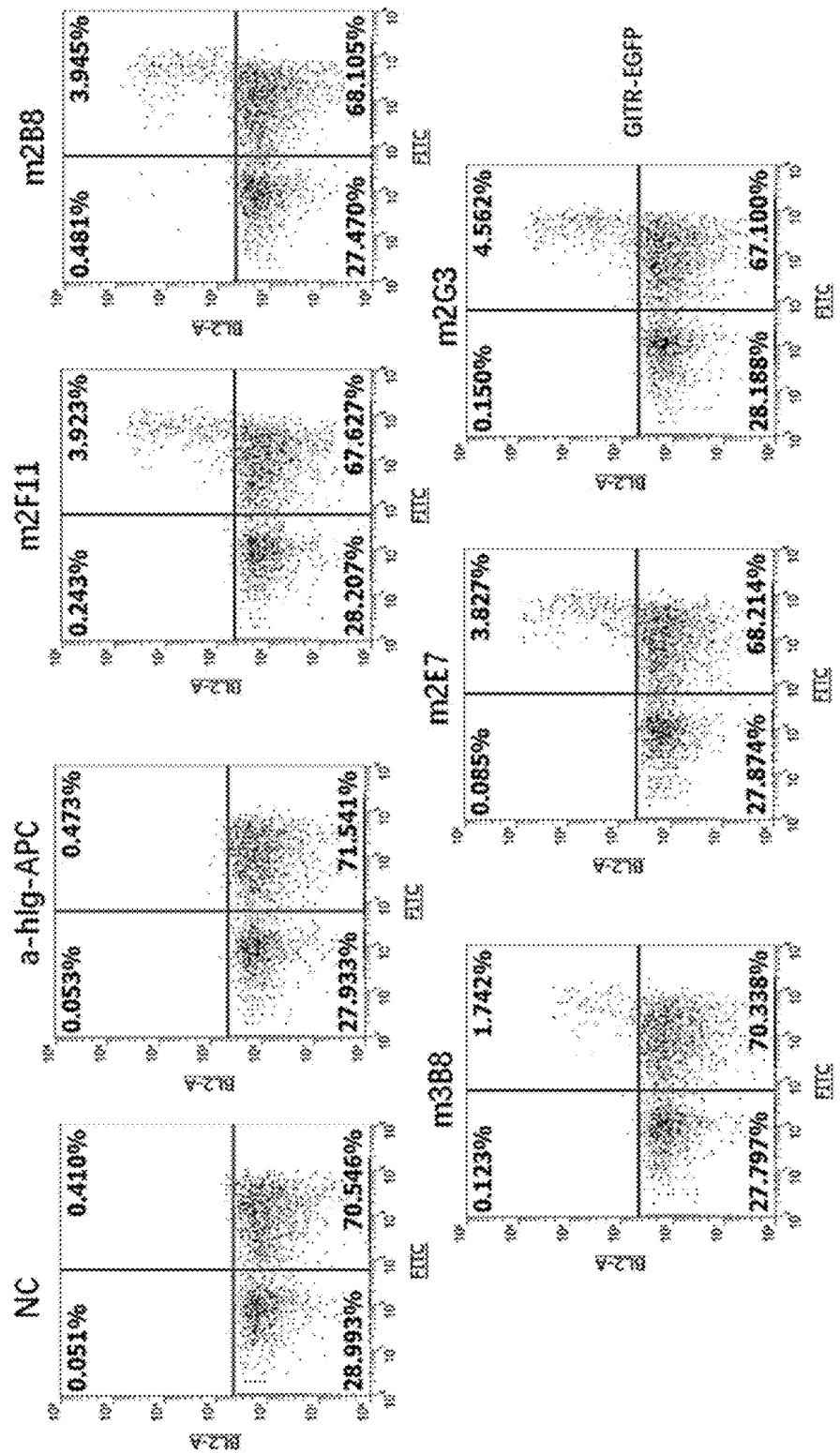

The hCD137-EGFP, hOX40-EGFP and hGITR-EGFP cells as described in Example 1 were washed twice in PBS, 10 µg/ml of each chimeric antibody as prepared in Example 3 (m2E7, m2B8, m4H3, m3E7, m1A8, m4G1, m2G3, m2F11 and m3B8) was added to each type of cells and incubated at 4° C. for 30 min. Then it was washed twice with PBS, anti-human Ig-APC (Jackson ImmunoResearch Laboratories, Cat #109-135-098) was added and were incubated at 4° C. for 30 min, washed twice with PBS and resuspended in 300 µl PBS. Then, flow cytometry was performed, and the results are shown in FIGS. 2A-2C. In FIGS. 2A-2C, NC represents negative control (PBS), a-hIg-APC represents secondary antibody only, the other panels represent results obtained with each of the corresponding clone, respectively.

It can be seen from the results of FIGS. 2A-2C that none of the chimeric antibodies prepared in Example 3 could substantially bind to hCD137, hOX40 or hGITR, demonstrating the binding specificity of the antibodies for hCD27.

4.3 Activation Assay

293T-CD27-NF-κB cells were digested with trypsin, after 2-3 mins, DMEM complete medium was added. The cells were gently suspended and transferred to 96-well plates, 100 µl/well. Supernatants from the 50 selected clones were mixed with anti-mouse crosslinking antibody (Jackson ImmunoResearch Laboratories: 109-006-008) and added to a 96-well plate. Complete medium was added to the control group. The cells were lysed after 30 hours and then tested using the luciferase assay system (Promega: E1501).

Figure 3:
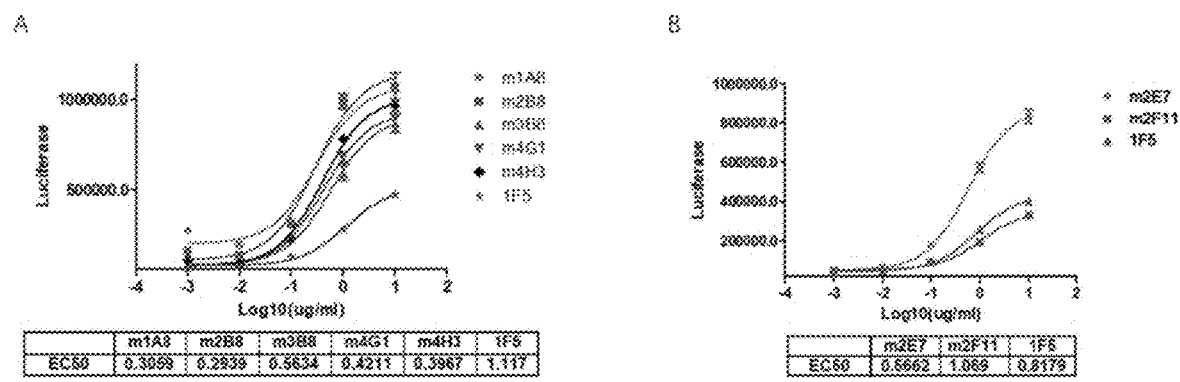
FIGS. 3A-3B illustrate the activation activity of the anti-CD27 antibodies according to the present disclosure.

The results are shown in FIGS. 3A-3B. The antibody 1F5 shown in FIG. 3B has been included as a benchmark control. It can be seen that all the chimeric antibodies prepared in Example 3 could activate downstream signaling and had a higher activation ability than the benchmark antibody 1F5.

4.4 Stimulation of T Cell Proliferation

Figure 4:
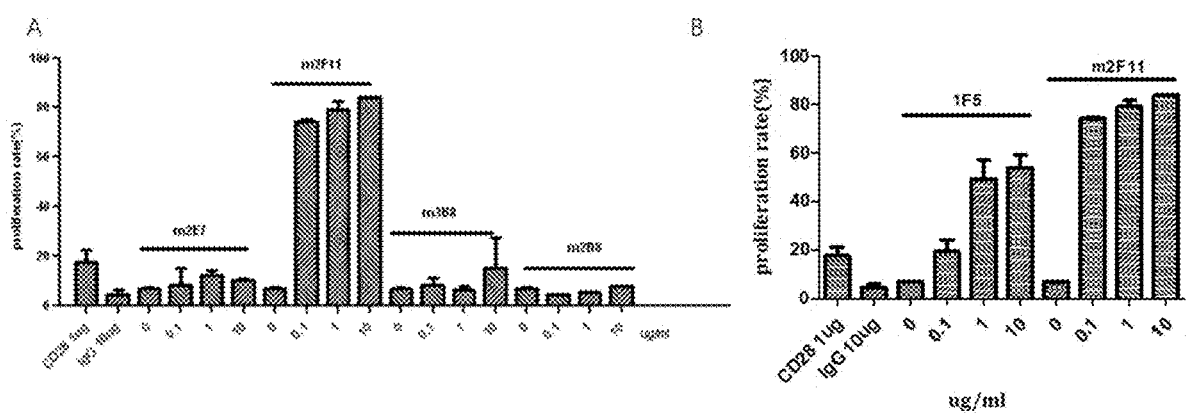
FIGS. 4A-4B illustrate the activity of the anti-CD27 antibodies of the present disclosure to stimulate T cell proliferation.

Peripheral blood mononuclear cells (PBMCs) were isolated from peripheral blood concentrates of healthy donors by density gradient centrifugation using isolation solution for human lymphocytes (Tianjin Gengyang), and PBMCs were isolated with EasySep Negative Human CD4 Kit (stem cell: 19052) to obtain $CD4^+$ T cells. The cells were washed twice with PBS and cell number was counted. The cells were then labeled with CFSE (Biolegend, cat. NO: 422701) according to the Biolegend instructions, washed twice with PBS, counted, and added to a 96-well plate with $1.5\times10^5$ cells per well. The 96-well plate was pre-coated with 3 µg/ml anti-CD3 antibody and the chimeric antibodies prepared in Example 3, incubated at 4° C. overnight. The negative control was incubated only with the anti-CD3 antibody, and the positive control was incubated with a soluble anti-CD28 antibody. The cells were washed 3 times with PBS on the next day. After adding the $CD4^+$ T cells into the 96-well plate, the 96-well plates were placed in a $CO_2$ incubator and incubated for 5 days. Then, the cells were collected, and cell proliferation was examined with flow cytometry. The results are shown in the FIG. 4A and FIG. 4B, the antibody 1F5 is a benchmark control. It can be seen from FIGS. 4A-4B that the clone m2F11 has the strongest activity in promoting T cell proliferation, which is even stronger than the benchmark antibody 1F5.

Example 5 Humanization of Anti-CD27 Antibodies

Based on the results obtained in the above examples, the clone m2F11 was selected, as an example, for humanization. The antibody was humanized by changing certain amino acid residues in the framework regions of the heavy chain variable regions and light chain variable regions. A total of 12 humanized heavy chain variable regions and 1 humanized light chain variable region were obtained, resulting in 12 humanized antibodies. The amino acid sequences of the 12 humanized antibodies are shown in Table 1 below:

TABLE 1

| Humanized antibody | VH | SEQ ID NO: | VL | SEQ ID NO: |
|---|---|---|---|---|
| d16647 | d16647VH | 115 | 16647VL | 91 |
| d12996 | d12996VH | 107 | | |
| d9419 | d9419VH | 95 | | |
| d9424 | d9424VH | 99 | | |
| d14822 | d14822VH | 111 | | |
| d12674 | d12674VH | 103 | | |
| 16647 | 16647VH | 113 | | |
| 12996 | 12996VH | 105 | | |
| 9419 | 9419VH | 93 | | |
| 9424 | 9424VH | 97 | | |
| 14822 | 14822VH | 109 | | |
| 12674 | 12674VH | 101 | | |

5.1 Expression and Purification of Humanized Antibodies

Nucleic acid molecules encoding the humanized VH and VL were synthesized. The nucleic acids encoding VH and that encoding the human IgG1 heavy chain constant region were fused to obtain the sequence encoding the antibody heavy chain, and the nucleic acids encoding VL and that encoding the human kappa light chain constant region were fused to obtain the sequence encoding the antibody light chain, as described in Example 3 for the chimeric antibodies. The obtained nucleic acid molecules were then cloned into the vector pcDNA4/myc-HisA, respectively, to obtain 12 heavy chain expression plasmids and one light chain expression plasmid. Each heavy chain expression plasmid was paired with a light chain expression plasmid and they were transiently transfected into the HEK293 cells (ATCC, CRL-1573™) for protein production. Briefly, the expression plasmids were diluted with Freestyle 293 medium and the PEI (Polyethyleneimine) solution was added. The plasmid/PEI mixture was added to the cell suspension and incubated under 37° C., 10% $CO_2$ at 90 rpm. After culturing for 5 to 6 days, transient expression culture supernatants were harvested and purified by ProteinA affinity chromatography to obtain the 12 humanized antibodies: d16647, d12996, d9419, d9424, d14822, d12674, 16647, 12996, 9419, 9424, 14822 and 12674, which would be used in the following examples. The obtained humanized antibodies were verified by SDS-PAGE (FIGS. 13A-13F) and the target bands were clearly seen. The yield of the humanized antibodies is shown in Table 2.

Figure 13:
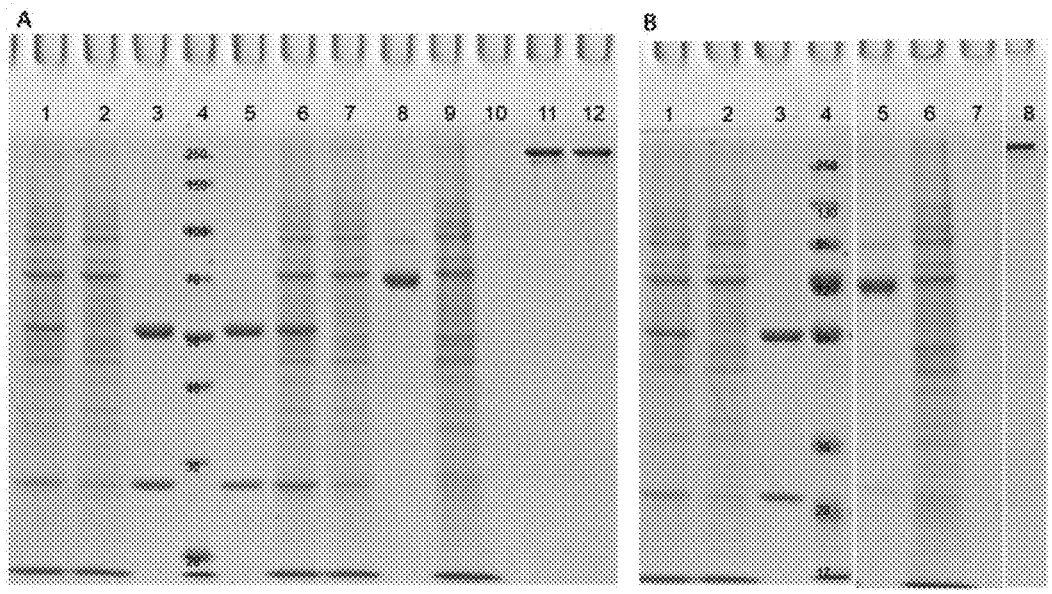
FIGS. 13A-13F illustrate the expression of the anti-CD27 antibodies according to the present disclosure by SDS-PAGE.
Figure 13:
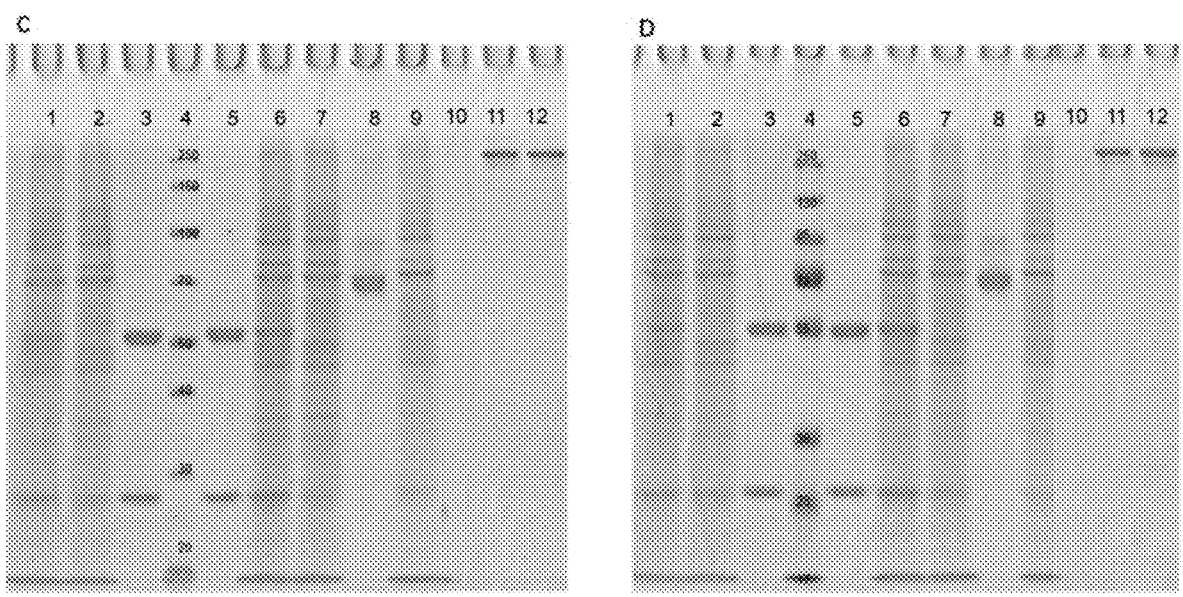
Figure 13:
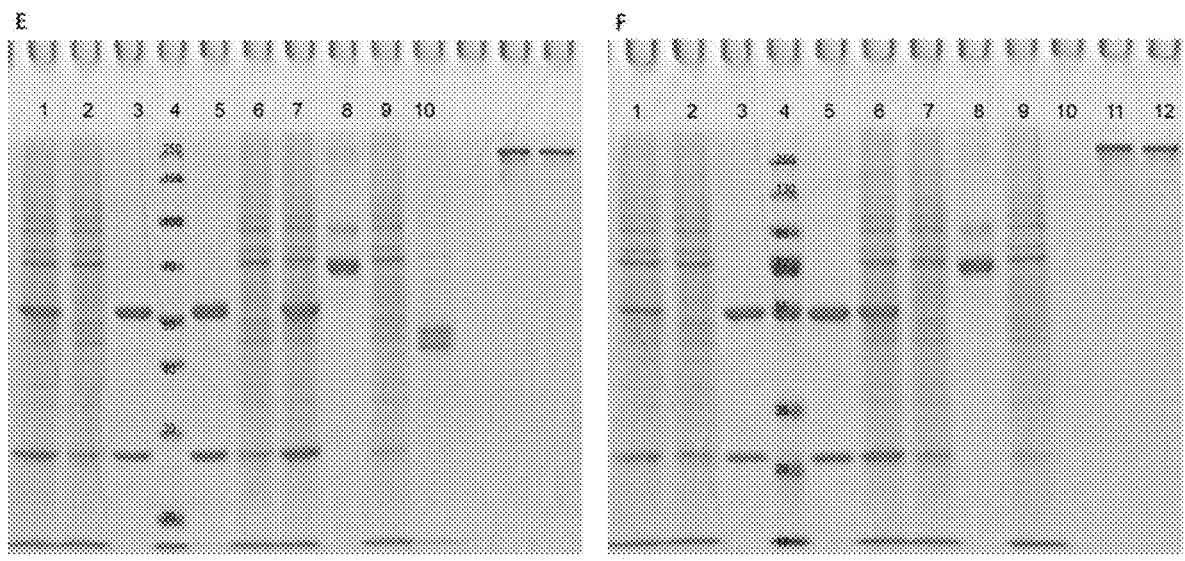

FIGS. 13A-13F showed that humanized antibodies d16647, 16647, d9419, 9419, 9424, d12996, 14822, 12674, d12674, 12996, d14822 was successfully expressed and purified. In FIG. 13A, lane 1 was loaded with 16647 (original sample); lane 2 was loaded with 16647 (flow-through); lane 3 was loaded with 16647 (eluted); lane 4 was loaded with marker (26630); lane 5 was loaded with d16647 (eluted); lane 6 was loaded with d16647 (original sample); lane 7 was loaded with d16647 (flow-through); lane 8 was loaded with 1 µg Std; lane 9 was blank; lane 10 was empty; lane 11 was loaded with 16647 (eluted, non-reducing); and lane 12 was loaded with d16647 (eluted, non-reducing).

In FIG. 13B, lane 1 was loaded with d9419 (original sample); lane 2 was loaded with d9419 (flow-through); lane 3 was loaded with d9419 (eluted); lane 4 was loaded with marker (26619); lane 5 was loaded with 1 µg Std; lane 6 was blank; lane 7 was empty and lane 8 was loaded with d9419 (eluted, non-reducing).

In FIG. 13C, lane 1 was loaded with 9419 (original sample); lane 2 was loaded with 9419 (flow-through); lane 3 was loaded with 9419 (eluted); lane 4 was loaded with marker (26630); lane 5 was loaded with 9424 (eluted); lane 6 was loaded with 9424 (original sample); lane 7 was loaded with 9424 (flow-through); lane 8 was loaded with 1 µg Std; lane 9 was blank; lane 10 was empty; lane 11 was loaded with 9419 (eluted, non-reducing); and lane 12 was loaded with 94924 (eluted, non-reducing).

In FIG. 13D, lane 1 was loaded with d12996 (original sample); lane 2 was loaded with d12996 (flow-through); lane 3 was loaded with d12996 (eluted); lane 4 was loaded with marker (26619); lane 5 was loaded with 14822 (eluted); lane 6 was loaded with 14822 (original sample); lane 7 was loaded with 14822 (flow-through); lane 8 was loaded with 1 µg Std; lane 9 was blank; lane 10 was empty; lane 11 was loaded with d12996 (eluted, non-reducing); and lane 12 was loaded with 14822 (eluted, non-reducing).

In FIG. 13E, lane 1 was loaded with 12674 (original sample); lane 2 was loaded with 12674 (flow-through); lane 3 was loaded with 12674 (eluted); lane 4 was loaded with marker (26630); lane 5 was loaded with d12674 (eluted); lane 6 was loaded with d12674 (original sample); lane 7 was loaded with d12674 (flow-through); lane 8 was loaded with 1 µg Std; lane 9 was blank; lane 10 was empty; lane 11 was loaded with 12674 (eluted, non-reducing); and lane 12 was loaded with d12674 (eluted, non-reducing).

In FIG. 13F, lane 1 was loaded with 12996 (original sample); lane 2 was loaded with 12996 (flow-through); lane 3 was loaded with 12996 (eluted); lane 4 was loaded with marker (26619); lane 5 was loaded with d14822 (eluted); lane 6 was loaded with d14822 (original sample); lane 7 was loaded with d14822 (flow-through); lane 8 was loaded with 1 µg Std; lane 9 was blank; lane 10 was empty; lane 11 was loaded with 12996 (eluted, non-reducing); and lane 12 was loaded with d14822 (eluted, non-reducing).

TABLE 2

| Antibody | Yield (µg/ml) |
|---|---|
| m2F11 | 91.2 |
| d16647 | 43 |
| d12996 | 7.28 |
| d9419 | 22.32 |
| d9424 | 5 |
| d14822 | 114.6 |
| d12674 | 132.6 |
| 16647 | 13.2 |
| 12996 | 32 |
| 9419 | 16 |
| 9424 | 29.2 |
| 14822 | 44 |
| 12674 | 79.92 |

5.2 Binding of the Humanized Antibodies to Human CD27 (ELISA)

Figure 5:
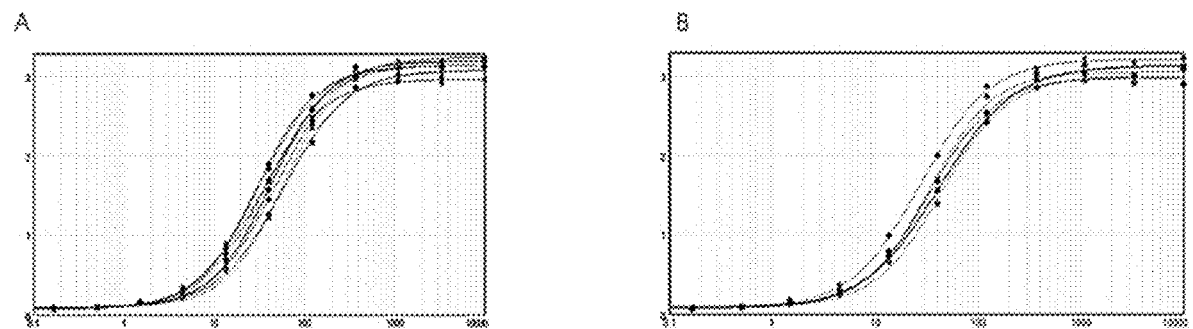
FIGS. 5A-5B illustrate binding of the anti-CD27 antibodies of the present disclosure to human CD27, as detected by ELISA.

The ELISA plate was coated with 2 µg/ml hCD27-muFc, 100 µl/well and incubated at 4° C. overnight. Then it was washed once with 10 mM, pH 7.4 PBS/Tween (0.05%), blocked with PBST containing 5% skimmed milk powder and incubated at 37° C. for 2 h. After washing the plate for 4 times, the humanized antibodies were added and incubated at 37° C. for 40 min, then it was washed for 4 times. Anti-human IgG-HRP-conjugated secondary antibody (Sigma, Cat #A0170-1M) was added and incubated at 37° C. for 40 min. After washing, the plate was developed with TMB substrate and spectrophotometric analysis was performed at $OD_{450}$. The results are shown in the FIGS. 5A-5B. and Table 3. In FIGS. 5A-5B, each curve represents the binding result obtained for one of the humanized antibodies. From the results, it can be seen that all these humanized antibodies could bind to human CD27.

TABLE 3

| Antibody | Human CD27 $EC_{50}$ (ng/ml) |
|---|---|
| Test 1 | |
| m2F11 | 31.51 |
| d16647 | 37.58 |
| d12996 | 30.02 |
| d9419 | 33.04 |
| 12996 | 50.58 |
| 9419 | 58.33 |
| 14822 | 42.73 |
| 12674 | 58.52 |
| Test 2 | |
| m2F11 | 27.88 |
| d14822 | 33.87 |
| d12674 | 42.41 |
| 16647 | 44.51 |
| 9424 | 34.16 |

5.3 Binding to Cell Surface CD27 (FACS)

Based on the above results of ELISA, 7 humanized antibodies were selected to examine their affinities to cell surface CD27. Briefly, $5\times10^5$ CD27-EGFP cells prepared in Example 1 were washed twice in PBS, each of the humanized antibodies (d16647, d12996, d9419, 14822, 9424, d14822, d12674) was added. The antibodies were subjected to 3-fold serial dilution, starting from 20 μg/ml, to obtain 8 gradient dilutions for each antibody. The antibodies and the cells were incubated at 4° C. for 30 min. Then, it was washed twice with PBS, anti-human Ig-APC (Jackson ImmunoResearch Laboratories, Cat #109-135-098) was added, and incubated at 4° C. for 30 min, washed twice with PBS and resuspended in 300 μl PBS. Flow cytometry was then performed, and the results are shown in FIG. 6. m2F11 was used as a control.

Figure 6:
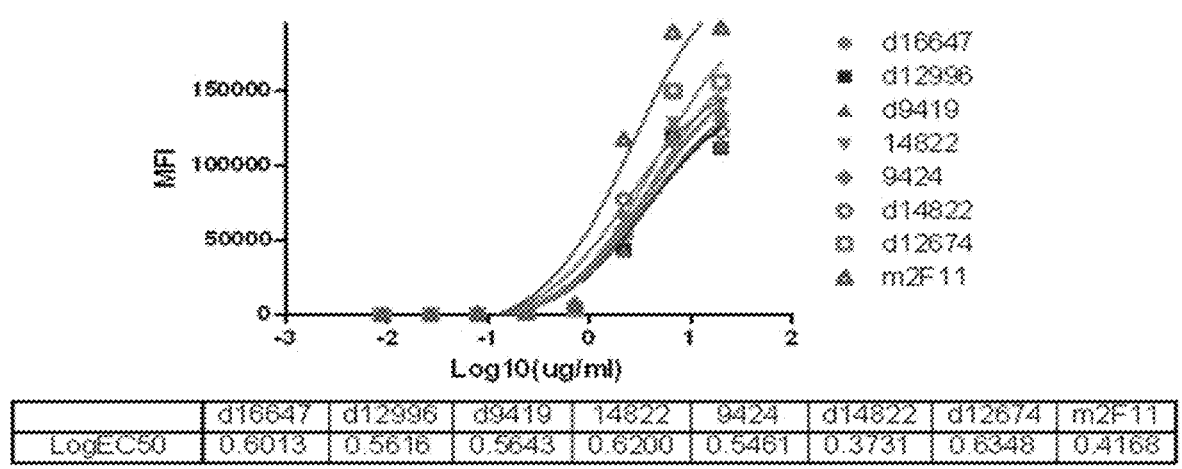
FIG. 6 illustrates binding of the anti-CD27 antibodies of the present disclosure to CD27 on human cell surface, as detected by FACS.

It can be seen from the results of FIG. 6 that all these humanized antibodies could bind to cell surface CD27.

5.4 Binding Kinetics to Human CD27 Protein

Using the BLI method, each humanized antibody was immobilized on a Protein A biosensor at a concentration of 10 μg/ml, while hCD27-muFc was subjected to 2-fold serial dilution, starting from 100 nM, to obtain 5 gradient dilutions for each antibody. The reaction plate was placed on the Octet K2 instrument. The parameters were set to Baseline 70 s, Association 80 s, Dissociation 300 s, Baseline 260 s, Loading 40 s, and Custom 5 s. The results are shown in Table 4.

TABLE 4

| Antibodies | KD (M) | $K_{on}$ (1/Ms) | $K_{off}$ (1/s) |
|---|---|---|---|
| m2F11 | $8.35 \times 10^{-10}$ | $1.30 \times 10^5$ | $1.08 \times 10^{-4}$ |
| d16647 | $3.05 \times 10^{-9}$ | $9.21 \times 10^4$ | $2.81 \times 10^{-4}$ |
| d12996 | $3.39 \times 10^{-9}$ | $9.62 \times 10^4$ | $3.26 \times 10^{-4}$ |
| d9419 | $1.70 \times 10^{-9}$ | $1.20 \times 10^5$ | $2.05 \times 10^{-4}$ |
| d14822 | $4.27 \times 10^{-9}$ | $7.82 \times 10^4$ | $3.34 \times 10^{-4}$ |
| d12674 | $5.00 \times 10^{-9}$ | $8.94 \times 10^4$ | $4.47 \times 10^{-4}$ |
| 16647 | $4.86 \times 10^{-9}$ | $7.15 \times 10^4$ | $3.48 \times 10^{-4}$ |
| 12996 | $4.98 \times 10^{-9}$ | $7.39 \times 10^4$ | $3.68 \times 10^{-4}$ |
| 9419 | $2.73 \times 10^{-9}$ | $1.05 \times 10^5$ | $2.87 \times 10^{-4}$ |
| 9424 | $7.02 \times 10^{-9}$ | $5.65 \times 10^4$ | $3.96 \times 10^{-4}$ |
| 14822 | $5.15 \times 10^{-9}$ | $9.70 \times 10^4$ | $4.99 \times 10^{-4}$ |
| 12674 | $3.66 \times 10^{-9}$ | $7.95 \times 10^4$ | $2.91 \times 10^{-4}$ |

5.5 Binding to Monkey Cell Surface CD27 (FACS)

$5\times10^5$ RhCD27-EGFP cells as prepared in Example 1 were washed twice with PBS, 10 μg/ml humanized antibody prepared in Example 5 (d9419, d16647, d14822, d12674) was added and incubated at 4° C. for 30 min. Then it was washed twice with PBS, anti-human Ig-APC (Jackson ImmunoResearch Laboratories, Cat #109-135-098) was added and incubate at 4° C. for 30 min, washed twice with PBS and was resuspended in 300 μl PBS. Then flow cytometry was performed, and the results are shown in FIG. 7. m2F11 was used as a control.

Figure 7:
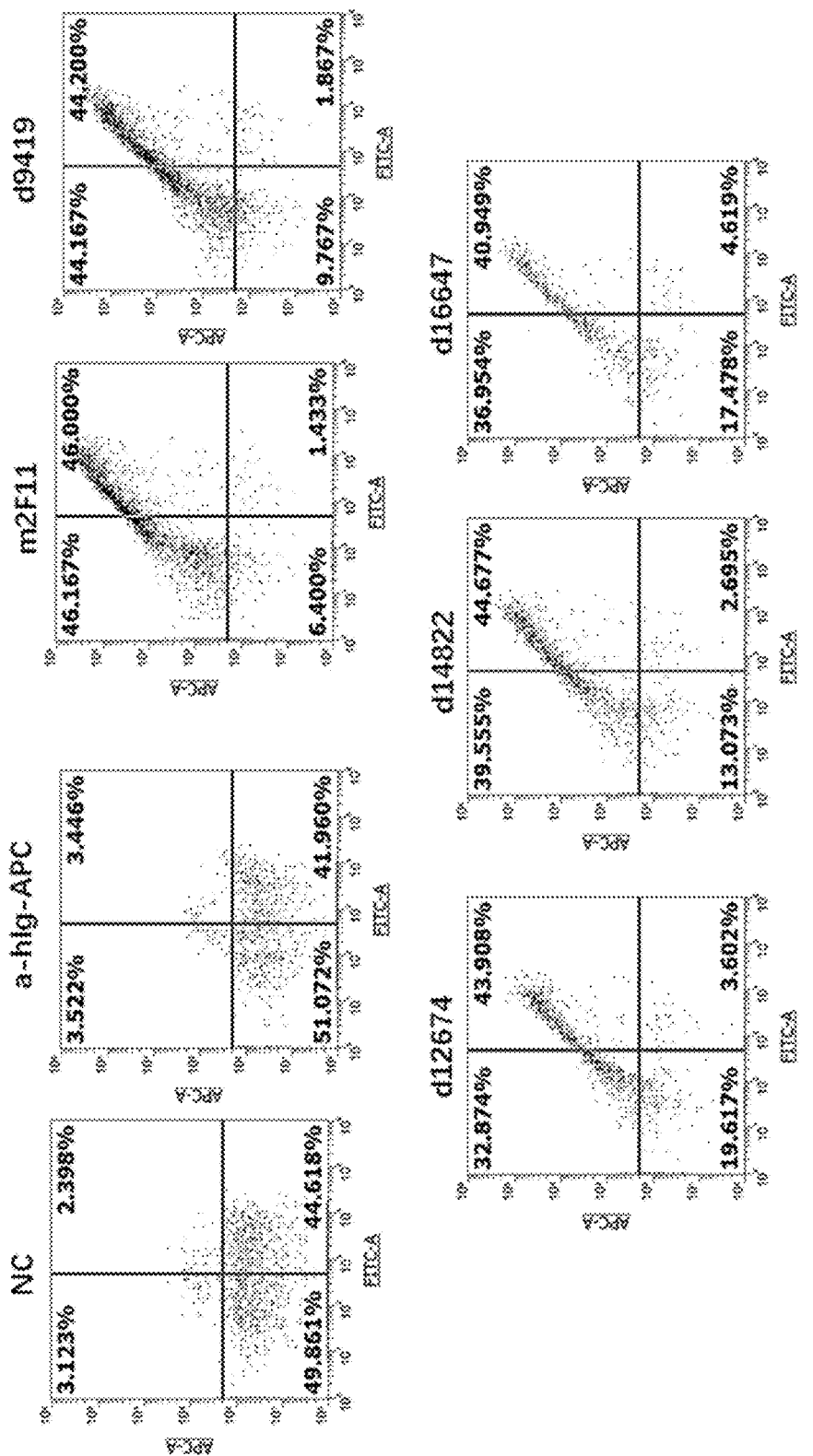
FIG. 7 illustrates binding of the anti-CD27 antibodies of the present disclosure to CD27 on monkey cell surface, as detected by FACS.

It can be seen from the results of FIG. 7 that these humanized antibodies could bind to monkey cell surface RhCD27.

5.6 Activation Assay

293T-CD27-NF-κB cells were digested with trypsin, after 2-3 mins, DMEM complete medium was added. The cells were gently suspended and transferred to 96-well plates, 100 μl/well. The humanized antibodies prepared in Example 5 were subjected to 10-fold dilution, starting from 10 μg/ml, and the diluted antibodies were mixed with the anti-human crosslinking antibody (Jackson Immuno Research Laboratories: 109-006-008) and added to a 96-well plate. Complete medium was added into the control group. The cells were lysed after 30 hours and then tested using the luciferase assay system (Promega: E1501). The results are shown in FIG. 8, and every curve in FIG. 8 represents the result obtained for one humanized antibody, m2F11 was used as a control.

Figure 8:
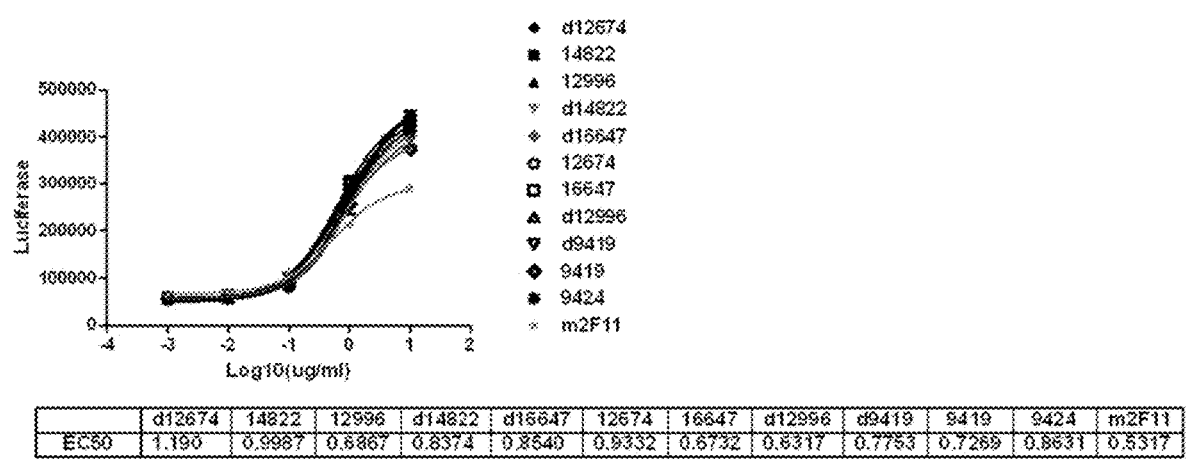
FIG. 8 illustrates the activation activity of the anti-CD27 antibodies according to the present disclosure.

It can be seen from the results in FIG. 8 that the humanized antibodies could still activate downstream signaling.

5.7 Stimulation of T Cell Proliferation

Peripheral blood mononuclear cells (PBMCs) were isolated from peripheral blood concentrates of healthy donors by density gradient centrifugation using isolation solution for human lymphocytes (Tianjin Gengyang), and PBMCs were isolated with EasySep Negative Human CD4 Kit (stem cell: 19052) to obtain $CD4^+$ T cells. The cells were washed twice with PBS and cell number was counted. The cells were then labeled with CFSE (Biolegend, cat. NO: 422701) according to the Biolegend instructions, washed twice with PBS, counted, and added to a 96-well plate with $1.5\times10^5$ cells per well. The 96-well plate was pre-coated with 3 μg/ml anti-CD3 antibody and the chimeric antibodies prepared in Example 3, incubated at 4° C. overnight. The negative control was incubated only with the anti-CD3 antibody, and the positive control was incubated with a soluble anti-CD28 antibody. The cells were washed 3 times with PBS on the next day. After adding the $CD4^+$ T cells into the 96-well plate, the 96-well plates were placed in a $CO_2$ incubator and incubated for 5 days. Then, the cells were collected, and cell proliferation was examined with flow cytometry. In addition, the supernatant was collected and the secretion of IFN-γ in the supernatant was examined using a CBA detection kit (BD, cat. NO: 551809).

Figure 9:
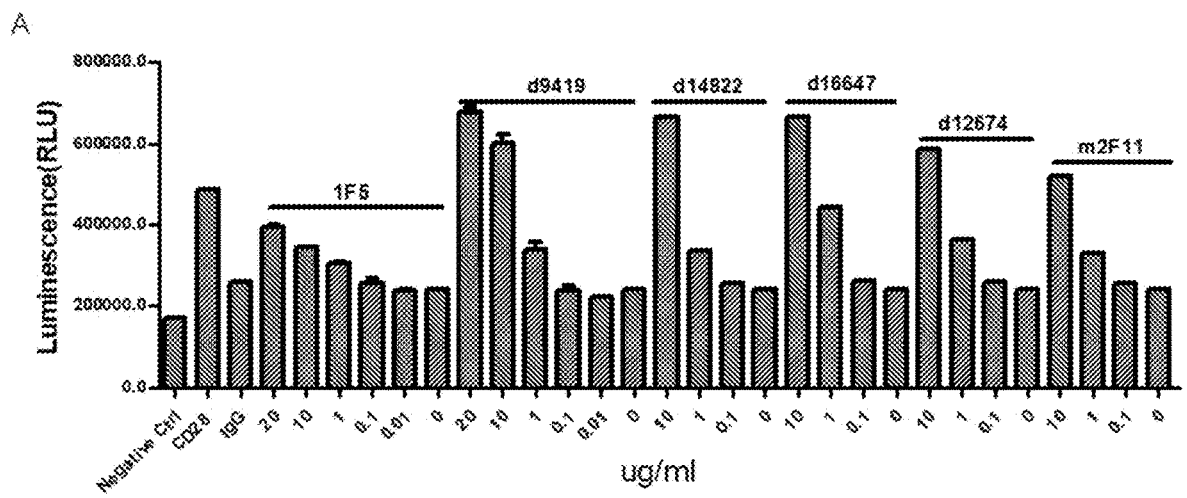
FIG. 9A illustrates the activity of the anti-CD27 antibodies of the present disclosure to stimulate T cell proliferation.
FIG. 9B illustrates the activity of the anti-CD27 antibodies of the present disclosure to stimulate the secretion of IFN-γ by T cells.
Figure 9:
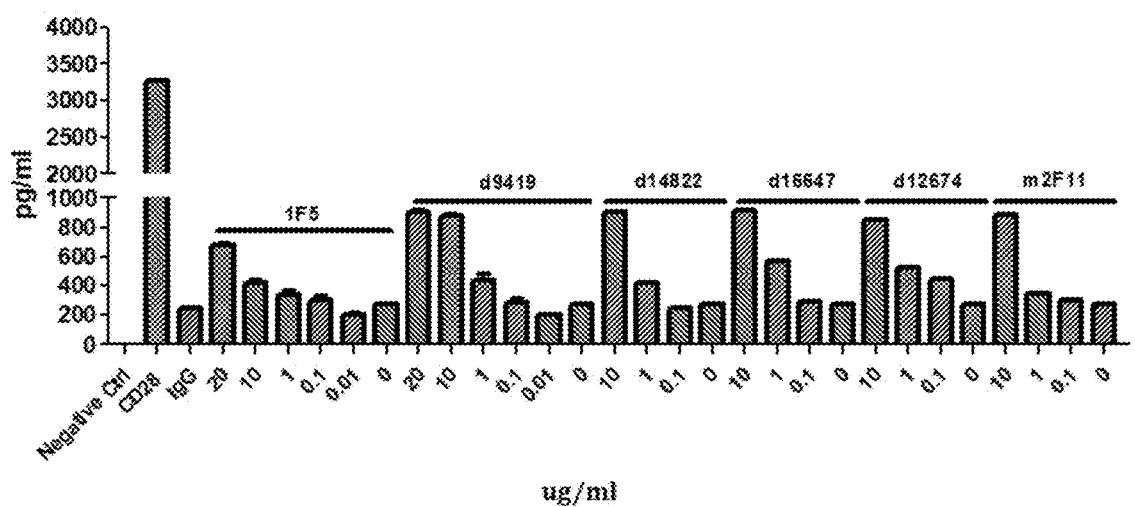

The results are shown in the FIG. 9A and FIG. 9B. FIG. 9A shows that the anti-CD27 humanized antibodies could stimulate T cell proliferation, even more significant than the antibody m2F11. FIG. 9B shows that the anti-CD27 humanized antibodies could stimulate secretion of IFN-γ by T cells.

Example 6 Antibody Stability

6.1 Testing of Antibody Stability by Differential Scanning Calorimetry (DSC)

DSC was used to test the thermal stability of the humanized antibodies. The DSC scanning results obtained with buffer only and that with buffers comprising proteins were obtained as control. Each humanized antibody was diluted to 1 mg/ml (PBS buffer). The following parameters were used: 10-110° C., 100° C. per hour, 15 min balancing time before each scan. The sample volume was 0.5 ml. The results were calibrated against the scanning data collected with the buffer only, and those with the buffer comprising proteins. Then, the $T_m$ values of the humanized antibodies were obtained, as shown in Table 5.

TABLE 5

| Antibodies | $T_m$ (° C.) |
|---|---|
| m2F11 | 65.7 |
| d16647 | 67 |
| d12996 | 59.5 |
| d9419 | 66.5 |
| d14822 | 67.5 |
| d12674 | 68 |
| 16647 | 65.5 |
| 12996 | 64.5 |
| 9419 | 64.2 |
| 9424 | 66.8 |

TABLE 5-continued

| Antibodies | $T_m$ (° C.) |
|---|---|
| 14822 | 66.2 |
| 12674 | 66.7 |

6.2 Accelerated Stabilization Test

Figure 10:
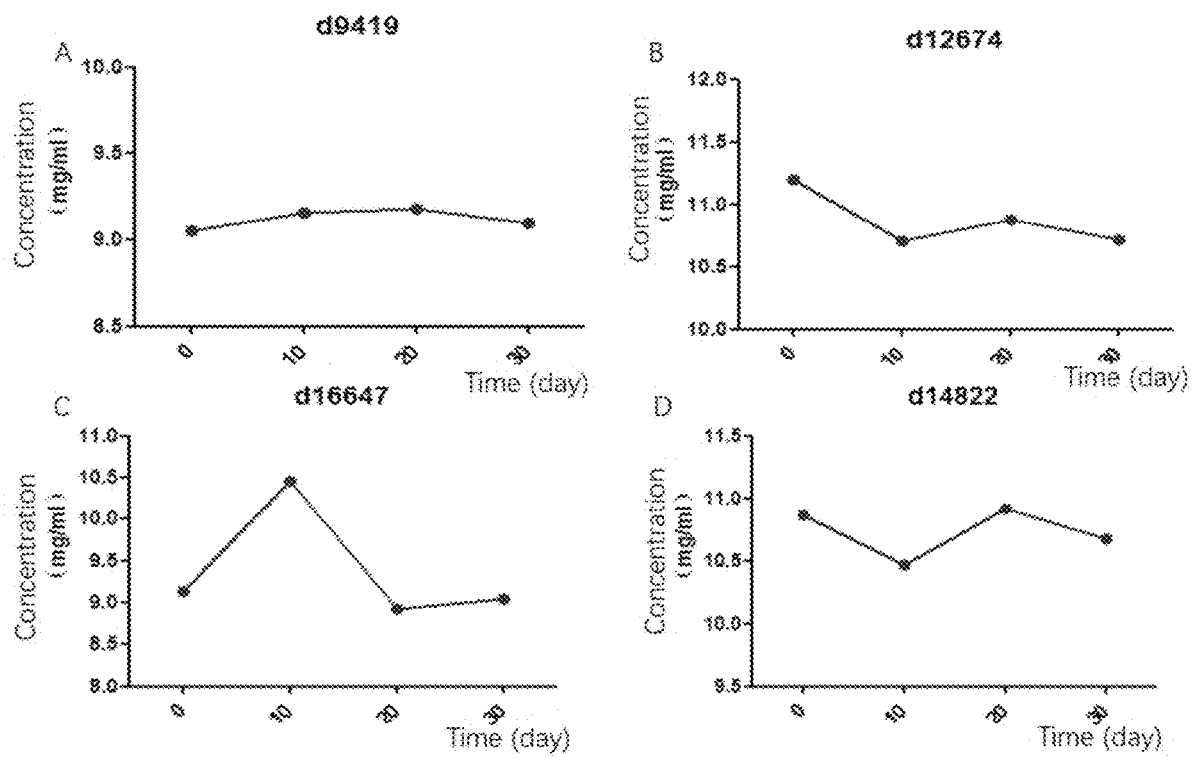
FIGS. 10A-10D illustrate the stability of the anti-CD27 antibodies according to the present disclosure.
Figure 11:
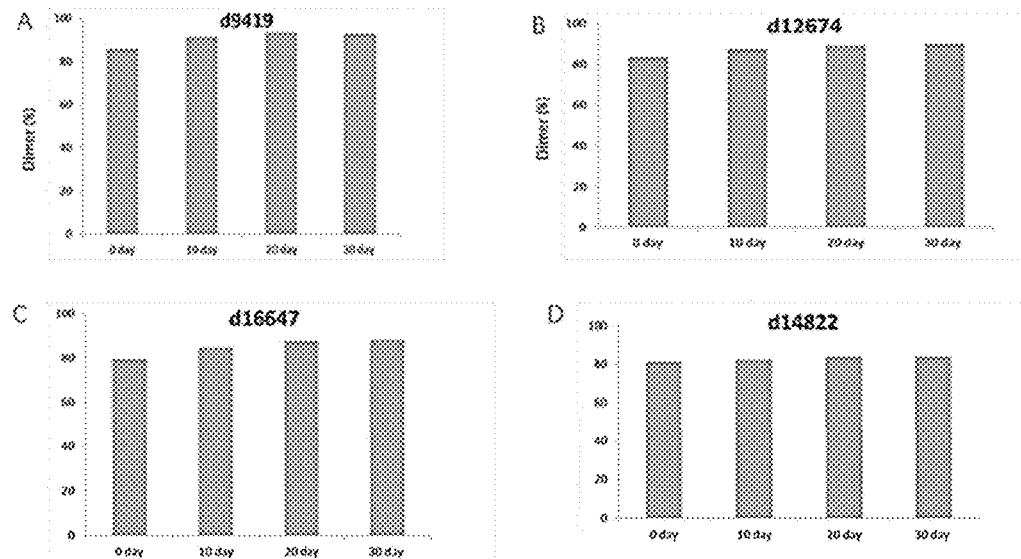
FIGS. 11A-11D illustrate the stability of the anti-CD27 antibodies according to the present disclosure.

45° C. accelerated stabilization test was performed for the humanized antibodies. Briefly, one-step ProteinA purified antibodies were dissolved in PBS (pH 7.4), and the antibody was concentrated to approximately 10 mg/ml. 100 µg antibody was added into a 200 µl PCR tube, incubated at 45° C. Samples were taken on day 0, day 10, day 20, and day 30 for detection under A280 and SEC-HPLC analysis. The results are shown in FIG. 10 and FIG. 11, respectively. FIG. 10 shows change of the antibody concentration with time, and FIG. 11 shows change of the percentage of antibody dimers with time. It can be seen from these results that the antibody concentration did not change significantly with time, and the percentage of antibody dimers has not changed significantly with time. In addition, formation of trimers or aggregations was not observed.

While preferred embodiments of the present application have been shown and described herein, it will be obvious to those skilled in the art that such embodiments are provided by way of example only. It is not intended that the application be limited by the specific examples provided within the specification. While the application has been described with reference to the aforementioned specification, the descriptions and illustrations of the embodiments herein are not meant to be construed in a limiting sense. Numerous variations, changes, and substitutions will now occur to those skilled in the art without departing from the application. Furthermore, it shall be understood that all aspects of the application are not limited to the specific depictions, configurations or relative proportions set forth herein which depend upon a variety of conditions and variables. It should be understood that various alternatives to the embodiments of the application described herein may be employed in practicing the application. It is therefore contemplated that the application shall also cover any such alternatives, modifications, variations or equivalents. It is intended that the following claims define the scope of the application and that methods and structures within the scope of these claims and their equivalents be covered thereby.

What is claimed is:

1. An antibody or an antigen binding fragment thereof, which binds to CD27, wherein said antibody comprises a light chain or a fragment thereof, the light chain or the fragment thereof comprises a light chain CDR1, a light chain CDR2, and a light chain CDR3, and said light chain CDR1 comprises an amino acid sequence as set forth in SEQ ID NO: 88, said light chain CDR2 comprises an amino acid sequence as set forth in SEQ ID NO: 89, and said light chain CDR3 comprises an amino acid sequence as set forth in SEQ ID NO: 90; and said antibody comprises a heavy chain or a fragment thereof, the heavy chain or the fragment thereof comprises a heavy chain CDR1, a heavy chain CDR2, and a heavy chain CDR3, and said heavy chain CDR1 comprises an amino acid sequence as set forth in SEQ ID NO: 85, said heavy chain CDR2 comprises an amino acid sequence as set forth in SEQ ID NO: 86, and said heavy chain CDR3 comprises an amino acid sequence as set forth in SEQ ID NO: 87.

2. The antibody or the antigen binding fragment thereof according to claim 1, wherein said light chain or a fragment thereof comprises a light chain variable region, and said light chain variable region comprises an amino acid sequence selected from SEQ ID NO: 83 and 91.

3. The antibody or the antigen binding fragment thereof according to claim 1, wherein said light chain or a fragment thereof comprises an amino acid sequence as set forth in SEQ ID NO: 131.

4. The antibody or the antigen binding fragment thereof according to claim 1, wherein said heavy chain or the fragment thereof comprises a heavy chain variable region, and said heavy chain variable region comprises an amino acid sequence selected from SEQ ID NO: 81, 93, 95, 97, 99, 101, 103, 105, 107, 109, 111, 113 and 115.

5. The antibody or the antigen binding fragment thereof according to claim 1, wherein said heavy chain or the fragment thereof comprises an amino acid sequence as set forth in SEQ ID NO:132.

6. The antibody or the antigen binding fragment thereof according to claim 5, wherein said CD27 is selected from the group consisting of: a human CD27 and a monkey CD27.

7. A composition, comprising the antibody or the antigen binding fragment thereof according to claim 1, and a pharmaceutically acceptable excipient.

8. Method of treating cancer in a subject in need thereof, comprising administering an effective amount of the antibody or the antigen binding fragment thereof according to claim 1 to the subject, wherein the antibody or the antigen binding fragment thereof activates CD27.

* * * * *